US009247747B2

(12) United States Patent
Dietz et al.

(10) Patent No.: US 9,247,747 B2
(45) Date of Patent: Feb. 2, 2016

(54) FUNGICIDAL SUBSTITUTED 1-{2-[2-HALO-4-(4-HALOGEN-PHENOXY)-PHENYL]-2-ALKOXY-2-ALKYNYL/ALKENYL-ETHYL}-1H-[1,2,4]TRIAZOLE COMPOUNDS

(75) Inventors: Jochen Dietz, Karlsruhe (DE); Richard Riggs, Mannheim (DE); Nadege Boudet, Hemsbach (DE); Jan Klaas Lohmann, Lambsheim (DE); Ian Robert Craig, Ludwigshafen (DE); Egon Haden, Speyer (DE); Erica May Wilson Lauterwasser, Mannheim (DE); Bernd Müller, Frankenthal (DE); Wassilios Grammenos, Ludwigshafen (DE); Thomas Grote, Wachenheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/237,470

(22) PCT Filed: Aug. 14, 2012

(86) PCT No.: PCT/EP2012/065852
§ 371 (c)(1),
(2), (4) Date: Feb. 6, 2014

(87) PCT Pub. No.: WO2013/024083
PCT Pub. Date: Feb. 21, 2013

(65) Prior Publication Data
US 2014/0206538 A1 Jul. 24, 2014

(30) Foreign Application Priority Data
Aug. 15, 2011 (EP) .................................... 11177557

(51) Int. Cl.
C07D 249/08 (2006.01)
A01N 43/653 (2006.01)

(52) U.S. Cl.
CPC ............ *A01N 43/653* (2013.01); *C07D 249/08* (2013.01)

(58) Field of Classification Search
CPC .................................................. C07D 249/08
See application file for complete search history.

(56) References Cited

U.S. PATENT DOCUMENTS

| 4,242,121 | A | 12/1980 | Hawkins et al. |
| 4,599,362 | A | 7/1986 | Nakatani et al. |
| 4,940,720 | A | 7/1990 | Nevill et al. |
| 4,945,100 | A | 7/1990 | Nyfeler et al. |
| 4,992,458 | A | 2/1991 | Riebli et al. |
| 5,143,932 | A | 9/1992 | Jautelat et al. |
| 5,162,358 | A | 11/1992 | Jautelat et al. |
| 2008/0108686 | A1 | 5/2008 | Gewehr et al. |
| 2009/0036509 | A1 | 2/2009 | Gewehr et al. |
| 2009/0286768 | A1 | 11/2009 | Crew et al. |

FOREIGN PATENT DOCUMENTS

| AU | 611315 | 6/1991 |
| CA | 1100976 | 5/1981 |
| CA | 1 209 152 | 8/1986 |
| CN | 101225074 | 7/2008 |
| CS | 247 200 | 12/1986 |
| DE | 2 325 878 | 12/1974 |
| DE | 3801233 | 8/1988 |
| DE | 40 03 180 | 8/1991 |
| EP | 0 000 017 | 12/1978 |
| EP | 0 113 640 | 7/1984 |
| EP | 0 126 430 | 11/1984 |
| EP | 0 275 955 | 7/1988 |
| EP | 0 354 183 | 2/1990 |
| EP | 0 440 950 | 8/1991 |
| EP | 0 470 466 | 2/1992 |
| EP | 1 431 275 | 6/2004 |
| FR | 2 491 924 | 4/1982 |
| GB | 2 132 195 | 7/1984 |
| WO | WO 96/41804 | 12/1996 |
| WO | WO 03 064572 | 8/2003 |
| WO | WO 2005/123689 | 12/2005 |
| WO | WO 2005/123690 | 12/2005 |
| WO | WO 2006/015866 | 2/2006 |
| WO | WO 2006/087373 | 8/2006 |
| WO | WO 2006/109933 | 10/2006 |
| WO | WO 2006/119876 | 11/2006 |
| WO | WO 2008/082198 | 7/2008 |
| WO | WO 2010/146114 | 12/2010 |
| WO | WO 2011/099804 | 8/2011 |
| WO | WO 2012/037782 | 3/2012 |
| WO | WO 2013/010862 | 1/2013 |
| WO | WO 2013/010885 | 1/2013 |
| WO | WO 2013/010894 | 1/2013 |
| WO | WO 2013/024076 | 1/2013 |
| WO | WO 2013/024077 | 1/2013 |
| WO | WO 2013/024082 | 1/2013 |
| WO | WO 2013007767 | 1/2013 |
| WO | WO 2013/024075 | 2/2013 |
| WO | WO 2013/024080 | 2/2013 |
| WO | WO 2013/024081 | 2/2013 |

OTHER PUBLICATIONS

International Search Report dated , prepared in International Application No. PCT/EP2012/065852.
International Preliminary Report on Patentability dated Jun. 17, 2013, prepared in International Application No. PCT/EP2012/065852.

(Continued)

*Primary Examiner* — Shawquia Jackson
(74) *Attorney, Agent, or Firm* — Brinks Gilson & Lione

(57) ABSTRACT

The present invention relates to substituted 1-{2-[2-halo-4-(4-halogen-phenoxy)-phenyl]-2-alkoxy-2-alkynyl-ethyl}-1H-[1,2,4]triazole compounds of formula I as defined in the description, and the N-oxides, and salts thereof, processes and intermediates for preparing these compounds and also to compositions comprising at least one such compound. The invention also relates to the use of such compounds and compositions for combating harmful fungi and seed coated with at least one such compound.

18 Claims, No Drawings

(56) References Cited

OTHER PUBLICATIONS

European Search Report dated Nov. 8, 2011, prepared in European Application No. 11177557.3, Aug. 11, 2011.
Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.
Akama, Tsutomu, et al. "Discovery and structure-activity study of a novel benzoxaborole anti-inflammatory agent (AN2728) for the potential topical treatment of psoriasis and atopic dermatitis", Medicinal Chemistry Letters, 2009, p. 2129-2132, vol. 19.
Final Office Action dated Jun. 23, 2015, issued in U.S. Appl. No. 14/237,463.
Final Office Action dated Jun. 12, 2015, issued in U.S. Appl. No. 14/237,048.
Office Action dated Dec. 10, 2014, issued in U.S. Appl. No. 14/237,463.
Office Action dated Dec. 1, 2014, issued in U.S. Appl. No. 14/232,434.
Office Action dated Dec. 8, 2014, issued in U.S. Appl. No. 14/232,462.
Office Action dated Dec. 8, 2014, issued in U.S. Appl. No. 14/237,048.
Lima, Lidia Moreira et al., "Bioisosterism: A useful strategy for molecular Modification and drug design", Current Medicinal Chemistry, 2005, p. 23-49, vol. 12.

FUNGICIDAL SUBSTITUTED 1-{2-[2-HALO-4-(4-HALOGEN-PHENOXY)-PHENYL]-2-ALKOXY-2-ALKYNYL/ALKENYL-ETHYL}-1H-[1,2,4]TRIAZOLE COMPOUNDS

This application is a National Stage application of International Application No. PCT/EP2012/065852, filed Aug. 14, 2012, the entire contents of which is hereby incorporated herein by reference. This application also claims priority under 35 U.S.C. §119 to European Patent Application No. 11177557.3, filed Aug. 15, 2011, the entire contents of which is hereby incorporated herein by reference.

The present invention relates to fungicidal 1-{2-[2-halo-4-(4-halogen-phenoxy)-phenyl]-2-alkoxy-2-alkynyl/alkenyl-ethyl}-1H-[1,2,4]triazole compounds and the N-oxides and the salts thereof for combating phytopathogenic fungi, and to the use and methods for combating phytopathogenic fungi and to seeds coated with at least one such compound. The invention also relates to processes for preparing these compounds and to compositions comprising at least one such compound.

Certain 1-{2-[2-chloro-4-(4-chloro-phenoxy)-phenyl]-2-alkenyloxy-ethyl}-1H-[1,2,4]triazole compounds of formula

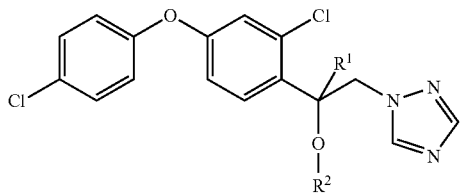

wherein $R^1$ is methyl, ethyl or n-propyl, and their use for controlling phytopathogenic fungi are known from EP 0 126 430 A2 and U.S. Pat. No. 4,940,720.

The compounds according to the present invention differ from those described in the abovementioned publication by the specific unsaturated alkyl group $R^1$ as defined herein. DE 3801233 is directed to microbiocides of the formula I

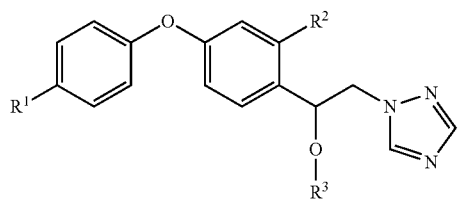

wherein $R^1$ is halogen and $R^2$ is halogen or methyl, $R^3$ is alkyl, haloalkyl, alkoxyalkyl, alkenyl, alkynyl or cyclopropyl. EP 0 440 950 A2 relates to halogenallyl-azolyl derivatives. DE 3801233 is directed to microbiocides of the formula I

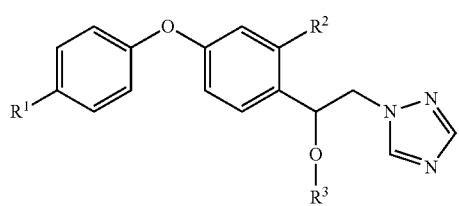

wherein $R^1$ is halogen and $R^2$ is halogen or methyl, $R^3$ is alkyl, haloalkyl, alkoxyalkyl, alkenyl, alkynyl or cyclopropyl. CN 101 225 074 relates to compounds of formula

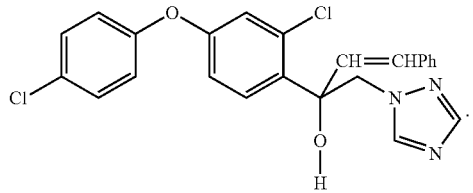

J. Agric. Food Chem., vol. 57, 2009, p 4954-4860 relates to the synthesis and fungicidal evaluation of certain 2-arylphenyl ether-3-(1H-1,2,4-triazol-1-yl)propan-2-ol derivatives. The compounds according to the present invention differ from those described in the abovementioned publications the combination of the particular 2-[2-halo-4-(4-halogen-phenoxy)-phenyl] group and the specific $R^1$ group as defined herein.

In many cases, in particular at low application rates, the fungicidal activity of the known fungicidal compounds is unsatisfactory. Based on this, it was an object of the present invention to provide compounds having improved activity and/or a broader activity spectrum against phytopathogenic harmful fungi.

This object is achieved by substituted 1-{2-[2-halo-4-(4-halogen-phenoxy)-phenyl]-2-alkoxy-2-alkynyl-ethyl}-1H-[1,2,4]triazole compounds having good fungicidal activity against phytopathogenic harmful fungi.

Accordingly, the present invention relates to the compounds of formula I:

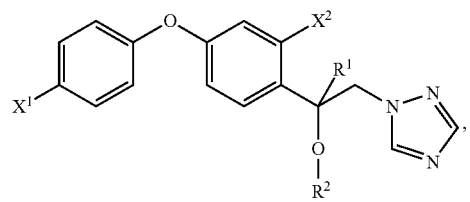

wherein:
$X^1$, $X^2$ independently of each other are selected from halogen;
$R^1$ is $C_2$-$C_6$-alkenyl or $C_2$-$C_6$-alkynyl;
$R^2$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;
wherein the aliphatic moieties of $R^1$ and/or $R^2$ may carry 1, 2, 3 or up to the maximum possible number of identical or different groups $R^a$ which independently of one another are selected from:
$R^a$ halogen, CN, nitro, phenyl, $C_1$-$C_4$-alkoxy and $C_1$-$C_4$-halogenalkoxy,
wherein the phenyl may be substituted by 1, 2, 3, 4 or 5 substituents selected from halogen, CN, nitro, $C_1$-$C_4$-alkyl, $C_1$-$C_4$-alkoxy, $C_1$-$C_4$-halogenalkyl and $C_1$-$C_4$-halogenalkoxy;
wherein the cycloalkyl and/or phenyl moieties of $R^2$ may carry 1, 2, 3, 4, 5 or up to the maximum number of identical or different groups $R^b$ which independently of one another are selected from:

$R^b$ halogen, CN, nitro, $C_1$-$C_4$-alkyl, $C_1$-$C_4$-alkoxy, $C_1$-$C_4$-halogenalkyl and $C_1$-$C_4$-halogenalkoxy;
and the N-oxides and the agriculturally acceptable salts thereof.

The present invention furthermore relates to to the use of these compounds for combating harmful fungi and seed coated with at least one such compound and also to compositions comprising at least one such compound of formula I.

The present invention furthermore relates to processes for preparing compounds of formula I and to intermediates such as compounds of formula Va, VI, VII, VIII, XI, XII and XIII.

The term "compounds I" refers to compounds of formula I. Likewise, this terminology applies to all sub-formulae, e. g. "compounds I.A" refers to compounds of formula I.A or "compounds XII" refers to compounds of formula XII, etc.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2) and by the synthesis routes shown in the following schemes and in the experimental part of this application.

In a first process, for example, halo-phenoles II wherein $X^1$ and $X^2$ as defined herein in, are reacted, in a first step, with derivatives IIIa

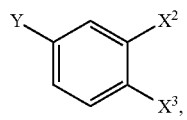

Y = F or Cl wherein $X^3$ stands for I or Br, in particular bromo derivatives III wherein Y is F or Cl, preferably in the presence of a base. Thereafter, the resulting compounds IVa, in particular IV (wherein $X^3$ is Br), are then transformed into Grignard reagents by the reaction with transmetallation reagents such as isopropylmagnesium halides and subsequently reacted with acetyl chloride preferably under anhydrous conditions and optionally in the presence of a catalyst such as CuCl, AlCl$_3$, LiCl and mixtures thereof, to obtain acetophenones V. These compounds V can be halogenated e.g. with bromine or chlorine preferably in an organic solvent such as diethyl ether, methyl tert.-butyl ether (MTBE), methanol or acetic acid. The resulting compounds VI, wherein "Hal" stands for "halogen" such as e.g. Br or Cl, can subsequently reacted with 1H-1,2,4-triazole preferably in the presence of a solvent such as tetrahydrofuran (THF), dimethylormamide (DMF), toluene and in the presence of a base such as potassium carbonate, sodium hydroxide or sodium hydride to obtain compounds VII. These triazole compounds VII are reacted with a Grignard reagent $R^1$-M wherein $R^1$ is as defined herein and M is MgBr, MgCl, Li or Na (e.g. phenylalkyl-MgBr or an organolithium reagent phenylalkyl-Li), preferably under anhydrous conditions to obtain compounds VIII. Optionally, a Lewis acid such as LaCl$_3$x2LiCl or MgBr$_2$xOEt$_2$ can be used. These compounds VIII are reacted with $R^2$-LG, wherein $R^1$ is as defined above and LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base, such as for example, NaH in a suitable solvent such as THF, to form compounds I. The preparation of compounds I can be illustrated by the following scheme:

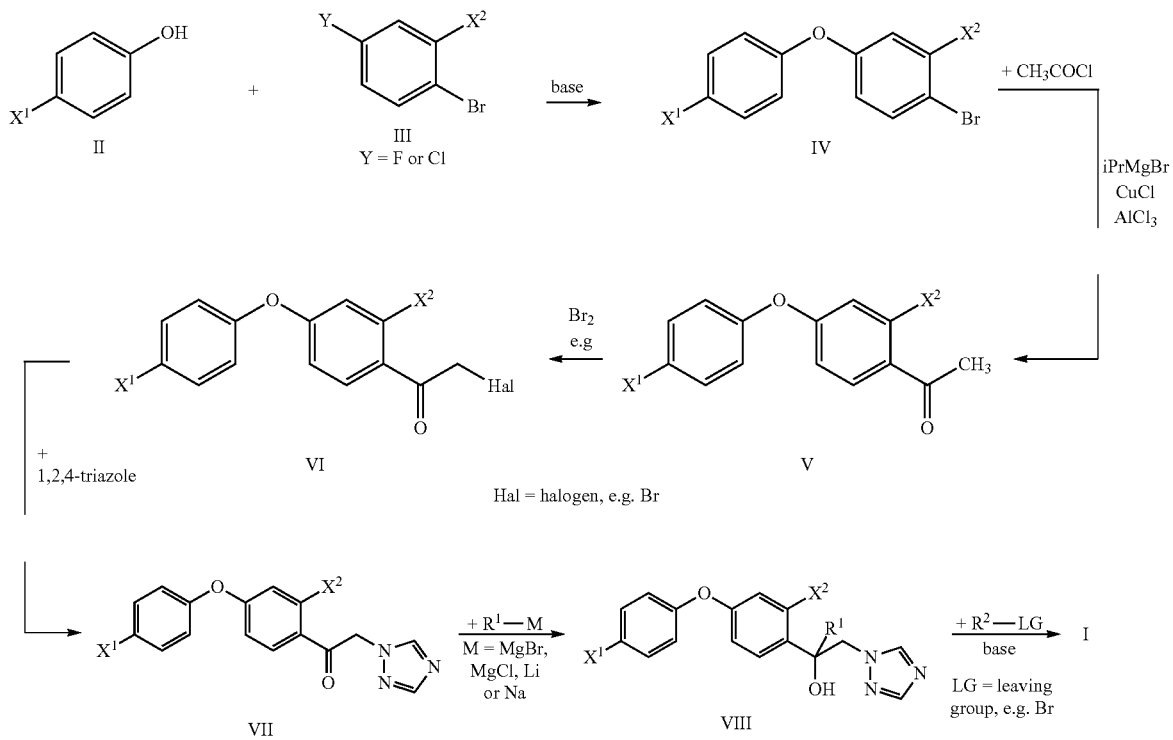

In a second process to obtain compounds I, derivatives IIIa, in particular bromo derivatives III, in a first step, are reacted with e.g. isopropylmagnesium bromide followed by an acyl chloride agent IX wherein $R^1$ is as defined herein (e.g. acetyl chloride) preferably under anhydrous conditions and optionally in the presence of a catalyst such as CuCl, AlCl$_3$, LiCl and mixtures thereof, to obtain compounds X. Alternatively, compounds IIIc

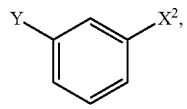

e.g. 1,3-dichlorobenzene of formula IIIb can be reacted with an acyl chloride agent IX wherein $R^1$ is as defined above (e.g. acetyl chloride) preferably in the presence of a catalyst such as AlCl$_3$. Then, ketones X are reacted with phenoles II preferably in the presence of a base to obtain compounds Va. Compounds Va may also be obtained in analogy to the first process described for compounds V.

Thereafter, intermediates Va are reacted with trimethylsulf(ox)onium halides preferably iodide preferably in the presence of a base such as sodium hydroxide. Thereafter, the epoxides XI are reacted with 1H-1,2,4-triazole preferably in the presence of a base such as potassium carbonate and preferably in the presence of an organic solvent such as DMF to obtain compounds VIII. These compounds VIII are reacted with $R^2$-LG, wherein $R^2$ is as defined above and LG represents a nucleophilically replaceable leaving group such as halogen, alkylsulfonyl, alkylsulfonyloxy and arylsulfonyloxy, preferably chloro, bromo or iodo, particularly preferably bromo, preferably in the presence of a base to form compounds I, which can subsequently be alkylated as described above. The preparation of compounds I can be illustrated by the following scheme:

under acidic conditions. Thereafter, the resulting compounds XII are reacted with halogenating agents or sulfonating agents such as PBr$_3$, PCl$_3$, mesyl chloride, tosyl chloride or thionyl chloride to obtain compounds XIII wherein LG is a nucleophilically replaceable leaving group such as halogen, alkylsulfonyl, alkylsulfonyloxy and arylsulfonyloxy, preferably chloro, bromo or iodo, particularly preferably bromo or alkylsulfonyl. Then compounds XIII are reacted with 1H-1,2,4-triazole to obtain compounds I. The preparation of compounds I can be illustrated by the following scheme:

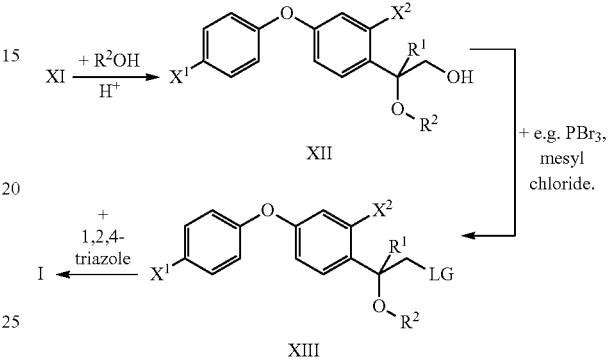

If individual compounds I cannot be obtained by the routes described above, they can be prepared by derivatization of other compounds I.

The N-oxides may be prepared from the compounds I according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc. 123(25), 5962-5973, 2001). The oxidation may lead to pure mono-N-oxides or to a mixture of different N-oxides, which can be separated by conventional methods such as chromatography.

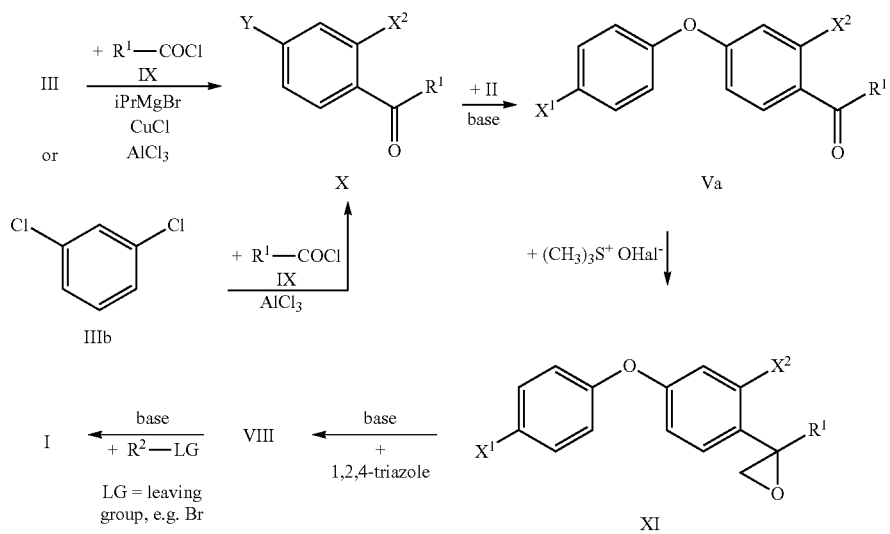

In a third process, the epoxide ring of intermediates XI which may be obtained according to the second process described herein is cleaved by reaction with alcohols $R^2$OH preferably If the synthesis yields mixtures of isomers, a separation is generally not necessarily required since in some cases the individual isomers can be interconverted during workup for use or during application (e. g. under the action of light, acids or bases). Such conversions may also take place after use, e. g. in the treatment of plants in the treated plant, or in the harmful fungus to be controlled.

In the following, the intermediate compounds are further described. A skilled person will readily understand that the preferences for the substituents given herein in connection with compounds I apply for the intermediates accordingly. Thereby, the substituents in each case have independently of each other or more preferably in combination the meanings as defined herein.

The present invention also relates to novel compounds of formula Va

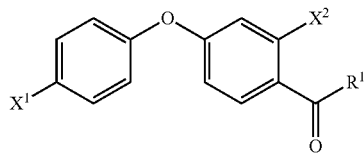

wherein the variables $R^1$, $X^1$, $X^2$ are as defined and preferably defined for formula I herein. In specific embodiments of compounds Va according to the present invention, the substituents $R^1$, $X^1$, $X^2$ are as defined in tables 1 to 148 and 148a to 148z and 148aa to 148jj and 149 to 296 and 296a to 296z and 296aa to 296jj for compounds I, wherein the substituents are specific embodiments independently of each other or in any combination.

A further embodiment of the present invention are novel compounds of formula VI:

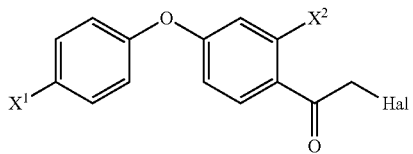

Wherein the variables $X^1$, $X^2$ are as defined and preferably defined for formula I herein, and wherein Hal stands for halogen, in particular Cl or Br. According to one preferred embodiment Hal in compounds VI stands for Br.

A further embodiment of the present invention are novel compounds of formula VII:

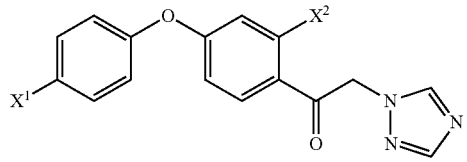

Wherein the variables $X^1$, $X^2$ are as defined and preferably defined for formula I herein. In specific embodiments of compounds VII according to the present invention, the substituents $X^1$, $X^2$ are as defined in tables 1 to 148 and 148a to 148z and 148aa to 148jj and 149 to 296 and 296a to 296z and 296aa to 296jj, wherein the substituents are specific embodiments independently of each other or in any combination.

A further embodiment of the present invention are novel compounds of formula VIII:

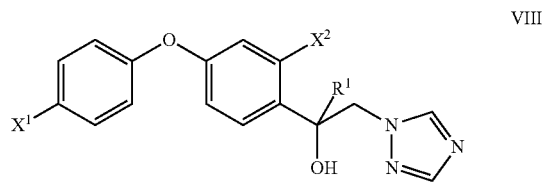

Wherein the variables $X^1$, $X^2$ and $R^1$ are as defined and preferably defined for formula I herein, with the exception 1) of compounds, wherein $X^1$ and $X^2$ are Cl and $R^1$ is CH=CH$_2$, CH=CHCH$_3$, CH$_2$CH=CH$_2$, C(CH$_3$)=CH$_2$, CH=CHCH$_2$CH$_3$, CH$_2$CH=CHCH$_3$, CH$_2$CH$_2$CH=CH$_2$, CH(CH=CH$_2$)$_2$, CH=C(CH$_3$)$_2$, CH=CHCH$_2$CH$_2$CH$_3$, CH=CHCH$_2$CH$_2$CH$_2$CH$_3$, CH=CHC(CH$_3$)$_3$, C≡CH, C≡CCH$_3$, C≡CCH$_2$CH$_3$, CH$_2$C≡CCH$_3$, CH$_2$CH$_2$C≡CH, CH(C≡CH)$_2$, C≡CCH$_2$CH$_2$CH$_3$, C≡CCH(CH$_3$)$_2$, C≡CCH$_2$CH$_2$CH$_2$CH$_3$, C≡CC(CH$_3$)$_3$, CH$_2$C(CH$_3$)=CH$_2$, CH$_2$C=CH, CH$_2$C≡CCH$_2$CH$_3$, CH$_2$C(Br)=CHBr or CH$_2$CCl=CHCl; and 2) of compounds, wherein $X^1$ and $X^2$ are Cl and $R^1$ is a moiety $AR^1$

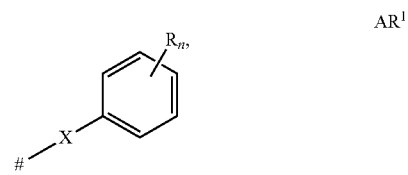

wherein:

# denotes the attachment point to formula VIII,

X is $C_2$-$C_4$-alkynediyl;

R is halogen, CN, nitro, $C_1$-$C_4$-alkyl, $C_1$-$C_4$-alkoxy, $C_1$-$C_4$-halogenalkyl or $C_1$-$C_4$-halogenalkoxy;

n is an integer and is 0, 1, 2, 3, 4 or 5; and 3) of compounds, wherein $X^1$ and $X^2$ are Cl and $R^1$ is CH=CHC$_6$H$_5$, CH=CH(4-Cl—C$_6$H$_4$), CH=CH(2,4-Cl$_2$—C$_6$H$_3$), CH=CH(2,6-Cl$_2$—C$_6$H$_3$), CH=CH(4-CH$_3$—C$_6$H$_4$), CH=CH(4-OCH$_3$—C$_6$H$_4$), CH=CH(3,4-Cl$_2$—C$_6$H$_3$), CH=CH(2-F—C$_6$H$_4$), CH=CH(4-NO$_2$—C$_6$H$_4$), CH=CH(2-NO$_2$—C$_6$H$_4$), CH=CH(2-Cl—C$_6$H$_4$), CH=CH(4-F—C$_6$H$_4$) or CH=CH(4-C$_2$H$_5$—C$_6$H$_4$).

According to one embodiment, the variables $X^1$, $X^2$ and $R^1$ are as defined and preferably defined for formula I herein, with the exception 1) of compounds, wherein $X^1$ and $X^2$ are Cl and $R^1$ is $C_2$-$C_6$-alkenyl or $C_2$-$C_6$-alkynyl; wherein $R^1$ are unsubstituted or carry 1, 2, 3 or 4 CN substituents; and 2) of compounds, wherein $X^1$ and $X^2$ are Cl and $R^1$ is CH$_2$C(Br)=CHBr or CH$_2$CCl=CHCl; and 3) of compounds, wherein $X^1$ and $X^2$ are Cl and $R^1$ is a moiety $AR^1$

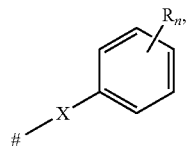

AR¹ wherein:
# denotes the attachment point to formula VIII,
X is $C_2$-$C_4$-alkynediyl;
R is halogen, CN, nitro, $C_1$-$C_4$-alkyl, $C_1$-$C_4$-alkoxy, $C_1$-$C_4$-halogenalkyl or $C_1$-$C_4$-halogenalkoxy;
n is an integer and is 0, 1, 2, 3, 4 or 5; and
4) of compounds, wherein $X^1$ and $X^2$ are Cl and $R^1$ is CH=CHC$_6$H$_5$, CH=CH(4-Cl—C$_6$H$_4$), CH=CH(2,4-Cl$_2$—C$_6$H$_3$), CH=CH(2,6-Cl$_2$—C$_6$H$_3$), CH=CH(4-CH$_3$—C$_6$H$_4$), CH=CH(4-OCH$_3$—C$_6$H$_4$), CH=CH(3,4-Cl$_2$—C$_6$H$_3$), CH=CH(2-F—C$_6$H$_4$), CH=CH(4-NO$_2$—C$_6$H$_4$), CH=CH(2-NO$_2$—C$_6$H$_4$), CH=CH(2-Cl—C$_6$H$_4$), CH=CH(4-F—C$_6$H$_4$) or CH=CH(4-C$_2$H$_5$—C$_6$H$_4$).

According to one embodiment, in compounds VIII $X^1$ and $X^2$ are not both Cl.

According to another embodiment, in compounds VIII $R^1$ is $C_2$-$C_6$-alkynyl, that is unsubstituted or that may carry 1, 2, 3 or up to the maximum possible number of identical or different groups $R^a$ which independently of one another are selected from halogen, CN, nitro, $C_1$-$C_2$-alkoxy and $C_1$-$C_2$-halogenalkoxy, taking into account the above disclaimer.

Compounds VIII are also suitable as fungicides as described herein for compounds of formula I. Specific preferred compounds VIII are the following C-1 to C-156, wherein each compound corresponds to one line of table C:

TABLE C

Compounds C-1 to C-156 of formula VIII

| line | $X^1$ | $X^2$ | $R^1$ |
|---|---|---|---|
| C-1 | Cl | F | CH=CH$_2$ |
| C-2 | F | Cl | CH=CH$_2$ |
| C-3 | F | F | CH=CH$_2$ |
| C-4 | Cl | F | CH$_2$CH=CH$_2$ |
| C-5 | F | Cl | CH$_2$CH=CH$_2$ |
| C-6 | F | F | CH$_2$CH=CH$_2$ |
| C-7 | Cl | F | CH$_2$CH=CHCH$_3$ |
| C-8 | F | Cl | CH$_2$CH=CHCH$_3$ |
| C-9 | F | F | CH$_2$CH=CHCH$_3$ |
| C-10 | Cl | Cl | CH$_2$CH=CHF |
| C-11 | Cl | F | CH$_2$CH=CHF |
| C-12 | F | Cl | CH$_2$CH=CHF |
| C-13 | F | F | CH$_2$CH=CHF |
| C-14 | Cl | Cl | CH$_2$CH=CHCl |
| C-15 | Cl | F | CH$_2$CH=CHCl |
| C-16 | F | Cl | CH$_2$CH=CHCl |
| C-17 | F | F | CH$_2$CH=CHCl |
| C-18 | Cl | F | CH$_2$C(CH$_3$)=CH$_2$ |
| C-19 | F | Cl | CH$_2$C(CH$_3$)=CH$_2$ |
| C-20 | F | F | CH$_2$C(CH$_3$)=CH$_2$ |
| C-21 | Cl | Cl | CH$_2$C(CH$_3$)=CHCH$_3$ |
| C-22 | Cl | F | CH$_2$C(CH$_3$)=CHCH$_3$ |
| C-23 | F | Cl | CH$_2$C(CH$_3$)=CHCH$_3$ |
| C-24 | F | F | CH$_2$C(CH$_3$)=CHCH$_3$ |
| C-25 | Cl | Cl | CH$_2$C(CH$_3$)=CHF |
| C-26 | Cl | F | CH$_2$C(CH$_3$)=CHF |
| C-27 | F | Cl | CH$_2$C(CH$_3$)=CHF |
| C-28 | F | F | CH$_2$C(CH$_3$)=CHF |
| C-29 | Cl | Cl | CH$_2$C(CH$_3$)=CHCl |
| C-30 | Cl | F | CH$_2$C(CH$_3$)=CHCl |
| C-31 | F | Cl | CH$_2$C(CH$_3$)=CHCl |
| C-32 | F | F | CH$_2$C(CH$_3$)=CHCl |
| C-33 | Cl | F | CH$_2$C≡CH |
| C-34 | F | Cl | CH$_2$C≡CH |
| C-35 | F | F | CH$_2$C≡CH |
| C-36 | Cl | F | CH$_2$C≡CCH$_3$ |
| C-37 | F | Cl | CH$_2$C≡CCH$_3$ |
| C-38 | F | F | CH$_2$C≡CCH$_3$ |
| C-39 | Cl | Cl | CH$_2$C≡CCF$_3$ |
| C-40 | Cl | F | CH$_2$C≡CCF$_3$ |
| C-41 | F | Cl | CH$_2$C≡CCF$_3$ |
| C-42 | F | F | CH$_2$C≡CCF$_3$ |
| C-43 | Cl | Cl | CH$_2$C≡CCl |
| C-44 | Cl | F | CH$_2$C≡CCl |
| C-45 | F | Cl | CH$_2$C≡CCl |
| C-46 | F | F | CH$_2$C≡CCl |
| C-47 | Cl | Cl | CH(CH$_3$)C≡CH |
| C-48 | Cl | F | CH(CH$_3$)C≡CH |
| C-49 | F | Cl | CH(CH$_3$)C≡CH |
| C-50 | F | F | CH(CH$_3$)C≡CH |
| C-51 | Cl | Cl | CH(CH$_3$)C≡CCl |
| C-52 | Cl | F | CH(CH$_3$)C≡CCl |
| C-53 | F | Cl | CH(CH$_3$)C≡CCl |
| C-54 | F | F | CH(CH$_3$)C≡CCl |
| C-55 | Cl | F | CH=CH—C$_6$H$_5$ |
| C-56 | F | Cl | CH=CH—C$_6$H$_5$ |
| C-57 | F | F | CH=CH—C$_6$H$_5$ |
| C-58 | Cl | Cl | C≡C—C$_6$H$_5$ |
| C-59 | Cl | F | C≡C—C$_6$H$_5$ |
| C-60 | F | Cl | C≡C—C$_6$H$_5$ |
| C-61 | F | F | C≡C—C$_6$H$_5$ |
| C-62 | Cl | Cl | CH$_2$—C≡C—C$_6$H$_5$ |
| C-63 | Cl | F | CH$_2$—C≡C—C$_6$H$_5$ |
| C-64 | F | Cl | CH$_2$—C≡C—C$_6$H$_5$ |
| C-65 | F | F | CH$_2$—C≡C—C$_6$H$_5$ |
| C-66 | Cl | F | CH=CHCH$_3$ |
| C-67 | F | Cl | CH=CHCH$_3$ |
| C-68 | F | F | CH=CHCH$_3$ |
| C-69 | Cl | F | C(CH$_3$)=CH$_2$ |
| C-70 | F | Cl | C(CH$_3$)=CH$_2$ |
| C-71 | F | F | C(CH$_3$)=CH$_2$ |
| C-72 | Cl | F | CH=CHCH$_2$CH$_3$ |
| C-73 | F | Cl | CH=CHCH$_2$CH$_3$ |
| C-74 | F | F | CH=CHCH$_2$CH$_3$ |
| C-75 | Cl | F | CH$_2$CH$_2$CH=CH$_2$ |
| C-76 | F | Cl | CH$_2$CH$_2$CH=CH$_2$ |
| C-77 | F | F | CH$_2$CH$_2$CH=CH$_2$ |
| C-78 | Cl | F | CH(CH=CH$_2$)$_2$ |
| C-79 | F | Cl | CH(CH=CH$_2$)$_2$ |
| C-80 | F | F | CH(CH=CH$_2$)$_2$ |
| C-81 | Cl | F | CH=C(CH$_3$)$_2$ |
| C-82 | F | Cl | CH=C(CH$_3$)$_2$ |
| C-83 | F | F | CH=C(CH$_3$)$_2$ |
| C-84 | Cl | F | CH=CHCH$_2$CH$_2$CH$_3$ |
| C-85 | F | Cl | CH=CHCH$_2$CH$_2$CH$_3$ |
| C-86 | F | F | CH=CHCH$_2$CH$_2$CH$_3$ |
| C-87 | Cl | F | CH=CHCH$_2$CH$_2$CH$_2$CH$_3$ |
| C-88 | F | Cl | CH=CHCH$_2$CH$_2$CH$_2$CH$_3$ |
| C-89 | F | F | CH=CHCH$_2$CH$_2$CH$_2$CH$_3$ |
| C-90 | Cl | F | CH=CHC(CH$_3$)$_3$ |
| C-91 | F | Cl | CH=CHC(CH$_3$)$_3$ |
| C-92 | F | F | CH=CHC(CH$_3$)$_3$ |
| C-93 | Cl | F | C≡CH |
| C-94 | F | Cl | C≡CH |
| C-95 | F | F | C≡CH |
| C-96 | Cl | F | C≡CCH$_3$ |
| C-97 | F | Cl | C≡CCH$_3$ |
| C-98 | F | F | C≡CCH$_3$ |
| C-99 | Cl | F | C≡CCH$_2$CH$_3$ |
| C-100 | F | Cl | C≡CCH$_2$CH$_3$ |
| C-101 | F | F | C≡CCH$_2$CH$_3$ |
| C-102 | Cl | F | CH$_2$CH$_2$C≡CH |
| C-103 | F | Cl | CH$_2$CH$_2$C≡CH |
| C-104 | F | F | CH$_2$CH$_2$C≡CH |
| C-105 | Cl | F | CH(C≡CH)$_2$ |
| C-106 | F | Cl | CH(C≡CH)$_2$ |
| C-107 | F | F | CH(C≡CH)$_2$ |

TABLE C-continued

Compounds C-1 to C-156 of formula VIII

| line | $X^1$ | $X^2$ | $R^1$ |
|---|---|---|---|
| C-108 | Cl | F | C≡CCH$_2$CH$_2$CH$_3$ |
| C-109 | F | Cl | C≡CCH$_2$CH$_2$CH$_3$ |
| C-110 | F | F | C≡CCH$_2$CH$_2$CH$_3$ |
| C-111 | Cl | F | C≡CCH(CH$_3$)$_2$ |
| C-112 | F | Cl | C≡CCH(CH$_3$)$_2$ |
| C-113 | F | F | C≡CCH(CH$_3$)$_2$ |
| C-114 | Cl | F | C≡CCH$_2$CH$_2$CH$_2$CH$_3$ |
| C-115 | F | Cl | C≡CCH$_2$CH$_2$CH$_2$CH$_3$ |
| C-116 | F | F | C≡CCH$_2$CH$_2$CH$_2$CH$_3$ |
| C-117 | Cl | F | C≡CC(CH$_3$)$_3$ |
| C-118 | F | Cl | C≡CC(CH$_3$)$_3$ |
| C-119 | F | F | C≡CC(CH$_3$)$_3$ |
| C-120 | Cl | F | CH$_2$C≡CCH$_2$CH$_3$ |
| C-121 | F | Cl | CH$_2$C≡CCH$_2$CH$_3$ |
| C-122 | F | F | CH$_2$C≡CCH$_2$CH$_3$ |
| C-123 | Cl | F | CH=CH-(4-F—C$_6$H$_4$) |
| C-124 | F | Cl | CH=CH-(4-F—C$_6$H$_4$) |
| C-125 | F | F | CH=CH-(4-F—C$_6$H$_4$) |
| C-126 | Cl | F | CH=CH-(4-Cl—C$_6$H$_4$) |
| C-127 | F | Cl | CH=CH-(4-Cl—C$_6$H$_4$) |
| C-128 | F | F | CH=CH-(4-Cl—C$_6$H$_4$) |
| C-129 | Cl | Cl | CH=CHCH$_2$OCH$_3$ |
| C-130 | Cl | F | CH=CHCH$_2$OCH$_3$ |
| C-131 | F | Cl | CH=CHCH$_2$OCH$_3$ |
| C-132 | F | F | CH=CHCH$_2$OCH$_3$ |
| C-133 | Cl | Cl | CH=CCl$_2$ |
| C-134 | Cl | F | CH=CCl$_2$ |
| C-135 | F | Cl | CH=CCl$_2$ |
| C-136 | F | F | CH=CCl$_2$ |
| C-137 | Cl | Cl | CH=CHOCH$_3$ |
| C-138 | Cl | F | CH=CHOCH$_3$ |
| C-139 | F | Cl | CH=CHOCH$_3$ |
| C-140 | F | F | CH=CHOCH$_3$ |
| C-141 | Cl | Cl | CH$_2$C≡CCH(CH$_3$)$_2$ |
| C-142 | Cl | F | CH$_2$C≡CCH(CH$_3$)$_2$ |
| C-143 | F | Cl | CH$_2$C≡CCH(CH$_3$)$_2$ |
| C-144 | F | F | CH$_2$C≡CCH(CH$_3$)$_2$ |
| C-145 | Cl | Cl | CH$_2$C≡CC(CH$_3$)$_3$ |
| C-146 | Cl | F | CH$_2$C≡CC(CH$_3$)$_3$ |
| C-147 | F | Cl | CH$_2$C≡CC(CH$_3$)$_3$ |
| C-148 | F | F | CH$_2$C≡CC(CH$_3$)$_3$ |
| C-149 | Cl | Cl | CH$_2$C≡CCH$_2$OCH$_3$ |
| C-150 | Cl | F | CH$_2$C≡CCH$_2$OCH$_3$ |
| C-151 | F | Cl | CH$_2$C≡CCH$_2$OCH$_3$ |
| C-152 | F | F | CH$_2$C≡CCH$_2$OCH$_3$ |
| C-153 | Cl | Cl | CH$_2$C(Cl)=CHCl |
| C-154 | Cl | F | CH$_2$C(Cl)=CHCl |
| C-155 | F | Cl | CH$_2$C(Cl)=CHCl |
| C-156 | F | F | CH$_2$C(Cl)=CHCl |

A further embodiment of the present invention are novel compounds of formula XI:

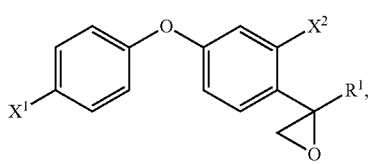

wherein the variables $X^1$, $X^2$ and $R^1$ are as defined and preferably defined for formula I herein, with the exception
1) of compounds, wherein $X^1$ and $X^2$ are Cl and $R^1$ is CH=CH$_2$, CH=CHCH$_3$, CH$_2$CH=CH$_2$, C(CH$_3$)=CH$_2$, CH=CHCH$_2$CH$_3$, CH$_2$CH=CHCH$_3$, CH$_2$CH$_2$CH=CH$_2$, CH(CH=CH$_2$)$_2$, CH=C(CH$_3$)$_2$, CH=CHCH$_2$CH$_2$CH$_3$, CH=CHCH(CH$_3$)$_2$, C≡CH, C≡CCH$_3$, C≡CCH$_2$CH$_3$, CH$_2$C≡CCH$_3$, CH$_2$CH$_2$C≡CH, CH(C≡CH)$_2$, C≡CCH$_2$CH$_2$CH$_3$, C≡CCH(CH$_3$)$_2$, C≡CCH$_2$CH$_2$CH$_2$CH$_3$, C≡CC(CH$_3$)$_3$, CH$_2$C(CH$_3$)=CH$_2$, CH$_2$C=CH, CH$_2$C≡CCH$_2$CH$_3$, CH$_2$C(Br)=CHBr or CH$_2$CCl=CHCl; and
2) of compounds, wherein $X^1$ and $X^2$ are Cl and $R^1$ is a moiety $AR^1$

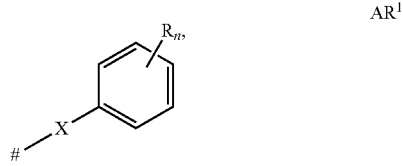

wherein:
# denotes the attachment point to formula VIII,
X is $C_2$-$C_4$-alkynediyl;
R is halogen, CN, nitro, $C_1$-$C_4$-alkyl, $C_1$-$C_4$-alkoxy, $C_1$-$C_4$-halogenalkyl or $C_1$-$C_4$-halogenalkoxy;
n is an integer and is 0, 1, 2, 3, 4 or 5; and
3) of compounds, wherein $X^1$ and $X^2$ are Cl and $R^1$ is CH=CHC$_6$H$_5$, CH=CH(4-Cl—C$_6$H$_4$), CH=CH(2,4-Cl$_2$—C$_6$H$_3$), CH=CH(2,6-Cl$_2$—C$_6$H$_3$), CH=CH(4-CH$_3$—C$_6$H$_4$), CH=CH(4-OCH$_3$—C$_6$H$_4$), CH=CH(3,4-Cl$_2$—C$_6$H$_3$), CH=CH(2-F—C$_6$H$_4$), CH=CH(4-NO$_2$—C$_6$H$_4$), CH=CH(2-NO$_2$—C$_6$H$_4$), CH=CH(2-Cl—C$_6$H$_4$), CH=CH(4-F—C$_6$H$_4$) or CH=CH(4-C$_2$H$_5$—C$_6$H$_4$).

According to one embodiment, the variables $X^1$, $X^2$ and $R^1$ are as defined and preferably defined for formula I herein, with the exception
1) of compounds, wherein $X^1$ and $X^2$ are Cl and $R^1$ is $C_2$-$C_6$-alkenyl or $C_2$-$C_6$-alkynyl; wherein $R^1$ are unsubstituted or carry 1, 2, 3 or 4 CN substituents; and
2) of compounds, wherein $X^1$ and $X^2$ are Cl and $R^1$ is CH$_2$C(Br)=CHBr or CH$_2$CCl=CHCl; and
3) of compounds, wherein $X^1$ and $X^2$ are Cl and $R^1$ is a moiety $AR^1$

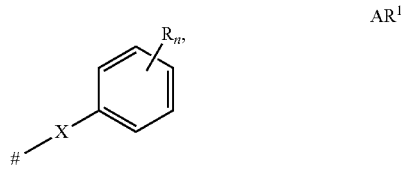

wherein:
# denotes the attachment point to formula VIII,
X is $C_2$-$C_4$-alkynediyl;
R is halogen, CN, nitro, $C_1$-$C_4$-alkyl, $C_1$-$C_4$-alkoxy, $C_1$-$C_4$-halogenalkyl or $C_1$-$C_4$-halogenalkoxy;
n is an integer and is 0, 1, 2, 3, 4 or 5; and
4) of compounds, wherein $X^1$ and $X^2$ are Cl and $R^1$ is CH=CHC$_6$H$_5$, CH=CH(4-Cl—C$_6$H$_4$), CH=CH(2,4-Cl$_2$—C$_6$H$_3$), CH=CH(2,6-Cl$_2$—C$_6$H$_3$), CH=CH(4-CH$_3$—C$_6$H$_4$), CH=CH(4-OCH$_3$—C$_6$H$_4$), CH=CH(3,4-Cl$_2$—C$_6$H$_3$), CH=CH(2-F—C$_6$H$_4$), CH=CH(4-NO$_2$—C$_6$H$_4$), CH=CH(2-NO$_2$—C$_6$H$_4$), CH=CH(2-Cl—C$_6$H$_4$), CH=CH(4-F—C$_6$H$_4$) or CH=CH(4-C$_2$H$_5$—C$_6$H$_4$).

According to one embodiment, in compounds VIII $X^1$ and $X^2$ are not both Cl.

In specific embodiments of compounds XI according to the present invention, the substituents $X^1$, $X^2$ and $R^1$ are as defined in tables 1 to 148 and 148a to 148z and 148aa to 148jj and 149 to 296 and 296a to 296z and 296aa to 296jj, wherein the substituents are specific embodiments independently of each other or in any combination.

Specific preferred compounds XI are the following D-1 to D-156, wherein each compound corresponds to one line of table D:

TABLE D

Compounds D-1 to D-156 of formula XI

| line | $X^1$ | $X^2$ | $R^1$ |
|---|---|---|---|
| D-1 | Cl | F | CH=CH$_2$ |
| D-2 | F | Cl | CH=CH$_2$ |
| D-3 | F | F | CH=CH$_2$ |
| D-4 | Cl | F | CH$_2$CH=CH$_2$ |
| D-5 | F | Cl | CH$_2$CH=CH$_2$ |
| D-6 | F | F | CH$_2$CH=CH$_2$ |
| D-7 | Cl | F | CH$_2$CH=CHCH$_3$ |
| D-8 | F | Cl | CH$_2$CH=CHCH$_3$ |
| D-9 | F | F | CH$_2$CH=CHCH$_3$ |
| D-10 | Cl | Cl | CH$_2$CH=CHF |
| D-11 | Cl | F | CH$_2$CH=CHF |
| D-12 | F | Cl | CH$_2$CH=CHF |
| D-13 | F | F | CH$_2$CH=CHF |
| D-14 | Cl | Cl | CH$_2$CH=CHCl |
| D-15 | Cl | F | CH$_2$CH=CHCl |
| D-16 | F | Cl | CH$_2$CH=CHCl |
| D-17 | F | F | CH$_2$CH=CHCl |
| D-18 | Cl | F | CH$_2$C(CH$_3$)=CH$_2$ |
| D-19 | F | Cl | CH$_2$C(CH$_3$)=CH$_2$ |
| D-20 | F | F | CH$_2$C(CH$_3$)=CH$_2$ |
| D-21 | Cl | Cl | CH$_2$C(CH$_3$)=CHCH$_3$ |
| D-22 | Cl | F | CH$_2$C(CH$_3$)=CHCH$_3$ |
| D-23 | F | Cl | CH$_2$C(CH$_3$)=CHCH$_3$ |
| D-24 | F | F | CH$_2$C(CH$_3$)=CHCH$_3$ |
| D-25 | Cl | Cl | CH$_2$C(CH$_3$)=CHF |
| D-26 | Cl | F | CH$_2$C(CH$_3$)=CHF |
| D-27 | F | Cl | CH$_2$C(CH$_3$)=CHF |
| D-28 | F | F | CH$_2$C(CH$_3$)=CHF |
| D-29 | Cl | Cl | CH$_2$C(CH$_3$)=CHCl |
| D-30 | Cl | F | CH$_2$C(CH$_3$)=CHCl |
| D-31 | F | Cl | CH$_2$C(CH$_3$)=CHCl |
| D-32 | F | F | CH$_2$C(CH$_3$)=CHCl |
| D-33 | Cl | F | CH$_2$C≡CH |
| D-34 | F | Cl | CH$_2$C≡CH |
| D-35 | F | F | CH$_2$C≡CH |
| D-36 | Cl | F | CH$_2$C≡CCH$_3$ |
| D-37 | F | Cl | CH$_2$C≡CCH$_3$ |
| D-38 | F | F | CH$_2$C≡CCH$_3$ |
| D-39 | Cl | Cl | CH$_2$C≡CCF$_3$ |
| D-40 | Cl | F | CH$_2$C≡CCF$_3$ |
| D-41 | F | Cl | CH$_2$C≡CCF$_3$ |
| D-42 | F | F | CH$_2$C≡CCF$_3$ |
| D-43 | Cl | Cl | CH$_2$C≡CCl |
| D-44 | Cl | F | CH$_2$C≡CCl |
| D-45 | F | Cl | CH$_2$C≡CCl |
| D-46 | F | F | CH$_2$C≡CCl |
| D-47 | Cl | Cl | CH(CH$_3$)C≡CH |
| D-48 | Cl | F | CH(CH$_3$)C≡CH |
| D-49 | F | Cl | CH(CH$_3$)C≡CH |
| D-50 | F | F | CH(CH$_3$)C≡CH |
| D-51 | Cl | Cl | CH(CH$_3$)C≡CCl |
| D-52 | Cl | F | CH(CH$_3$)C≡CCl |
| D-53 | F | Cl | CH(CH$_3$)C≡CCl |
| D-54 | F | F | CH(CH$_3$)C≡CCl |
| D-55 | Cl | Cl | CH=CH—C$_6$H$_5$ |
| D-56 | F | Cl | CH=CH—C$_6$H$_5$ |
| D-57 | F | F | CH=CH—C$_6$H$_5$ |
| D-58 | Cl | Cl | C≡C—C$_6$H$_5$ |
| D-59 | Cl | F | C≡C—C$_6$H$_5$ |
| D-60 | F | Cl | C≡C—C$_6$H$_5$ |
| D-61 | F | F | C≡C—C$_6$H$_5$ |
| D-62 | Cl | Cl | CH$_2$—C≡C—C$_6$H$_5$ |
| D-63 | Cl | F | CH$_2$—C≡C—C$_6$H$_5$ |
| D-64 | F | Cl | CH$_2$—C≡C—C$_6$H$_5$ |
| D-65 | F | F | CH$_2$—C≡C—C$_6$H$_5$ |
| D-66 | Cl | F | CH=CHCH$_3$ |
| D-67 | F | Cl | CH=CHCH$_3$ |
| D-68 | F | F | CH=CHCH$_3$ |
| D-69 | Cl | F | C(CH$_3$)=CH$_2$ |
| D-70 | F | Cl | C(CH$_3$)=CH$_2$ |
| D-71 | F | F | C(CH$_3$)=CH$_2$ |
| D-72 | Cl | F | CH=CHCH$_2$CH$_3$ |
| D-73 | F | Cl | CH=CHCH$_2$CH$_3$ |
| D-74 | F | F | CH=CHCH$_2$CH$_3$ |
| D-75 | Cl | F | CH$_2$CH$_2$CH=CH$_2$ |
| D-76 | F | Cl | CH$_2$CH$_2$CH=CH$_2$ |
| D-77 | F | F | CH$_2$CH$_2$CH=CH$_2$ |
| D-78 | Cl | F | CH(CH=CH$_2$)$_2$ |
| D-79 | F | Cl | CH(CH=CH$_2$)$_2$ |
| D-80 | F | F | CH(CH=CH$_2$)$_2$ |
| D-81 | Cl | F | CH=C(CH$_3$)$_2$ |
| D-82 | F | Cl | CH=C(CH$_3$)$_2$ |
| D-83 | F | F | CH=C(CH$_3$)$_2$ |
| D-84 | Cl | F | CH=CHCH$_2$CH$_2$CH$_3$ |
| D-85 | F | Cl | CH=CHCH$_2$CH$_2$CH$_3$ |
| D-86 | F | F | CH=CHCH$_2$CH$_2$CH$_3$ |
| D-87 | Cl | F | CH=CHCH$_2$CH$_2$CH$_2$CH$_3$ |
| D-88 | F | Cl | CH=CHCH$_2$CH$_2$CH$_2$CH$_3$ |
| D-89 | F | F | CH=CHCH$_2$CH$_2$CH$_2$CH$_3$ |
| D-90 | Cl | F | CH=CHC(CH$_3$)$_3$ |
| D-91 | F | Cl | CH=CHC(CH$_3$)$_3$ |
| D-92 | F | F | CH=CHC(CH$_3$)$_3$ |
| D-93 | Cl | F | C≡CH |
| D-94 | F | Cl | C≡CH |
| D-95 | F | F | C≡CH |
| D-96 | Cl | F | C≡CCH$_3$ |
| D-97 | F | Cl | C≡CCH$_3$ |
| D-98 | F | F | C≡CCH$_3$ |
| D-99 | Cl | F | C≡CCH$_2$CH$_3$ |
| D-100 | F | Cl | C≡CCH$_2$CH$_3$ |
| D-101 | F | F | C≡CCH$_2$CH$_3$ |
| D-102 | Cl | F | CH$_2$CH$_2$C≡CH |
| D-103 | F | Cl | CH$_2$CH$_2$C≡CH |
| D-104 | F | F | CH$_2$CH$_2$C≡CH |
| D-105 | Cl | F | CH(C≡CH)$_2$ |
| D-106 | F | Cl | CH(C≡CH)$_2$ |
| D-107 | F | F | CH(C≡CH)$_2$ |
| D-108 | Cl | F | C≡CCH$_2$CH$_2$CH$_3$ |
| D-109 | F | Cl | C≡CCH$_2$CH$_2$CH$_3$ |
| D-110 | F | F | C≡CCH$_2$CH$_2$CH$_3$ |
| D-111 | Cl | F | C≡CCH(CH$_3$)$_2$ |
| D-112 | F | Cl | C≡CCH(CH$_3$)$_2$ |
| D-113 | F | F | C≡CCH(CH$_3$)$_2$ |
| D-114 | Cl | F | C≡CCH$_2$CH$_2$CH$_2$CH$_3$ |
| D-115 | F | Cl | C≡CCH$_2$CH$_2$CH$_2$CH$_3$ |
| D-116 | F | F | C≡CCH$_2$CH$_2$CH$_2$CH$_3$ |
| D-117 | Cl | F | C≡CC(CH$_3$)$_3$ |
| D-118 | F | Cl | C≡CC(CH$_3$)$_3$ |
| D-119 | F | F | C≡CC(CH$_3$)$_3$ |
| D-120 | Cl | F | CH$_2$C≡CCH$_2$CH$_3$ |
| D-121 | F | Cl | CH$_2$C≡CCH$_2$CH$_3$ |
| D-122 | F | F | CH$_2$C≡CCH$_2$CH$_3$ |
| D-123 | Cl | F | CH=CH-(4-F—C$_6$H$_4$) |
| D-124 | F | Cl | CH=CH-(4-F—C$_6$H$_4$) |
| D-125 | F | F | CH=CH-(4-F—C$_6$H$_4$) |
| D-126 | Cl | F | CH=CH-(4-Cl—C$_6$H$_4$) |
| D-127 | F | Cl | CH=CH-(4-Cl—C$_6$H$_4$) |
| D-128 | F | F | CH=CH-(4-Cl—C$_6$H$_4$) |
| D-129 | Cl | Cl | CH=CHCH$_2$OCH$_3$ |
| D-130 | Cl | F | CH=CHCH$_2$OCH$_3$ |
| D-131 | F | Cl | CH=CHCH$_2$OCH$_3$ |
| D-132 | F | F | CH=CHCH$_2$OCH$_3$ |
| D-133 | Cl | Cl | CH=CCl$_2$ |
| D-134 | Cl | F | CH=CCl$_2$ |
| D-135 | F | Cl | CH=CCl$_2$ |
| D-136 | F | F | CH=CCl$_2$ |
| D-137 | Cl | Cl | CH=CHOCH$_3$ |
| D-138 | Cl | F | CH=CHOCH$_3$ |
| D-139 | F | Cl | CH=CHOCH$_3$ |
| D-140 | F | F | CH=CHOCH$_3$ |
| D-141 | Cl | Cl | CH$_2$C≡CCH(CH$_3$)$_2$ |
| D-142 | Cl | F | CH$_2$C≡CCH(CH$_3$)$_2$ |

TABLE D-continued

Compounds D-1 to D-156 of formula XI

| line | $X^1$ | $X^2$ | $R^1$ |
|---|---|---|---|
| D-143 | F | Cl | $CH_2C\equiv CCH(CH_3)_2$ |
| D-144 | F | F | $CH_2C\equiv CCH(CH_3)_2$ |
| D-145 | Cl | Cl | $CH_2C\equiv CC(CH_3)_3$ |
| D-146 | Cl | F | $CH_2C\equiv CC(CH_3)_3$ |
| D-147 | F | Cl | $CH_2C\equiv CC(CH_3)_3$ |
| D-148 | F | F | $CH_2C\equiv CC(CH_3)_3$ |
| D-149 | Cl | Cl | $CH_2C\equiv CCH_2OCH_3$ |
| D-150 | Cl | F | $CH_2C\equiv CCH_2OCH_3$ |
| D-151 | F | Cl | $CH_2C\equiv CCH_2OCH_3$ |
| D-152 | F | F | $CH_2C\equiv CCH_2OCH_3$ |
| D-153 | Cl | Cl | $CH_2C(Cl)=CHCl$ |
| D-154 | Cl | F | $CH_2C(Cl)=CHCl$ |
| D-155 | F | Cl | $CH_2C(Cl)=CHCl$ |
| D-156 | F | F | $CH_2C(Cl)=CHCl$ |

A further embodiment of the present invention are novel compounds of formula XII:

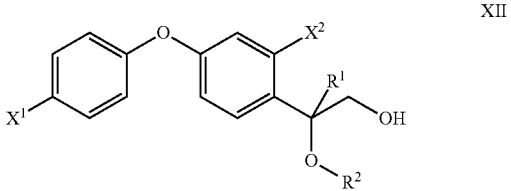

Wherein the variables $X^1$, $X^2$, $R^1$ and $R^2$ are as defined and preferably defined for formula I herein. In specific embodiments of compounds XII according to the present invention, the substituents $X^1$, $X^2$, $R^1$ and $R^2$ are as defined in tables 1 to 148 and 148a to 148z and 148aa to 148jj and 149 to 296 and 296a to 296z and 296aa to 296jj, wherein the substituents are specific embodiments independently of each other or in any combination.

A further embodiment of the present invention are novel compounds of formula XIII:

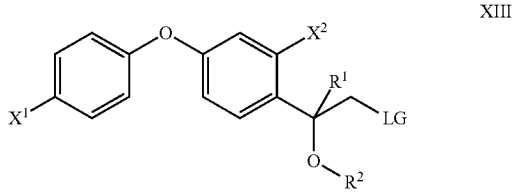

Wherein the variables $X^1$, $X^2$, $R^1$ and $R^2$ are as defined and preferably defined for formula I herein, wherein LG stands for a leaving group as defined above. In specific embodiments of compounds XIII according to the present invention, the substituents $X^1$, $X^2$, $R^1$ and $R^2$ are as defined in tables 1 to 148 and 148a to 148z and 148aa to 148jj and 149 to 296 and 296a to 296z and 296aa to 296jj, wherein the substituents are specific embodiments independently of each other or in any combination.

In the definitions of the variables given herein, collective terms are used which are generally representative for the substituents in question. The term "$C_n$-$C_m$" indicates the number of carbon atoms possible in each case in the substituent or substituent moiety in question.

The term "halogen" refers to fluorine, chlorine, bromine and iodine.

The term "$C_1$-$C_6$-alkyl" refers to a straight-chained or branched saturated hydrocarbon group having 1 to 6 carbon atoms, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. Likewise, the term "$C_2$-$C_4$-alkyl" refers to a straight-chained or branched alkyl group having 2 to 4 carbon atoms, such as ethyl, propyl(n-propyl), 1-methylethyl(iso-propoyl), butyl, 1-methylpropyl(sec.-butyl), 2-methylpropyl(iso-butyl), 1,1-dimethylethyl(tert.-butyl).

The term "$C_2$-$C_4$-alkenyl" refers to a straight-chain or branched unsaturated hydrocarbon radical having 2 to 4 carbon atoms and a double bond in any position, e.g. ethenyl, 1-propenyl, 2-propenyl(allyl), 1-methylethenyl, 1-butenyl, 2-butenyl, 3-butenyl, 1-methyl-1-propenyl, 2-methyl-1-propenyl, 1-methyl-2-propenyl, 2-methyl-2-propenyl. Likewise, the term "$C_2$-$C_6$-alkenyl" refers to a straight-chain or branched unsaturated hydrocarbon radical having 2 to 6 carbon atoms and a double bond in any position.

The term "$C_2$-$C_4$-alkynyl" refers to a straight-chain or branched unsaturated hydrocarbon radical having 2 to 4 carbon atoms and containing at least one triple bond, such as ethynyl, prop-1-ynyl, prop-2-ynyl(propargyl), but-1-ynyl, but-2-ynyl, but-3-ynyl, 1-methyl-prop-2-ynyl. Likewise, the term "$C_2$-$C_6$-alkynyl" refers to a straight-chain or branched unsaturated hydrocarbon radical having 2 to 6 carbon atoms and at least one triple bond.

The term "$C_1$-$C_4$-halogenalkyl" refers to a straight-chained or branched alkyl group having 1 to 4 carbon atoms, wherein some or all of the hydrogen atoms in these groups may be replaced by halogen atoms as mentioned above, for example chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, $CH_2$—$C_2F_5$, $CF_2$—$C_2F_5$, $CF(CF_3)_2$, 1-fluoromethyl-2-fluoroethyl, 1-(chloromethyl)-2-chloroethyl, 1-bromomethyl-2-bromoethyl, 4-fluorobutyl, 4-chlorobutyl, 4-bromobutyl or nonafluorobutyl, and the like.

The term "$C_3$-$C_8$-cycloalkyl" refers to monocyclic saturated hydrocarbon radicals having 3 to 8 carbon ring members, such as cyclopropyl, cyclobutyl, cyclopentyl, cyclohexyl, cycloheptyl or cyclooctyl.

The term "$C_3$-$C_8$-cycloalkyl-$C_1$-$C_4$-alkyl" refers to alkyl having 1 to 4 carbon atoms (as defined above), wherein one hydrogen atom of the alkyl radical is replaced by a cycloalkyl radical having 3 to 8 carbon atoms (as defined above).

The term "$C_1$-$C_4$-alkoxy" refers to a straight-chain or branched alkyl group having 1 to 4 carbon atoms which is bonded via an oxygen, at any position in the alkyl group, e.g. methoxy, ethoxy, n-propoxy, 1-methylethoxy, butoxy, 1-methyl¬ propoxy, 2-methylpropoxy or 1,1-dimethylethoxy.

The term "$C_1$-$C_4$-halogenalkoxy" refers to a $C_1$-$C_4$-alkoxy radical as defined above, wherein some or all of the hydrogen atoms in these groups may be replaced by halogen atoms as mentioned above, e.g., $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, $OC_2F_5$, 2-fluoropropoxy, 3-fluoropropoxy, 2,2-difluoropropoxy, 2,3-difluoro-propoxy, 2 chloropropoxy, 3-chloropropoxy, 2,3-dichloropropoxy, 2-bromopropoxy, 3 bromopropoxy, 3,3,3-trifluoropropoxy, 3,3,3-trichloropropoxy, $OCH_2$—$C_2F_5$, $OCF_2$—$C_2F_5$, 1-fluoromethyl-2-fluoroethoxy, 1-chloromethyl-2-chloroethoxy, 1-bromomethyl-2-bromo-ethoxy, 4-fluorobutoxy, 4-chlorobutoxy, 4-bromobutoxy or nonafluorobutoxy.

Agriculturally acceptable salts of compounds I encompass especially the salts of those cations or the acid addition salts of those acids whose cations and anions, respectively, have no adverse effect on the fungicidal action of the compounds I. Suitable cations are thus in particular the ions of the alkali metals, preferably sodium and potassium, of the alkaline earth metals, preferably calcium, magnesium and barium, of the transition metals, preferably manganese, copper, zinc and iron, and also the ammonium ion which, if desired, may carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formula I with an acid of the corresponding anion, preferably of hydrochloric acid, hydrobromic acid, sulfuric acid, phosphoric acid or nitric acid.

The compounds of formula I can be present in atropisomers arising from restricted rotation about a single bond of asymmetric groups. They also form part of the subject matter of the present invention.

Depending on the substitution pattern, the compounds of formula I and their N-oxides may have one or more centers of chirality, in which case they are present as pure enantiomers or pure diastereomers or as enantiomer or diastereomer mixtures. Both, the pure enantiomers or diastereomers and their mixtures are subject matter of the present invention.

In respect of the variables, the embodiments of the intermediates correspond to the embodiments of the compounds I.

Preference is given to those compounds I and where applicable also to compounds of all sub-formulae such as I.A provided herein and to the intermediates such as compounds VIII, XI, XII and XIII, wherein the substituents (such as $X^1$, $X^2$, $R^1$, $R^2$, $R^a$ and $R^b$) have independently of each other or more preferably in combination the following meanings:

According to the invention, $X^1$ and $X^2$ are independently selected from halogen.

One embodiment relates to compounds I, wherein $X^1$ is F or Cl, in particular Cl.

Another embodiment relates to compounds I, wherein $X^2$ is F or Cl, in particular Cl. According to the invention, $R^1$ is $C_2$-$C_6$-alkenyl or $C_2$-$C_6$-alkynyl. $R^1$ is unsubstituted or may carry 1, 2, 3 or up to the maximum possible number of identical or different groups $R^a$, which independently of one another are selected from halogen, CN, nitro, phenyl, $C_1$-$C_4$-alkoxy and $C_1$-$C_4$-halogenalkoxy, wherein the phenyl is unsubstituted or may carry 1, 2, 3, 4 or 5 substituents selected from halogen, CN, nitro, $C_1$-$C_4$-alkoxy, $C_1$-$C_4$-halogenalkyl and $C_1$-$C_4$-halogenalkoxy.

According to one embodiment, $R^1$ is $C_2$-$C_6$-alkenyl, wherein one specific embodiment thereof relates to compounds, wherein the alkenyl is unsubstituted and another embodiment relates to compounds, wherein the alkenyl is substituted by 1, 2 or 3 $R^a$, independently selected from halogen, CN, nitro, $C_1$-$C_2$-alkoxy and $C_1$-$C_2$-halogenalkoxy.

A further embodiment relates to compounds I, wherein $R^1$ is $C_2$-$C_6$-alkenyl, more preferably $C_2$-$C_4$-alkenyl, in particular selected from allyl and methylallyl, wherein the aforementioned groups may be substituted by $R^a$ as defined above, more preferably they may carry 1, 2 or 3 halogen substituents, in particular selected from Cl and F. According to one embodiment, $R^1$ is $CH_2$—$C(CH_3)$=$CH_2$, according to another embodiment, $R^1$ is $CH_2$—$CH$=$CH$—$CH_3$, wherein in these embodiments, the $R^1$ may carry 1, 2 or 3 $R^a$ as defined above, in particular, they may carry 1, 2 or 3 halogen substituents, in particular selected from Cl and F.

According to a further embodiment, $R^1$ is $C_2$-$C_6$-alkynyl. Specific embodiments are prop-1-ynyl, ethynyl, prop-2-ynyl and but-2-ynyl. According to one specific embodiment thereof relates to compounds, wherein the alkynyl is unsubstituted and another embodiment, relates to compounds, wherein the alkynyl is substituted by 1, 2 or 3 $R^a$, independently selected from halogen, CN, nitro, $C_1$-$C_2$-alkoxy and $C_1$-$C_2$-halogenalkoxy.

A further embodiment relates to compounds I, wherein $R^1$ is $C_2$-$C_6$-alkynyl, more preferably $C_2$-$C_6$-alk-1-ynyl, in particular selected from ethynyl, prop-1-ynyl, but-1-ynyl and 3-dimethyl-but-1-ynyl, wherein the aforementioned groups may be substituted by $R^a$ as defined above, more preferably they may carry 1, 2 or 3 halogen substituents, in particular selected from Cl and F.

A further embodiment relates to compounds I, wherein $R^1$ is $C_2$-$C_4$-alkynyl, more preferably propargyl, wherein the aforementioned groups may be substituted by $R^a$ as defined above. According to a further specific embodiment, $R^1$ is ethynyl.

A further embodiment relates to compounds I, wherein $R^1$ is unsubstituted.

According to a further embodiment, $R^1$ carries 1, 2 or 3 $R^a$, independently selected from F, Cl, CN, $C_1$-$C_2$-alkoxy and $C_1$-$C_2$-halogenalkoxy.

A further embodiment relates to compounds I, wherein $R^1$ carries one phenyl $R^a$ group, more preferably $R^1$ is phenylethenyl or phenylethynyl, wherein aforementioned phenyl moieties may be substituted by 1, 2 or 3 halogen substituents, in particular selected from Cl and F.

According to the invention, $R^2$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl; wherein the aliphatic moieties are unsubstituted or carry 1, 2, 3 or up to the maximum possible number of identical or different groups $R^a$ which independently of one another are selected from halogen, CN, nitro, phenyl, $C_1$-$C_4$-alkoxy and $C_1$-$C_4$-halogenalkoxy, wherein the phenyl may be substituted by 1, 2, 3, 4, or 5 substituents selected from halogen, CN, nitro, $C_1$-$C_4$-alkyl, $C_1$-$C_4$-alkoxy, $C_1$-$C_4$-halogenalkyl and $C_1$-$C_4$-halogenalkoxy; and wherein the cycloalkyl and/or phenyl moieties of $R^2$ may carry 1, 2, 3, 4, 5 or up to the maximum number of identical or different groups $R^b$ which independently of one another are selected from halogen, CN, nitro, $C_1$-$C_4$-alkyl, $C_1$-$C_4$-alkoxy, $C_1$-$C_4$-halogenalkyl and $C_1$-$C_4$-halogenalkoxy.

According to one embodiment, $R^2$ is $C_1$-$C_6$-alkyl, in particular $C_1$-$C_4$-alkyl. Specific embodiments relate to compounds, wherein $R^2$ is methyl, ethyl or isopropyl. According to one embodiment, the alkyl is unsubstituted, according to another embodiment, the alkyl carries 1, 2, 3, 4, 5 or 6, in particular 1, 2, 3 or 4, $R^a$, wherein $R^a$ is selected from F, Cl, Br, CN, $C_1$-$C_2$-alkoxy and $C_1$-$C_2$-halogenalkoxy.

According to a further embodiment, $R^2$ is $C_2$-$C_6$-alkenyl, in particular $C_2$-$C_4$-alkenyl. Specific embodiments relate to compounds, wherein $R^2$ is allyl. According to one embodiment, the alkenyl is unsubstituted, according to another embodiment, the alkenyl carries 1, 2, 3, 4, 5 or 6, in particular 1, 2, 3 or 4, $R^a$, wherein $R^a$ is selected from F, Cl, Br, CN, $C_1$-$C_2$-alkoxy and $C_1$-$C_2$-halogenalkoxy.

According to a further embodiment, $R^2$ is $C_2$-$C_6$-alkynyl, in particular $C_2$-$C_4$-alkynyl. Specific embodiments relate to compounds, wherein $R^2$ is propargyl. According to one embodiment, the alkynyl is unsubstituted, according to another embodiment, the alkynyl carries 1, 2, 3, 4, 5 or 6, in particular 1, 2, 3 or 4, $R^a$, wherein $R^a$ is selected from F, Cl, Br, CN, $C_1$-$C_2$-alkoxy and $C_1$-$C_2$-halogenalkoxy.

A further embodiment relates to compounds I, wherein $R^2$ is $C_1$-$C_4$-alkyl, $C_2$-$C_4$-alkenyl, $C_2$-$C_4$-alkynyl, cyclopropyl, cyclopropylmethyl, phenyl, benzyl, phenylethenyl or phenylethynyl, wherein the aforementioned groups may be substituted by $R^a$ and/or Rb as defined above, more preferably they carry 1, 2 or 3 halogen substituents, even more preferably $R^2$ is $C_1$-$C_2$-haloalkyl, in particular $R^2$ is $CF_3$.

A further embodiment relates to compounds I, wherein $R^2$ is $C_1$-$C_4$-alkyl, $C_2$-$C_4$-alkenyl, $C_2$-$C_4$-alkynyl, cyclopropyl, cyclopropylmethyl, phenyl, benzyl, phenylethenyl or phenylethynyl, more preferably from $C_1$-$C_4$-alkyl, in particular methyl.

According to a further embodiment, $R^2$ is $C_3$-$C_8$-cycloalkyl, in particular $C_3$-$C_6$-cycloalkyl. Specific embodiments relate to compounds, wherein $R^2$ is cyclopropyl. According to one embodiment, the cycloalkyl is unsubstituted, according to another embodiment, the cycloalkyl carries 1, 2, 3, 4, 5 or 6, in particular 1, 2, 3 or 4, Rb, wherein $R^b$ is selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy.

According to a further embodiment, $R^2$ is $C_3$-$C_8$-cycloalkyl-$C_1$-$C_4$-alkyl, in particular $C_3$-$C_6$-cycloalkyl-$C_1$-$C_4$-alkyl. Specific embodiments relate to compounds, wherein $R^2$ is cyclopropylmethyl. According to one embodiment, the cycloalkyl moiety is unsubstituted, according to another embodiment, the cycloalkyl moiety carries 1, 2, 3, 4, 5 or 6, in particular 1, 2, 3 or 4, Rb, wherein $R^b$ is selected from F, Cl, Br, CN, $C_1$-$C_2$-alkyl, $C_1$-$C_2$-alkoxy, $C_1$-$C_2$-halogenalkyl and $C_1$-$C_2$-halogenalkoxy. According to a further embodiment, the alkyl moiety is unsubstituted, according to another embodiment, the alkyl moiety carries 1, 2, 3, 4, 5 or 6, in particular 1, 2, 3 or 4, $R^a$, wherein $R^a$ is selected from F, Cl, Br, CN, $C_1$-$C_2$-alkoxy and $C_1$-$C_2$-halogenalkoxy.

A further embodiment relates to compounds I, wherein $R^2$ is $C_3$-$C_8$-cycloalkyl or $C_3$-$C_8$-cycloalkyl-$C_1$-$C_4$-alkyl, more preferably selected from cyclopropyl and cyclopropylmethyl, wherein the aforementioned groups may be substituted by $R^a$ and/or Rb as defined above.

A further embodiment relates to compounds I, wherein $R^2$ is unsubstituted.

A further embodiment relates to compounds, wherein $X^1$ and $X^2$ are both Cl and $R^1$ is ethynyl, which compounds are of formula I.B:

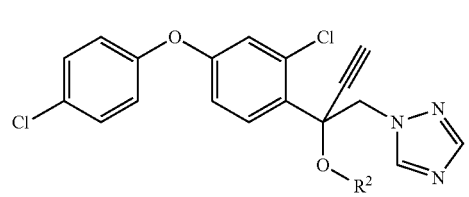

I.B

A further embodiment relates to compounds, wherein $X^1$ and $X^2$ are both Cl and $R^1$ is C≡CCH$_3$, which compounds are of formula I.C:

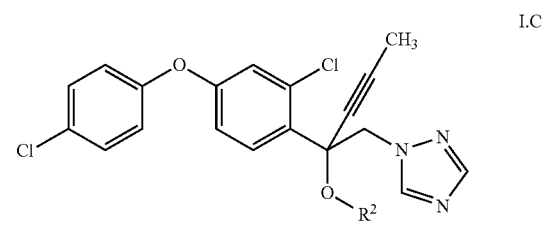

I.C

A further embodiment relates to compounds, wherein $X^1$ and $X^2$ are both Cl and $R^1$ is CH$_2$C≡CH, which compounds are of formula I.D:

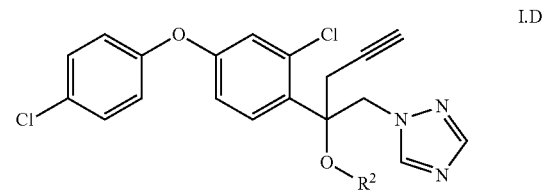

I.D

Particularly preferred embodiments of the invention relate to compounds I, wherein the combination of $X^1$, $X^2$ and $R^1$ (including $R^a$, $R^b$) is as defined in Table P below.

TABLE P

| line | $X^1$ | $X^2$ | $R^1$ |
|---|---|---|---|
| P-1 | Cl | Cl | —CH=CH$_2$ |
| P-2 | Cl | F | —CH=CH$_2$ |
| P-3 | F | Cl | —CH=CH$_2$ |
| P-4 | F | F | —CH=CH$_2$ |
| P-5 | Cl | Cl | —CH$_2$CH=CH$_2$ |
| P-6 | Cl | F | —CH$_2$CH=CH$_2$ |
| P-7 | F | Cl | —CH$_2$CH=CH$_2$ |
| P-8 | F | F | —CH$_2$CH=CH$_2$ |
| P-9 | Cl | Cl | —CH$_2$CH=CHCH$_3$ |
| P-10 | Cl | F | —CH$_2$CH=CHCH$_3$ |
| P-11 | F | Cl | —CH$_2$CH=CHCH$_3$ |
| P-12 | F | F | —CH$_2$CH=CHCH$_3$ |
| P-13 | Cl | Cl | —CH$_2$CH=CHF |
| P-14 | Cl | F | —CH$_2$CH=CHF |
| P-15 | F | Cl | —CH$_2$CH=CHF |
| P-16 | F | F | —CH$_2$CH=CHF |
| P-17 | Cl | Cl | —CH$_2$CH=CHCl |
| P-18 | Cl | F | —CH$_2$CH=CHCl |
| P-19 | F | Cl | —CH$_2$CH=CHCl |
| P-20 | F | F | —CH$_2$CH=CHCl |
| P-21 | Cl | Cl | —CH$_2$C(CH$_3$)=CH$_2$ |
| P-22 | Cl | F | —CH$_2$C(CH$_3$)=CH$_2$ |
| P-23 | F | Cl | —CH$_2$C(CH$_3$)=CH$_2$ |
| P-24 | F | F | —CH$_2$C(CH$_3$)=CH$_2$ |
| P-25 | Cl | Cl | —CH$_2$C(CH$_3$)=CHCH$_3$ |

TABLE P-continued

| line | $X^1$ | $X^2$ | $R^1$ |
|---|---|---|---|
| P-26 | Cl | F | —CH$_2$C(CH$_3$)=CHCH$_3$ |
| P-27 | F | Cl | —CH$_2$C(CH$_3$)=CHCH$_3$ |
| P-28 | F | F | —CH$_2$C(CH$_3$)=CHCH$_3$ |
| P-29 | Cl | Cl | —CH$_2$C(CH$_3$)=CHF |
| P-30 | Cl | F | —CH$_2$C(CH$_3$)=CHF |
| P-31 | F | Cl | —CH$_2$C(CH$_3$)=CHF |
| P-32 | F | F | —CH$_2$C(CH$_3$)=CHF |
| P-33 | Cl | Cl | —CH$_2$C(CH$_3$)=CHCl |
| P-34 | Cl | F | —CH$_2$C(CH$_3$)=CHCl |
| P-35 | F | Cl | —CH$_2$C(CH$_3$)=CHCl |
| P-36 | F | F | —CH$_2$C(CH$_3$)=CHCl |
| P-37 | Cl | Cl | —CH$_2$C≡CH |
| P-38 | Cl | F | —CH$_2$C≡CH |
| P-39 | F | Cl | —CH$_2$C≡CH |
| P-40 | F | F | —CH$_2$C≡CH |
| P-41 | Cl | Cl | —CH$_2$C≡CCH$_3$ |
| P-42 | Cl | F | —CH$_2$C≡CCH$_3$ |
| P-43 | F | Cl | —CH$_2$C≡CCH$_3$ |
| P-44 | F | F | —CH$_2$C≡CCH$_3$ |
| P-45 | Cl | Cl | —CH$_2$C≡CCF$_3$ |
| P-46 | Cl | F | —CH$_2$C≡CCF$_3$ |
| P-47 | F | Cl | —CH$_2$C≡CCF$_3$ |
| P-48 | F | F | —CH$_2$C≡CCF$_3$ |
| P-49 | Cl | Cl | —CH$_2$C≡CCl |
| P-50 | Cl | F | —CH$_2$C≡CCl |
| P-51 | F | Cl | —CH$_2$C≡CCl |
| P-52 | F | F | —CH$_2$C≡CCl |
| P-53 | Cl | Cl | —CH(CH$_3$)C≡CH |
| P-54 | Cl | F | —CH(CH$_3$)C≡CH |
| P-55 | F | Cl | —CH(CH$_3$)C≡CH |
| P-56 | F | F | —CH(CH$_3$)C≡CH |
| P-57 | Cl | Cl | —CH(CH$_3$)C≡CCl |
| P-58 | Cl | F | —CH(CH$_3$)C≡CCl |
| P-59 | F | Cl | —CH(CH$_3$)C≡CCl |
| P-60 | F | F | —CH(CH$_3$)C≡CCl |
| P-61 | Cl | Cl | —CH=CH—C$_6$H$_5$ |
| P-62 | Cl | F | —CH=CH—C$_6$H$_5$ |
| P-63 | F | Cl | —CH=CH—C$_6$H$_5$ |
| P-64 | F | F | —CH=CH—C$_6$H$_5$ |
| P-65 | Cl | Cl | —C≡C—C$_6$H$_5$ |
| P-66 | Cl | F | —C≡C—C$_6$H$_5$ |
| P-67 | F | Cl | —C≡C—C$_6$H$_5$ |
| P-68 | F | F | —C≡C—C$_6$H$_5$ |
| P-69 | Cl | Cl | —CH$_2$—C≡C—C$_6$H$_5$ |
| P-70 | Cl | F | —CH$_2$—C≡C—C$_6$H$_5$ |
| P-71 | F | Cl | —CH$_2$—C≡C—C$_6$H$_5$ |
| P-72 | F | F | —CH$_2$—C≡C—C$_6$H$_5$ |
| P-73 | Cl | Cl | CH=CHCH$_3$ |
| P-74 | Cl | F | CH=CHCH$_3$ |
| P-75 | F | Cl | CH=CHCH$_3$ |
| P-76 | F | F | CH=CHCH$_3$ |
| P-77 | Cl | Cl | C(CH$_3$)=CH$_2$ |
| P-78 | Cl | F | C(CH$_3$)=CH$_2$ |
| P-79 | F | Cl | C(CH$_3$)=CH$_2$ |
| P-80 | F | F | C(CH$_3$)=CH$_2$ |
| P-81 | Cl | Cl | CH=CHCH$_2$CH$_3$ |
| P-82 | Cl | F | CH=CHCH$_2$CH$_3$ |
| P-83 | F | Cl | CH=CHCH$_2$CH$_3$ |
| P-84 | F | F | CH=CHCH$_2$CH$_3$ |
| P-85 | Cl | Cl | CH$_2$CH$_2$CH=CH$_2$ |
| P-86 | Cl | F | CH$_2$CH$_2$CH=CH$_2$ |
| P-87 | F | Cl | CH$_2$CH$_2$CH=CH$_2$ |
| P-88 | F | F | CH$_2$CH$_2$CH=CH$_2$ |
| P-89 | Cl | Cl | CH(CH=CH$_2$)$_2$ |
| P-90 | Cl | F | CH(CH=CH$_2$)$_2$ |
| P-91 | F | Cl | CH(CH=CH$_2$)$_2$ |
| P-92 | F | F | CH(CH=CH$_2$)$_2$ |
| P-93 | Cl | Cl | CH=C(CH$_3$)$_2$ |
| P-94 | Cl | F | CH=C(CH$_3$)$_2$ |
| P-95 | F | Cl | CH=C(CH$_3$)$_2$ |
| P-96 | F | F | CH=C(CH$_3$)$_2$ |
| P-97 | Cl | Cl | CH=CHCH$_2$CH$_2$CH$_3$ |
| P-98 | Cl | F | CH=CHCH$_2$CH$_2$CH$_3$ |
| P-99 | F | Cl | CH=CHCH$_2$CH$_2$CH$_3$ |
| P-100 | F | F | CH=CHCH$_2$CH$_2$CH$_3$ |
| P-101 | Cl | Cl | CH=CHCH$_2$CH$_2$CH$_2$CH$_3$ |
| P-102 | Cl | F | CH=CHCH$_2$CH$_2$CH$_2$CH$_3$ |
| P-103 | F | Cl | CH=CHCH$_2$CH$_2$CH$_2$CH$_3$ |
| P-104 | F | F | CH=CHCH$_2$CH$_2$CH$_2$CH$_3$ |
| P-105 | Cl | Cl | CH=CHC(CH$_3$)$_3$ |
| P-106 | Cl | F | CH=CHC(CH$_3$)$_3$ |
| P-107 | F | Cl | CH=CHC(CH$_3$)$_3$ |
| P-108 | F | F | CH=CHC(CH$_3$)$_3$ |
| P-109 | Cl | Cl | C≡CH |
| P-110 | Cl | F | C≡CH |
| P-111 | F | Cl | C≡CH |
| P-112 | F | F | C≡CH |
| P-113 | Cl | Cl | C≡CCH$_3$ |
| P-114 | Cl | F | C≡CCH$_3$ |
| P-115 | F | Cl | C≡CCH$_3$ |
| P-116 | F | F | C≡CCH$_3$ |
| P-117 | Cl | Cl | C≡CCH$_2$CH$_3$ |
| P-118 | Cl | F | C≡CCH$_2$CH$_3$ |
| P-119 | F | Cl | C≡CCH$_2$CH$_3$ |
| P-120 | F | F | C≡CCH$_2$CH$_3$ |
| P-121 | Cl | Cl | CH$_2$CH$_2$C≡CH |
| P-122 | Cl | F | CH$_2$CH$_2$C≡CH |
| P-123 | F | Cl | CH$_2$CH$_2$C≡CH |
| P-124 | F | F | CH$_2$CH$_2$C≡CH |
| P-125 | Cl | Cl | CH(C≡CH)$_2$ |
| P-126 | Cl | F | CH(C≡CH)$_2$ |
| P-127 | F | Cl | CH(C≡CH)$_2$ |
| P-128 | F | F | CH(C≡CH)$_2$ |
| P-129 | Cl | Cl | C≡CCH$_2$CH$_2$CH$_3$ |
| P-130 | Cl | F | C≡CCH$_2$CH$_2$CH$_3$ |
| P-131 | F | Cl | C≡CCH$_2$CH$_2$CH$_3$ |
| P-132 | F | F | C≡CCH$_2$CH$_2$CH$_3$ |
| P-133 | Cl | Cl | C≡CCH(CH$_3$)$_2$ |
| P-134 | Cl | F | C≡CCH(CH$_3$)$_2$ |
| P-135 | F | Cl | C≡CCH(CH$_3$)$_2$ |
| P-136 | F | F | C≡CCH(CH$_3$)$_2$ |
| P-137 | Cl | Cl | C≡CCH$_2$CH$_2$CH$_2$CH$_3$ |
| P-138 | Cl | F | C≡CCH$_2$CH$_2$CH$_2$CH$_3$ |
| P-139 | F | Cl | C≡CCH$_2$CH$_2$CH$_2$CH$_3$ |
| P-140 | F | F | C≡CCH$_2$CH$_2$CH$_2$CH$_3$ |
| P-141 | Cl | Cl | C≡CC(CH$_3$)$_3$ |
| P-142 | Cl | F | C≡CC(CH$_3$)$_3$ |
| P-143 | F | Cl | C≡CC(CH$_3$)$_3$ |
| P-144 | F | F | C≡CC(CH$_3$)$_3$ |
| P-145 | Cl | Cl | CH$_2$C≡CCH$_2$CH$_3$ |
| P-146 | Cl | F | CH$_2$C≡CCH$_2$CH$_3$ |
| P-147 | F | Cl | CH$_2$C≡CCH$_2$CH$_3$ |
| P-148 | F | F | CH$_2$C≡CCH$_2$CH$_3$ |
| P-149 | Cl | Cl | CH=CH-(4-F—C$_6$H$_4$) |
| P-150 | Cl | F | CH=CH-(4-F—C$_6$H$_4$) |
| P-151 | F | Cl | CH=CH-(4-F—C$_6$H$_4$) |
| P-152 | F | F | CH=CH-(4-F—C$_6$H$_4$) |
| P-153 | Cl | Cl | CH=CH-(4-Cl—C$_6$H$_4$) |
| P-154 | Cl | F | CH=CH-(4-Cl—C$_6$H$_4$) |
| P-155 | F | Cl | CH=CH-(4-Cl—C$_6$H$_4$) |
| P-156 | F | F | CH=CH-(4-Cl—C$_6$H$_4$) |
| P-157 | Cl | Cl | CH=CHCH$_2$OCH$_3$ |
| P-158 | Cl | F | CH=CHCH$_2$OCH$_3$ |
| P-159 | F | Cl | CH=CHCH$_2$OCH$_3$ |
| P-160 | F | F | CH=CHCH$_2$OCH$_3$ |
| P-161 | Cl | Cl | CH=CCl$_2$ |
| P-162 | Cl | F | CH=CCl$_2$ |
| P-163 | F | Cl | CH=CCl$_2$ |
| P-164 | F | F | CH=CCl$_2$ |
| P-165 | Cl | Cl | CH=CHOCH$_3$ |
| P-166 | Cl | F | CH=CHOCH$_3$ |
| P-167 | F | Cl | CH=CHOCH$_3$ |
| P-168 | F | F | CH=CHOCH$_3$ |
| P-169 | Cl | Cl | CH$_2$C≡CCH(CH$_3$)$_2$ |
| P-170 | Cl | F | CH$_2$C≡CCH(CH$_3$)$_2$ |
| P-171 | F | Cl | CH$_2$C≡CCH(CH$_3$)$_2$ |
| P-172 | F | F | CH$_2$C≡CCH(CH$_3$)$_2$ |
| P-173 | Cl | Cl | CH$_2$C≡CC(CH$_3$)$_3$ |
| P-174 | Cl | F | CH$_2$C≡CC(CH$_3$)$_3$ |
| P-175 | F | Cl | CH$_2$C≡CC(CH$_3$)$_3$ |
| P-176 | F | F | CH$_2$C≡CC(CH$_3$)$_3$ |
| P-177 | Cl | Cl | CH$_2$C≡CCH$_2$OCH$_3$ |
| P-178 | Cl | F | CH$_2$C≡CCH$_2$OCH$_3$ |
| P-179 | F | Cl | CH$_2$C≡CCH$_2$OCH$_3$ |
| P-180 | F | F | CH$_2$C≡CCH$_2$OCH$_3$ |
| P-181 | Cl | Cl | CH$_2$C(Cl)=CHCl |

TABLE P-continued

| line | $X^1$ | $X^2$ | $R^1$ |
|---|---|---|---|
| P-182 | Cl | F | $CH_2C(Cl)=CHCl$ |
| P-183 | F | Cl | $CH_2C(Cl)=CHCl$ |
| P-184 | F | F | $CH_2C(Cl)=CHCl$ |

A skilled person will readily understand that the preferences given in connection with compounds I apply for formula VIII, XI and XII etc. as defined above.

With respect to their use, particular preference is given to compounds 1 to 5520 and 1a to 5520a of formula I compiled in Tables 1 to 148 and 148a to 148z and 148aa to 148jj and 149 to 296 and 296a to 296z and 296aa to 296jj below. The groups mentioned in the Tables for a substituent are furthermore, independently of the combination wherein they are mentioned, a particularly preferred embodiment of the substituent in question.

Table 1: Compounds 1 to 30 of formula I, wherein $X^1$, $X^2$ and $R^1$ are defined as in line P-1 of table P and the meaning of $R^2$ for each individual compound corresponds in each case to one line of table A.
Table 2: Compounds 31 to 60 of formula I, wherein $X^1$, $X^2$ and $R^1$ are defined as in line P-2 of table P and the meaning of $R^2$ for each individual compound corresponds in each case to one line of table A.
Table 3: Compounds 61 to 90 of formula I, wherein $X^1$, $X^2$ and $R^1$ are defined as in line P-3 of table P and the meaning of $R^2$ for each individual compound corresponds in each case to one line of table A.
Table 4: Compounds 91 to 120 of formula I, wherein $X^1$, $X^2$ and $R^1$ are defined as in line P-4 of table P and the meaning of $R^2$ for each individual compound corresponds in each case to one line of table A.
Table 5: Compounds 121 to 150 of formula I, wherein $X^1$, $X^2$ and $R^1$ are defined as in line P-5 of table P and the meaning of $R^2$ for each individual compound corresponds in each case to one line of table A.
Table 6: Compounds 151 to 180 of formula I, wherein $X^1$, $X^2$ and $R^1$ are defined as in line P-6 of table P and the meaning of $R^2$ for each individual compound corresponds in each case to one line of table A.
Table 7: Compounds 181 to 210 of formula I, wherein $X^1$, $X^2$ and $R^1$ are defined as in line P-7 of table P and the meaning of $R^2$ for each individual compound corresponds in each case to one line of table A.
Table 8: Compounds 211 to 240 of formula I, wherein $X^1$, $X^2$ and $R^1$ are defined as in line P-8 of table P and the meaning of $R^2$ for each individual compound corresponds in each case to one line of table A.
Table 9: Compounds 241 to 270 of formula I, wherein $X^1$, $X^2$ and $R^1$ are defined as in line P-9 of table P and the meaning of $R^2$ for each individual compound corresponds in each case to one line of table A.
Table 10: Compounds 271 to 300 of formula I, wherein $X^1$, $X^2$ and $R^1$ are defined as in line P-10 of table P and the meaning of $R^2$ for each individual compound corresponds in each case to one line of table A.
Table 11: Compounds 301 to 330 of formula I, wherein $X^1$, $X^2$ and $R^1$ are defined as in line P-11 of table P and the meaning of $R^2$ for each individual compound corresponds in each case to one line of table A.
Table 12: Compounds 331 to 360 of formula I, wherein $X^1$, $X^2$ and $R^1$ are defined as in line P-12 of table P and the meaning of $R^2$ for each individual compound corresponds in each case to one line of table A.
Table 13: Compounds 361 to 390 of formula I, wherein $X^1$, $X^2$ and $R^1$ are defined as in line P-13 of table P and the meaning of $R^2$ for each individual compound corresponds in each case to one line of table A.
Table 14: Compounds 391 to 420 of formula I, wherein $X^1$, $X^2$ and $R^1$ are defined as in line P-14 of table P and the meaning of $R^2$ for each individual compound corresponds in each case to one line of table A.
Table 15: Compounds 421 to 450 of formula I, wherein $X^1$, $X^2$ and $R^1$ are defined as in line P-15 of table P and the meaning of $R^2$ for each individual compound corresponds in each case to one line of table A.
Table 16: Compounds 451 to 480 of formula I, wherein $X^1$, $X^2$ and $R^1$ are defined as in line P-16 of table P and the meaning of $R^2$ for each individual compound corresponds in each case to one line of table A.
Table 17: Compounds 481 to 510 of formula I, wherein $X^1$, $X^2$ and $R^1$ are defined as in line P-17 of table P and the meaning of $R^2$ for each individual compound corresponds in each case to one line of table A.
Table 18: Compounds 511 to 540 of formula I, wherein $X^1$, $X^2$ and $R^1$ are defined as in line P-18 of table P and the meaning of $R^2$ for each individual compound corresponds in each case to one line of table A.
Table 19: Compounds 541 to 570 of formula I, wherein $X^1$, $X^2$ and $R^1$ are defined as in line P-19 of table P and the meaning of $R^2$ for each individual compound corresponds in each case to one line of table A.
Table 20: Compounds 571 to 600 of formula I, wherein $X^1$, $X^2$ and $R^1$ are defined as in line P-20 of table P and the meaning of $R^2$ for each individual compound corresponds in each case to one line of table A.
Table 21: Compounds 601 to 630 of formula I, wherein $X^1$, $X^2$ and $R^1$ are defined as in line P-21 of table P and the meaning of $R^2$ for each individual compound corresponds in each case to one line of table A.
Table 22: Compounds 631 to 660 of formula I, wherein $X^1$, $X^2$ and $R^1$ are defined as in line P-22 of table P and the meaning of $R^2$ for each individual compound corresponds in each case to one line of table A.
Table 23: Compounds 661 to 690 of formula I, wherein $X^1$, $X^2$ and $R^1$ are defined as in line P-23 of table P and the meaning of $R^2$ for each individual compound corresponds in each case to one line of table A.
Table 24: Compounds 691 to 720 of formula I, wherein $X^1$, $X^2$ and $R^1$ are defined as in line P-24 of table P and the meaning of $R^2$ for each individual compound corresponds in each case to one line of table A.
Table 25: Compounds 721 to 750 of formula I, wherein $X^1$, $X^2$ and $R^1$ are defined as in line P-25 of table P and the meaning of $R^2$ for each individual compound corresponds in each case to one line of table A.
Table 26: Compounds 751 to 780 of formula I, wherein $X^1$, $X^2$ and $R^1$ are defined as in line P-26 of table P and the meaning of $R^2$ for each individual compound corresponds in each case to one line of table A.
Table 27: Compounds 781 to 810 of formula I, wherein $X^1$, $X^2$ and $R^1$ are defined as in line P-27 of table P and the meaning of $R^2$ for each individual compound corresponds in each case to one line of table A.
Table 28: Compounds 811 to 840 of formula I, wherein $X^1$, $X^2$ and $R^1$ are defined as in line P-28 of table P and the meaning of $R^2$ for each individual compound corresponds in each case to one line of table A.
Table 29: Compounds 841 to 870 of formula I, wherein $X^1$, $X^2$ and $R^1$ are defined as in line P-29 of table P and the meaning of $R^2$ for each individual compound corresponds in each case to one line of table A.

Table 30: Compounds 871 to 900 of formula I, wherein $X^1$, $X^2$ and $R^1$ are defined as in line P-30 of table P and the meaning of $R^2$ for each individual compound corresponds in each case to one line of table A.

Table 31: Compounds 901 to 930 of formula I, wherein $X^1$, $X^2$ and $R^1$ are defined as in line P-31 of table P and the meaning of $R^2$ for each individual compound corresponds in each case to one line of table A.

Table 32: Compounds 931 to 960 of formula I, wherein $X^1$, $X^2$ and $R^1$ are defined as in line P-32 of table P and the meaning of $R^2$ for each individual compound corresponds in each case to one line of table A.

Table 33: Compounds 961 to 990 of formula I, wherein $X^1$, $X^2$ and $R^1$ are defined as in line P-33 of table P and the meaning of $R^2$ for each individual compound corresponds in each case to one line of table A.

Table 34: Compounds 991 to 1020 of formula I, wherein $X^1$, $X^2$ and $R^1$ are defined as in line P-34 of table P and the meaning of $R^2$ for each individual compound corresponds in each case to one line of table A.

Table 35: Compounds 1021 to 1050 of formula I, wherein $X^1$, $X^2$ and $R^1$ are defined as in line P-35 of table P and the meaning of $R^2$ for each individual compound corresponds in each case to one line of table A.

Table 36: Compounds 1051 to 1080 of formula I, wherein $X^1$, $X^2$ and $R^1$ are defined as in line P-36 of table P and the meaning of $R^2$ for each individual compound corresponds in each case to one line of table A.

Table 37: Compounds 1081 to 1110 of formula I, wherein $X^1$, $X^2$ and $R^1$ are defined as in line P-37 of table P and the meaning of $R^2$ for each individual compound corresponds in each case to one line of table A.

Table 38: Compounds 1111 to 1140 of formula I, wherein $X^1$, $X^2$ and $R^1$ are defined as in line P-38 of table P and the meaning of $R^2$ for each individual compound corresponds in each case to one line of table A.

Table 39: Compounds 1141 to 1170 of formula I, wherein $X^1$, $X^2$ and $R^1$ are defined as in line P-39 of table P and the meaning of $R^2$ for each individual compound corresponds in each case to one line of table A.

Table 40: Compounds 1171 to 1200 of formula I, wherein $X^1$, $X^2$ and $R^1$ are defined as in line P-40 of table P and the meaning of $R^2$ for each individual compound corresponds in each case to one line of table A.

Table 41: Compounds 1201 to 1230 of formula I, wherein $X^1$, $X^2$ and $R^1$ are defined as in line P-41 of table P and the meaning of $R^2$ for each individual compound corresponds in each case to one line of table A.

Table 42: Compounds 1231 to 1260 of formula I, wherein $X^1$, $X^2$ and $R^1$ are defined as in line P-42 of table P and the meaning of $R^2$ for each individual compound corresponds in each case to one line of table A.

Table 43: Compounds 1261 to 1290 of formula I, wherein $X^1$, $X^2$ and $R^1$ are defined as in line P-43 of table P and the meaning of $R^2$ for each individual compound corresponds in each case to one line of table A.

Table 44: Compounds 1291 to 1320 of formula I, wherein $X^1$, $X^2$ and $R^1$ are defined as in line P-44 of table P and the meaning of $R^2$ for each individual compound corresponds in each case to one line of table A.

Table 45: Compounds 1321 to 1350 of formula I, wherein $X^1$, $X^2$ and $R^1$ are defined as in line P-45 of table P and the meaning of $R^2$ for each individual compound corresponds in each case to one line of table A.

Table 46: Compounds 1351 to 1380 of formula I, wherein $X^1$, $X^2$ and $R^1$ are defined as in line P-46 of table P and the meaning of $R^2$ for each individual compound corresponds in each case to one line of table A.

Table 47: Compounds 1381 to 1410 of formula I, wherein $X^1$, $X^2$ and $R^1$ are defined as in line P-47 of table P and the meaning of $R^2$ for each individual compound corresponds in each case to one line of table A.

Table 48: Compounds 1411 to 1440 of formula I, wherein $X^1$, $X^2$ and $R^1$ are defined as in line P-48 of table P and the meaning of $R^2$ for each individual compound corresponds in each case to one line of table A.

Table 49: Compounds 1441 to 1470 of formula I, wherein $X^1$, $X^2$ and $R^1$ are defined as in line P-49 of table P and the meaning of $R^2$ for each individual compound corresponds in each case to one line of table A.

Table 50: Compounds 1471 to 1500 of formula I, wherein $X^1$, $X^2$ and $R^1$ are defined as in line P-50 of table P and the meaning of $R^2$ for each individual compound corresponds in each case to one line of table A.

Table 51: Compounds 1501 to 1530 of formula I, wherein $X^1$, $X^2$ and $R^1$ are defined as in line P-51 of table P and the meaning of $R^2$ for each individual compound corresponds in each case to one line of table A.

Table 52: Compounds 1531 to 1560 of formula I, wherein $X^1$, $X^2$ and $R^1$ are defined as in line P-52 of table P and the meaning of $R^2$ for each individual compound corresponds in each case to one line of table A.

Table 53: Compounds 1561 to 1590 of formula I, wherein $X^1$, $X^2$ and $R^1$ are defined as in line P-53 of table P and the meaning of $R^2$ for each individual compound corresponds in each case to one line of table A.

Table 54: Compounds 1591 to 1620 of formula I, wherein $X^1$, $X^2$ and $R^1$ are defined as in line P-54 of table P and the meaning of $R^2$ for each individual compound corresponds in each case to one line of table A.

Table 55: Compounds 1621 to 1650 of formula I, wherein $X^1$, $X^2$ and $R^1$ are defined as in line P-55 of table P and the meaning of $R^2$ for each individual compound corresponds in each case to one line of table A.

Table 56: Compounds 1651 to 1680 of formula I, wherein $X^1$, $X^2$ and $R^1$ are defined as in line P-56 of table P and the meaning of $R^2$ for each individual compound corresponds in each case to one line of table A.

Table 57: Compounds 1681 to 1710 of formula I, wherein $X^1$, $X^2$ and $R^1$ are defined as in line P-57 of table P and the meaning of $R^2$ for each individual compound corresponds in each case to one line of table A.

Table 58: Compounds 1711 to 1740 of formula I, wherein $X^1$, $X^2$ and $R^1$ are defined as in line P-58 of table P and the meaning of $R^2$ for each individual compound corresponds in each case to one line of table A.

Table 59: Compounds 1741 to 1770 of formula I, wherein $X^1$, $X^2$ and $R^1$ are defined as in line P-59 of table P and the meaning of $R^2$ for each individual compound corresponds in each case to one line of table A.

Table 60: Compounds 1771 to 1800 of formula I, wherein $X^1$, $X^2$ and $R^1$ are defined as in line P-60 of table P and the meaning of $R^2$ for each individual compound corresponds in each case to one line of table A.

Table 61: Compounds 1801 to 1830 of formula I, wherein $X^1$, $X^2$ and $R^1$ are defined as in line P-61 of table P and the meaning of $R^2$ for each individual compound corresponds in each case to one line of table A.

Table 62: Compounds 1831 to 1860 of formula I, wherein $X^1$, $X^2$ and $R^1$ are defined as in line P-62 of table P and the meaning of $R^2$ for each individual compound corresponds in each case to one line of table A.

Table 63: Compounds 1861 to 1890 of formula I, wherein $X^1$, $X^2$ and $R^1$ are defined as in line P-63 of table P and the meaning of $R^2$ for each individual compound corresponds in each case to one line of table A.

Table 64: Compounds 1891 to 1920 of formula I, wherein $X^1$, $X^2$ and $R^1$ are defined as in line P-64 of table P and the meaning of $R^2$ for each individual compound corresponds in each case to one line of table A.

Table 65: Compounds 1921 to 1950 of formula I, wherein $X^1$, $X^2$ and $R^1$ are defined as in line P-65 of table P and the meaning of $R^2$ for each individual compound corresponds in each case to one line of table A.

Table 66: Compounds 1951 to 1980 of formula I, wherein $X^1$, $X^2$ and $R^1$ are defined as in line P-66 of table P and the meaning of $R^2$ for each individual compound corresponds in each case to one line of table A.

Table 67: Compounds 1981 to 2010 of formula I, wherein $X^1$, $X^2$ and $R^1$ are defined as in line P-67 of table P and the meaning of $R^2$ for each individual compound corresponds in each case to one line of table A.

Table 68: Compounds 2011 to 2040 of formula I, wherein $X^1$, $X^2$ and $R^1$ are defined as in line P-68 of table P and the meaning of $R^2$ for each individual compound corresponds in each case to one line of table A.

Table 69: Compounds 2041 to 2070 of formula I, wherein $X^1$, $X^2$ and $R^1$ are defined as in line P-69 of table P and the meaning of $R^2$ for each individual compound corresponds in each case to one line of table A.

Table 70: Compounds 2071 to 2100 of formula I, wherein $X^1$, $X^2$ and $R^1$ are defined as in line P-70 of table P and the meaning of $R^2$ for each individual compound corresponds in each case to one line of table A.

Table 71: Compounds 2101 to 2130 of formula I, wherein $X^1$, $X^2$ and $R^1$ are defined as in line P-71 of table P and the meaning of $R^2$ for each individual compound corresponds in each case to one line of table A.

Table 72: Compounds 2131 to 2160 of formula I, wherein $X^1$, $X^2$ and $R^1$ are defined as in line P-72 of table P and the meaning of $R^2$ for each individual compound corresponds in each case to one line of table A.

Table 73: Compounds 2161 to 2190 of formula I, wherein $X^1$, $X^2$ and $R^1$ are defined as in line P-73 of table P and the meaning of $R^2$ for each individual compound corresponds in each case to one line of table A.

Table 74: Compounds 2191 to 2220 of formula I, wherein $X^1$, $X^2$ and $R^1$ are defined as in line P-74 of table P and the meaning of $R^2$ for each individual compound corresponds in each case to one line of table A.

Table 75: Compounds 2221 to 2250 of formula I, wherein $X^1$, $X^2$ and $R^1$ are defined as in line P-75 of table P and the meaning of $R^2$ for each individual compound corresponds in each case to one line of table A.

Table 76: Compounds 2251 to 2280 of formula I, wherein $X^1$, $X^2$ and $R^1$ are defined as in line P-76 of table P and the meaning of $R^2$ for each individual compound corresponds in each case to one line of table A.

Table 77: Compounds 2281 to 2310 of formula I, wherein $X^1$, $X^2$ and $R^1$ are defined as in line P-77 of table P and the meaning of $R^2$ for each individual compound corresponds in each case to one line of table A.

Table 78: Compounds 2311 to 2340 of formula I, wherein $X^1$, $X^2$ and $R^1$ are defined as in line P-78 of table P and the meaning of $R^2$ for each individual compound corresponds in each case to one line of table A.

Table 79: Compounds 2341 to 2370 of formula I, wherein $X^1$, $X^2$ and $R^1$ are defined as in line P-79 of table P and the meaning of $R^2$ for each individual compound corresponds in each case to one line of table A.

Table 80: Compounds 2371 to 2400 of formula I, wherein $X^1$, $X^2$ and $R^1$ are defined as in line P-80 of table P and the meaning of $R^2$ for each individual compound corresponds in each case to one line of table A.

Table 81: Compounds 2401 to 2430 of formula I, wherein $X^1$, $X^2$ and $R^1$ are defined as in line P-81 of table P and the meaning of $R^2$ for each individual compound corresponds in each case to one line of table A.

Table 82: Compounds 2431 to 2460 of formula I, wherein $X^1$, $X^2$ and $R^1$ are defined as in line P-82 of table P and the meaning of $R^2$ for each individual compound corresponds in each case to one line of table A.

Table 83: Compounds 2461 to 2490 of formula I, wherein $X^1$, $X^2$ and $R^1$ are defined as in line P-83 of table P and the meaning of $R^2$ for each individual compound corresponds in each case to one line of table A.

Table 84: Compounds 2491 to 2520 of formula I, wherein $X^1$, $X^2$ and $R^1$ are defined as in line P-84 of table P and the meaning of $R^2$ for each individual compound corresponds in each case to one line of table A.

Table 85: Compounds 2521 to 2550 of formula I, wherein $X^1$, $X^2$ and $R^1$ are defined as in line P-85 of table P and the meaning of $R^2$ for each individual compound corresponds in each case to one line of table A.

Table 86: Compounds 2551 to 2580 of formula I, wherein $X^1$, $X^2$ and $R^1$ are defined as in line P-86 of table P and the meaning of $R^2$ for each individual compound corresponds in each case to one line of table A.

Table 87: Compounds 2581 to 2610 of formula I, wherein $X^1$, $X^2$ and $R^1$ are defined as in line P-87 of table P and the meaning of $R^2$ for each individual compound corresponds in each case to one line of table A.

Table 88: Compounds 2611 to 2640 of formula I, wherein $X^1$, $X^2$ and $R^1$ are defined as in line P-88 of table P and the meaning of $R^2$ for each individual compound corresponds in each case to one line of table A.

Table 89: Compounds 2641 to 2670 of formula I, wherein $X^1$, $X^2$ and $R^1$ are defined as in line P-89 of table P and the meaning of $R^2$ for each individual compound corresponds in each case to one line of table A.

Table 90: Compounds 2671 to 2700 of formula I, wherein $X^1$, $X^2$ and $R^1$ are defined as in line P-90 of table P and the meaning of $R^2$ for each individual compound corresponds in each case to one line of table A.

Table 91: Compounds 2701 to 2730 of formula I, wherein $X^1$, $X^2$ and $R^1$ are defined as in line P-91 of table P and the meaning of $R^2$ for each individual compound corresponds in each case to one line of table A.

Table 92: Compounds 2731 to 2760 of formula I, wherein $X^1$, $X^2$ and $R^1$ are defined as in line P-92 of table P and the meaning of $R^2$ for each individual compound corresponds in each case to one line of table A.

Table 93: Compounds 2761 to 2790 of formula I, wherein $X^1$, $X^2$ and $R^1$ are defined as in line P-93 of table P and the meaning of $R^2$ for each individual compound corresponds in each case to one line of table A.

Table 94: Compounds 2791 to 2820 of formula I, wherein $X^1$, $X^2$ and $R^1$ are defined as in line P-94 of table P and the meaning of $R^2$ for each individual compound corresponds in each case to one line of table A.

Table 95: Compounds 2821 to 2850 of formula I, wherein $X^1$, $X^2$ and $R^1$ are defined as in line P-95 of table P and the meaning of $R^2$ for each individual compound corresponds in each case to one line of table A.

Table 96: Compounds 2851 to 2880 of formula I, wherein $X^1$, $X^2$ and $R^1$ are defined as in line P-96 of table P and the meaning of $R^2$ for each individual compound corresponds in each case to one line of table A.

Table 97: Compounds 2881 to 2910 of formula I, wherein $X^1$, $X^2$ and $R^1$ are defined as in line P-97 of table P and the meaning of $R^2$ for each individual compound corresponds in each case to one line of table A.

Table 98: Compounds 2911 to 2940 of formula I, wherein $X^1$, $X^2$ and $R^1$ are defined as in line P-98 of table P and the meaning of $R^2$ for each individual compound corresponds in each case to one line of table A.

Table 99: Compounds 2941 to 2970 of formula I, wherein $X^1$, $X^2$ and $R^1$ are defined as in line P-99 of table P and the meaning of $R^2$ for each individual compound corresponds in each case to one line of table A.

Table 100: Compounds 2971 to 3000 of formula I, wherein $X^1$, $X^2$ and $R^1$ are defined as in line P-100 of table P and the meaning of $R^2$ for each individual compound corresponds in each case to one line of table A.

Table 101: Compounds 3001 to 3030 of formula I, wherein $X^1$, $X^2$ and $R^1$ are defined as in line P-101 of table P and the meaning of $R^2$ for each individual compound corresponds in each case to one line of table A.

Table 102: Compounds 3031 to 3060 of formula I, wherein $X^1$, $X^2$ and $R^1$ are defined as in line P-102 of table P and the meaning of $R^2$ for each individual compound corresponds in each case to one line of table A.

Table 103: Compounds 3061 to 3090 of formula I, wherein $X^1$, $X^2$ and $R^1$ are defined as in line P-103 of table P and the meaning of $R^2$ for each individual compound corresponds in each case to one line of table A.

Table 104: Compounds 3091 to 3120 of formula I, wherein $X^1$, $X^2$ and $R^1$ are defined as in line P-104 of table P and the meaning of $R^2$ for each individual compound corresponds in each case to one line of table A.

Table 105: Compounds 3121 to 3150 of formula I, wherein $X^1$, $X^2$ and $R^1$ are defined as in line P-105 of table P and the meaning of $R^2$ for each individual compound corresponds in each case to one line of table A.

Table 106: Compounds 3151 to 3180 of formula I, wherein $X^1$, $X^2$ and $R^1$ are defined as in line P-106 of table P and the meaning of $R^2$ for each individual compound corresponds in each case to one line of table A.

Table 107: Compounds 3181 to 3210 of formula I, wherein $X^1$, $X^2$ and $R^1$ are defined as in line P-107 of table P and the meaning of $R^2$ for each individual compound corresponds in each case to one line of table A.

Table 108: Compounds 3211 to 3240 of formula I, wherein $X^1$, $X^2$ and $R^1$ are defined as in line P-108 of table P and the meaning of $R^2$ for each individual compound corresponds in each case to one line of table A.

Table 109: Compounds 3241 to 3270 of formula I, wherein $X^1$, $X^2$ and $R^1$ are defined as in line P-109 of table P and the meaning of $R^2$ for each individual compound corresponds in each case to one line of table A.

Table 110: Compounds 3271 to 3300 of formula I, wherein $X^1$, $X^2$ and $R^1$ are defined as in line P-110 of table P and the meaning of $R^2$ for each individual compound corresponds in each case to one line of table A.

Table 111: Compounds 3301 to 3330 of formula I, wherein $X^1$, $X^2$ and $R^1$ are defined as in line P-111 of table P and the meaning of $R^2$ for each individual compound corresponds in each case to one line of table A.

Table 112: Compounds 3331 to 3360 of formula I, wherein $X^1$, $X^2$ and $R^1$ are defined as in line P-112 of table P and the meaning of $R^2$ for each individual compound corresponds in each case to one line of table A.

Table 113: Compounds 3361 to 3390 of formula I, wherein $X^1$, $X^2$ and $R^1$ are defined as in line P-113 of table P and the meaning of $R^2$ for each individual compound corresponds in each case to one line of table A.

Table 114: Compounds 3391 to 3420 of formula I, wherein $X^1$, $X^2$ and $R^1$ are defined as in line P-114 of table P and the meaning of $R^2$ for each individual compound corresponds in each case to one line of table A.

Table 115: Compounds 3421 to 3450 of formula I, wherein $X^1$, $X^2$ and $R^1$ are defined as in line P-115 of table P and the meaning of $R^2$ for each individual compound corresponds in each case to one line of table A.

Table 116: Compounds 3451 to 3480 of formula I, wherein $X^1$, $X^2$ and $R^1$ are defined as in line P-116 of table P and the meaning of $R^2$ for each individual compound corresponds in each case to one line of table A.

Table 117: Compounds 3481 to 3510 of formula I, wherein $X^1$, $X^2$ and $R^1$ are defined as in line P-117 of table P and the meaning of $R^2$ for each individual compound corresponds in each case to one line of table A.

Table 118: Compounds 3510 to 3540 of formula I, wherein $X^1$, $X^2$ and $R^1$ are defined as in line P-118 of table P and the meaning of $R^2$ for each individual compound corresponds in each case to one line of table A.

Table 119: Compounds 3541 to 3570 of formula I, wherein $X^1$, $X^2$ and $R^1$ are defined as in line P-119 of table P and the meaning of $R^2$ for each individual compound corresponds in each case to one line of table A.

Table 120: Compounds 3571 to 3600 of formula I, wherein $X^1$, $X^2$ and $R^1$ are defined as in line P-120 of table P and the meaning of $R^2$ for each individual compound corresponds in each case to one line of table A.

Table 121: Compounds 3601 to 3630 of formula I, wherein $X^1$, $X^2$ and $R^1$ are defined as in line P-121 of table P and the meaning of $R^2$ for each individual compound corresponds in each case to one line of table A.

Table 122: Compounds 3631 to 3660 of formula I, wherein $X^1$, $X^2$ and $R^1$ are defined as in line P-122 of table P and the meaning of $R^2$ for each individual compound corresponds in each case to one line of table A.

Table 123: Compounds 3661 to 3690 of formula I, wherein $X^1$, $X^2$ and $R^1$ are defined as in line P-123 of table P and the meaning of $R^2$ for each individual compound corresponds in each case to one line of table A.

Table 124: Compounds 3691 to 3720 of formula I, wherein $X^1$, $X^2$ and $R^1$ are defined as in line P-124 of table P and the meaning of $R^2$ for each individual compound corresponds in each case to one line of table A.

Table 125: Compounds 3721 to 3750 of formula I, wherein $X^1$, $X^2$ and $R^1$ are defined as in line P-125 of table P and the meaning of $R^2$ for each individual compound corresponds in each case to one line of table A.

Table 126: Compounds 3751 to 3780 of formula I, wherein $X^1$, $X^2$ and $R^1$ are defined as in line P-126 of table P and the meaning of $R^2$ for each individual compound corresponds in each case to one line of table A.

Table 127: Compounds 3781 to 3810 of formula I, wherein $X^1$, $X^2$ and $R^1$ are defined as in line P-127 of table P and the meaning of $R^2$ for each individual compound corresponds in each case to one line of table A.

Table 128: Compounds 3810 to 3840 of formula I, wherein $X^1$, $X^2$ and $R^1$ are defined as in line P-128 of table P and the meaning of $R^2$ for each individual compound corresponds in each case to one line of table A.

Table 129: Compounds 3841 to 3870 of formula I, wherein $X^1$, $X^2$ and $R^1$ are defined as in line P-129 of table P and the meaning of $R^2$ for each individual compound corresponds in each case to one line of table A.

Table 130: Compounds 3871 to 3900 of formula I, wherein $X^1$, $X^2$ and $R^1$ are defined as in line P-130 of table P and the meaning of $R^2$ for each individual compound corresponds in each case to one line of table A.

Table 131: Compounds 3901 to 3930 of formula I, wherein $X^1$, $X^2$ and $R^1$ are defined as in line P-131 of table P and the meaning of $R^2$ for each individual compound corresponds in each case to one line of table A.

Table 132: Compounds 3931 to 3960 of formula I, wherein $X^1$, $X^2$ and $R^1$ are defined as in line P-132 of table P and the meaning of $R^2$ for each individual compound corresponds in each case to one line of table A.

Table 133: Compounds 3961 to 3990 of formula I, wherein $X^1$, $X^2$ and $R^1$ are defined as in line P-133 of table P and the meaning of $R^2$ for each individual compound corresponds in each case to one line of table A.

Table 134: Compounds 3991 to 4020 of formula I, wherein $X^1$, $X^2$ and $R^1$ are defined as in line P-134 of table P and the meaning of $R^2$ for each individual compound corresponds in each case to one line of table A.

Table 135: Compounds 4021 to 4050 of formula I, wherein $X^1$, $X^2$ and $R^1$ are defined as in line P-135 of table P and the meaning of $R^2$ for each individual compound corresponds in each case to one line of table A.

Table 136: Compounds 4051 to 4080 of formula I, wherein $X^1$, $X^2$ and $R^1$ are defined as in line P-136 of table P and the meaning of $R^2$ for each individual compound corresponds in each case to one line of table A.

Table 137: Compounds 4081 to 4110 of formula I, wherein $X^1$, $X^2$ and $R^1$ are defined as in line P-137 of table P and the meaning of $R^2$ for each individual compound corresponds in each case to one line of table A.

Table 138: Compounds 4111 to 4140 of formula I, wherein $X^1$, $X^2$ and $R^1$ are defined as in line P-138 of table P and the meaning of $R^2$ for each individual compound corresponds in each case to one line of table A.

Table 139: Compounds 4141 to 4170 of formula I, wherein $X^1$, $X^2$ and $R^1$ are defined as in line P-139 of table P and the meaning of $R^2$ for each individual compound corresponds in each case to one line of table A.

Table 140: Compounds 4171 to 4200 of formula I, wherein $X^1$, $X^2$ and $R^1$ are defined as in line P-140 of table P and the meaning of $R^2$ for each individual compound corresponds in each case to one line of table A.

Table 141: Compounds 4201 to 4230 of formula I, wherein $X^1$, $X^2$ and $R^1$ are defined as in line P-141 of table P and the meaning of $R^2$ for each individual compound corresponds in each case to one line of table A.

Table 142: Compounds 4231 to 4260 of formula I, wherein $X^1$, $X^2$ and $R^1$ are defined as in line P-142 of table P and the meaning of $R^2$ for each individual compound corresponds in each case to one line of table A.

Table 143: Compounds 4261 to 4290 of formula I, wherein $X^1$, $X^2$ and $R^1$ are defined as in line P-143 of table P and the meaning of $R^2$ for each individual compound corresponds in each case to one line of table A.

Table 144: Compounds 4291 to 4320 of formula I, wherein $X^1$, $X^2$ and $R^1$ are defined as in line P-144 of table P and the meaning of $R^2$ for each individual compound corresponds in each case to one line of table A.

Table 145: Compounds 4321 to 4350 of formula I, wherein $X^1$, $X^2$ and $R^1$ are defined as in line P-145 of table P and the meaning of $R^2$ for each individual compound corresponds in each case to one line of table A.

Table 146: Compounds 4351 to 4380 of formula I, wherein $X^1$, $X^2$ and $R^1$ are defined as in line P-146 of table P and the meaning of $R^2$ for each individual compound corresponds in each case to one line of table A.

Table 147: Compounds 4381 to 4410 of formula I, wherein $X^1$, $X^2$ and $R^1$ are defined as in line P-147 of table P and the meaning of $R^2$ for each individual compound corresponds in each case to one line of table A.

Table 148: Compounds 4411 to 4440 of formula I, wherein $X^1$, $X^2$ and $R^1$ are defined as in line P-148 of table P and the meaning of $R^2$ for each individual compound corresponds in each case to one line of table A.

Table 148a: Compounds 4441 to 4470 of formula I, wherein $X^1$, $X^2$ and $R^1$ are defined as in line P-149 of table P and the meaning of $R^2$ for each individual compound corresponds in each case to one line of table A.

Table 148b: Compounds 4471 to 4500 of formula I, wherein $X^1$, $X^2$ and $R^1$ are defined as in line P-150 of table P and the meaning of $R^2$ for each individual compound corresponds in each case to one line of table A.

Table 148c: Compounds 4501 to 4530 of formula I, wherein $X^1$, $X^2$ and $R^1$ are defined as in line P-151 of table P and the meaning of $R^2$ for each individual compound corresponds in each case to one line of table A.

Table 148d: Compounds 4531 to 4560 of formula I, wherein $X^1$, $X^2$ and $R^1$ are defined as in line P-152 of table P and the meaning of $R^2$ for each individual compound corresponds in each case to one line of table A.

Table 148e: Compounds 4561 to 4590 of formula I, wherein $X^1$, $X^2$ and $R^1$ are defined as in line P-153 of table P and the meaning of $R^2$ for each individual compound corresponds in each case to one line of table A.

Table 148f: Compounds 4591 to 4620 of formula I, wherein $X^1$, $X^2$ and $R^1$ are defined as in line P-154 of table P and the meaning of $R^2$ for each individual compound corresponds in each case to one line of table A.

Table 148g: Compounds 4621 to 4650 of formula I, wherein $X^1$, $X^2$ and $R^1$ are defined as in line P-155 of table P and the meaning of $R^2$ for each individual compound corresponds in each case to one line of table A.

Table 148h: Compounds 4651 to 4680 of formula I, wherein $X^1$, $X^2$ and $R^1$ are defined as in line P-156 of table P and the meaning of $R^2$ for each individual compound corresponds in each case to one line of table A.

Table 148i: Compounds 4681 to 4710 of formula I, wherein $X^1$, $X^2$ and $R^1$ are defined as in line P-157 of table P and the meaning of $R^2$ for each individual compound corresponds in each case to one line of table A.

Table 148j: Compounds 4711 to 4740 of formula I, wherein $X^1$, $X^2$ and $R^1$ are defined as in line P-158 of table P and the meaning of $R^2$ for each individual compound corresponds in each case to one line of table A.

Table 148k: Compounds 4741 to 4770 of formula I, wherein $X^1$, $X^2$ and $R^1$ are defined as in line P-159 of table P and the meaning of $R^2$ for each individual compound corresponds in each case to one line of table A.

Table 148l: Compounds 4771 to 4800 of formula I, wherein $X^1$, $X^2$ and $R^1$ are defined as in line P-160 of table P and the meaning of $R^2$ for each individual compound corresponds in each case to one line of table A.

Table 148m: Compounds 4801 to 4830 of formula I, wherein $X^1$, $X^2$ and $R^1$ are defined as in line P-161 of table P and the meaning of $R^2$ for each individual compound corresponds in each case to one line of table A.

Table 148n: Compounds 4831 to 4860 of formula I, wherein $X^1$, $X^2$ and $R^1$ are defined as in line P-162 of table P and the meaning of $R^2$ for each individual compound corresponds in each case to one line of table A.

Table 148o: Compounds 4861 to 4890 of formula I, wherein $X^1$, $X^2$ and $R^1$ are defined as in line P-163 of table P and the meaning of $R^2$ for each individual compound corresponds in each case to one line of table A.

Table 148p: Compounds 4891 to 4920 of formula I, wherein $X^1$, $X^2$ and $R^1$ are defined as in line P-164 of table P and the meaning of $R^2$ for each individual compound corresponds in each case to one line of table A.

Table 148q: Compounds 4921 to 4950 of formula I, wherein $X^1$, $X^2$ and $R^1$ are defined as in line P-165 of table P and the meaning of $R^2$ for each individual compound corresponds in each case to one line of table A.

Table 148r: Compounds 4951 to 4980 of formula I, wherein $X^1$, $X^2$ and $R^1$ are defined as in line P-166 of table P and the meaning of $R^2$ for each individual compound corresponds in each case to one line of table A.

Table 148s: Compounds 4981 to 5010 of formula I, wherein $X^1$, $X^2$ and $R^1$ are defined as in line P-167 of table P and the meaning of $R^2$ for each individual compound corresponds in each case to one line of table A.

Table 148t: Compounds 5011 to 5040 of formula I, wherein $X^1$, $X^2$ and $R^1$ are defined as in line P-168 of table P and the meaning of $R^2$ for each individual compound corresponds in each case to one line of table A.

Table 148u: Compounds 5041 to 5070 of formula I, wherein $X^1$, $X^2$ and $R^1$ are defined as in line P-169 of table P and the meaning of $R^2$ for each individual compound corresponds in each case to one line of table A.

Table 148v: Compounds 5071 to 5100 of formula I, wherein $X^1$, $X^2$ and $R^1$ are defined as in line P-170 of table P and the meaning of $R^2$ for each individual compound corresponds in each case to one line of table A.

Table 148w: Compounds 5101 to 5130 of formula I, wherein $X^1$, $X^2$ and $R^1$ are defined as in line P-171 of table P and the meaning of $R^2$ for each individual compound corresponds in each case to one line of table A.

Table 148x: Compounds 5131 to 5160 of formula I, wherein $X^1$, $X^2$ and $R^1$ are defined as in line P-172 of table P and the meaning of $R^2$ for each individual compound corresponds in each case to one line of table A.

Table 148y: Compounds 5161 to 5190 of formula I, wherein $X^1$, $X^2$ and $R^1$ are defined as in line P-173 of table P and the meaning of $R^2$ for each individual compound corresponds in each case to one line of table A.

Table 148z: Compounds 5191 to 5220 of formula I, wherein $X^1$, $X^2$ and $R^1$ are defined as in line P-174 of table P and the meaning of $R^2$ for each individual compound corresponds in each case to one line of table A.

Table 148aa: Compounds 5221 to 5250 of formula I, wherein $X^1$, $X^2$ and $R^1$ are defined as in line P-175 of table P and the meaning of $R^2$ for each individual compound corresponds in each case to one line of table A.

Table 148bb: Compounds 5251 to 5280 of formula I, wherein $X^1$, $X^2$ and $R^1$ are defined as in line P-176 of table P and the meaning of $R^2$ for each individual compound corresponds in each case to one line of table A.

Table 148cc: Compounds 5281 to 5310 of formula I, wherein $X^1$, $X^2$ and $R^1$ are defined as in line P-177 of table P and the meaning of $R^2$ for each individual compound corresponds in each case to one line of table A.

Table 148dd: Compounds 5311 to 5340 of formula I, wherein $X^1$, $X^2$ and $R^1$ are defined as in line P-178 of table P and the meaning of $R^2$ for each individual compound corresponds in each case to one line of table A.

Table 148ee: Compounds 5441 to 5370 of formula I, wherein $X^1$, $X^2$ and $R^1$ are defined as in line P-179 of table P and the meaning of $R^2$ for each individual compound corresponds in each case to one line of table A.

Table 148ff: Compounds 5371 to 5400 of formula I, wherein $X^1$, $X^2$ and $R^1$ are defined as in line P-180 of table P and the meaning of $R^2$ for each individual compound corresponds in each case to one line of table A.

Table 148gg: Compounds 5401 to 5430 of formula I, wherein $X^1$, $X^2$ and $R^1$ are defined as in line P-181 of table P and the meaning of $R^2$ for each individual compound corresponds in each case to one line of table A.

Table 148hh: Compounds 5431 to 5460 of formula I, wherein $X^1$, $X^2$ and $R^1$ are defined as in line P-182 of table P and the meaning of $R^2$ for each individual compound corresponds in each case to one line of table A.

Table 148ii: Compounds 5461 to 5490 of formula I, wherein $X^1$, $X^2$ and $R^1$ are defined as in line P-183 of table P and the meaning of $R^2$ for each individual compound corresponds in each case to one line of table A.

Table 148jj: Compounds 5491 to 5520 of formula I, wherein $X^1$, $X^2$ and $R^1$ are defined as in line P-184 of table P and the meaning of $R^2$ for each individual compound corresponds in each case to one line of table A.

Table 149: Compounds 1a to 30a of formula I, wherein $X^1$, $X^2$ and $R^1$ are defined as in line P-1 of table P and the meaning of $R^2$ for each individual compound corresponds in each case to one line of table A1.

Table 150: Compounds 31a to 60a of formula I, wherein $X^1$, $X^2$ and $R^1$ are defined as in line P-2 of table P and the meaning of $R^2$ for each individual compound corresponds in each case to one line of table A1.

Table 151: Compounds 61a to 90a of formula I, wherein $X^1$, $X^2$ and $R^1$ are defined as in line P-3 of table P and the meaning of $R^2$ for each individual compound corresponds in each case to one line of table A1.

Table 152: Compounds 91a to 120a of formula I, wherein $X^1$, $X^2$ and $R^1$ are defined as in line P-4 of table P and the meaning of $R^2$ for each individual compound corresponds in each case to one line of table A1.

Table 153: Compounds 121a to 150a of formula I, wherein $X^1$, $X^2$ and $R^1$ are defined as in line P-5 of table P and the meaning of $R^2$ for each individual compound corresponds in each case to one line of table A1.

Table 154: Compounds 151a to 180a of formula I, wherein $X^1$, $X^2$ and $R^1$ are defined as in line P-6 of table P and the meaning of $R^2$ for each individual compound corresponds in each case to one line of table A1.

Table 155: Compounds 181a to 210a of formula I, wherein $X^1$, $X^2$ and $R^1$ are defined as in line P-7 of table P and the meaning of $R^2$ for each individual compound corresponds in each case to one line of table A1.

Table 156: Compounds 211a to 240a of formula I, wherein $X^1$, $X^2$ and $R^1$ are defined as in line P-8 of table P and the meaning of $R^2$ for each individual compound corresponds in each case to one line of table A1.

Table 157: Compounds 241a to 270a of formula I, wherein $X^1$, $X^2$ and $R^1$ are defined as in line P-9 of table P and the meaning of $R^2$ for each individual compound corresponds in each case to one line of table A1.

Table 158: Compounds 271a to 300a of formula I, wherein $X^1$, $X^2$ and $R^1$ are defined as in line P-10 of table P and the meaning of $R^2$ for each individual compound corresponds in each case to one line of table A1.

Table 159: Compounds 301a to 330a of formula I, wherein $X^1$, $X^2$ and $R^1$ are defined as in line P-11 of table P and the meaning of $R^2$ for each individual compound corresponds in each case to one line of table A1.

Table 160: Compounds 331a to 360a of formula I, wherein $X^1$, $X^2$ and $R^1$ are defined as in line P-12 of table P and the meaning of $R^2$ for each individual compound corresponds in each case to one line of table A1.

Table 161: Compounds 361a to 390a of formula I, wherein $X^1$, $X^2$ and $R^1$ are defined as in line P-13 of table P and the meaning of $R^2$ for each individual compound corresponds in each case to one line of table A1.

Table 162: Compounds 391a to 420a of formula I, wherein $X^1$, $X^2$ and $R^1$ are defined as in line P-14 of table P and the meaning of $R^2$ for each individual compound corresponds in each case to one line of table A1.

Table 163: Compounds 421a to 450a of formula I, wherein $X^1$, $X^2$ and $R^1$ are defined as in line P-15 of table P and the meaning of $R^2$ for each individual compound corresponds in each case to one line of table A1.

Table 164: Compounds 451a to 480a of formula I, wherein $X^1$, $X^2$ and $R^1$ are defined as in line P-16 of table P and the meaning of $R^2$ for each individual compound corresponds in each case to one line of table A1.

Table 165: Compounds 481a to 510a of formula I, wherein $X^1$, $X^2$ and $R^1$ are defined as in line P-17 of table P and the meaning of $R^2$ for each individual compound corresponds in each case to one line of table A1.

Table 166: Compounds 511a to 540a of formula I, wherein $X^1$, $X^2$ and $R^1$ are defined as in line P-18 of table P and the meaning of $R^2$ for each individual compound corresponds in each case to one line of table A1.

Table 167: Compounds 541a to 570a of formula I, wherein $X^1$, $X^2$ and $R^1$ are defined as in line P-19 of table P and the meaning of $R^2$ for each individual compound corresponds in each case to one line of table A1.

Table 168: Compounds 571a to 600a of formula I, wherein $X^1$, $X^2$ and $R^1$ are defined as in line P-20 of table P and the meaning of $R^2$ for each individual compound corresponds in each case to one line of table A1.

Table 169: Compounds 601a to 630a of formula I, wherein $X^1$, $X^2$ and $R^1$ are defined as in line P-21 of table P and the meaning of $R^2$ for each individual compound corresponds in each case to one line of table A1.

Table 170: Compounds 631a to 660a of formula I, wherein $X^1$, $X^2$ and $R^1$ are defined as in line P-22 of table P and the meaning of $R^2$ for each individual compound corresponds in each case to one line of table A1.

Table 171: Compounds 661a to 690a of formula I, wherein $X^1$, $X^2$ and $R^1$ are defined as in line P-23 of table P and the meaning of $R^2$ for each individual compound corresponds in each case to one line of table A1.

Table 172: Compounds 691a to 720a of formula I, wherein $X^1$, $X^2$ and $R^1$ are defined as in line P-24 of table P and the meaning of $R^2$ for each individual compound corresponds in each case to one line of table A1.

Table 173: Compounds 721a to 750a of formula I, wherein $X^1$, $X^2$ and $R^1$ are defined as in line P-25 of table P and the meaning of $R^2$ for each individual compound corresponds in each case to one line of table A1.

Table 174: Compounds 751a to 780a of formula I, wherein $X^1$, $X^2$ and $R^1$ are defined as in line P-26 of table P and the meaning of $R^2$ for each individual compound corresponds in each case to one line of table A1.

Table 175: Compounds 781a to 810a of formula I, wherein $X^1$, $X^2$ and $R^1$ are defined as in line P-27 of table P and the meaning of $R^2$ for each individual compound corresponds in each case to one line of table A1.

Table 176: Compounds 811a to 840a of formula I, wherein $X^1$, $X^2$ and $R^1$ are defined as in line P-28 of table P and the meaning of $R^2$ for each individual compound corresponds in each case to one line of table A1.

Table 177: Compounds 841a to 870a of formula I, wherein $X^1$, $X^2$ and $R^1$ are defined as in line P-29 of table P and the meaning of $R^2$ for each individual compound corresponds in each case to one line of table A1.

Table 178: Compounds 871a to 900a of formula I, wherein $X^1$, $X^2$ and $R^1$ are defined as in line P-30 of table P and the meaning of $R^2$ for each individual compound corresponds in each case to one line of table A1.

Table 179: Compounds 901a to 930a of formula I, wherein $X^1$, $X^2$ and $R^1$ are defined as in line P-31 of table P and the meaning of $R^2$ for each individual compound corresponds in each case to one line of table A1.

Table 180: Compounds 931a to 960a of formula I, wherein $X^1$, $X^2$ and $R^1$ are defined as in line P-32 of table P and the meaning of $R^2$ for each individual compound corresponds in each case to one line of table A1.

Table 181: Compounds 961a to 990a of formula I, wherein $X^1$, $X^2$ and $R^1$ are defined as in line P-33 of table P and the meaning of $R^2$ for each individual compound corresponds in each case to one line of table A1.

Table 182: Compounds 991a to 1020a of formula I, wherein $X^1$, $X^2$ and $R^1$ are defined as in line P-34 of table P and the meaning of $R^2$ for each individual compound corresponds in each case to one line of table A1.

Table 183: Compounds 1021a to 1050a of formula I, wherein $X^1$, $X^2$ and $R^1$ are defined as in line P-35 of table P and the meaning of $R^2$ for each individual compound corresponds in each case to one line of table A1.

Table 184: Compounds 1051a to 1080a of formula I, wherein $X^1$, $X^2$ and $R^1$ are defined as in line P-36 of table P and the meaning of $R^2$ for each individual compound corresponds in each case to one line of table A1.

Table 185: Compounds 1081a to 1110a of formula I, wherein $X^1$, $X^2$ and $R^1$ are defined as in line P-37 of table P and the meaning of $R^2$ for each individual compound corresponds in each case to one line of table A1.

Table 186: Compounds 1111a to 1140a of formula I, wherein $X^1$, $X^2$ and $R^1$ are defined as in line P-38 of table P and the meaning of $R^2$ for each individual compound corresponds in each case to one line of table A1.

Table 187: Compounds 1141a to 1170a of formula I, wherein $X^1$, $X^2$ and $R^1$ are defined as in line P-39 of table P and the meaning of $R^2$ for each individual compound corresponds in each case to one line of table A1.

Table 188: Compounds 1171a to 1200a of formula I, wherein $X^1$, $X^2$ and $R^1$ are defined as in line P-40 of table P and the meaning of $R^2$ for each individual compound corresponds in each case to one line of table A1.

Table 189: Compounds 1201a to 1230a of formula I, wherein $X^1$, $X^2$ and $R^1$ are defined as in line P-41 of table P and the meaning of $R^2$ for each individual compound corresponds in each case to one line of table A1.

Table 190: Compounds 1231a to 1260a of formula I, wherein $X^1$, $X^2$ and $R^1$ are defined as in line P-42 of table P and the meaning of $R^2$ for each individual compound corresponds in each case to one line of table A1.

Table 191: Compounds 1261a to 1290a of formula I, wherein $X^1$, $X^2$ and $R^1$ are defined as in line P-43 of table P and the Table 192: Compounds 1291a to 1320a of formula I, wherein $X^1$, $X^2$ and $R^1$ are defined as in line P-44 of table P and the meaning of $R^2$ for each individual compound corresponds in each case to one line of table A1.
Table 193: Compounds 1321a to 1350a of formula I, wherein $X^1$, $X^2$ and $R^1$ are defined as in line P-45 of table P and the meaning of $R^2$ for each individual compound corresponds in each case to one line of table A1.
Table 194: Compounds 1351a to 1380a of formula I, wherein $X^1$, $X^2$ and $R^1$ are defined as in line P-46 of table P and the meaning of $R^2$ for each individual compound corresponds in each case to one line of table A1.
Table 195: Compounds 1381a to 1410a of formula I, wherein $X^1$, $X^2$ and $R^1$ are defined as in line P-47 of table P and the meaning of $R^2$ for each individual compound corresponds in each case to one line of table A1.
Table 196: Compounds 1411a to 1440a of formula I, wherein $X^1$, $X^2$ and $R^1$ are defined as in line P-48 of table P and the meaning of $R^2$ for each individual compound corresponds in each case to one line of table A1.
Table 197: Compounds 1441a to 1470a of formula I, wherein $X^1$, $X^2$ and $R^1$ are defined as in line P-49 of table P and the meaning of $R^2$ for each individual compound corresponds in each case to one line of table A1.
Table 198: Compounds 1471a to 1500a of formula I, wherein $X^1$, $X^2$ and $R^1$ are defined as in line P-50 of table P and the meaning of $R^2$ for each individual compound corresponds in each case to one line of table A1.
Table 199: Compounds 1501a to 1530a of formula I, wherein $X^1$, $X^2$ and $R^1$ are defined as in line P-51 of table P and the meaning of $R^2$ for each individual compound corresponds in each case to one line of table A1.
Table 200: Compounds 1531a to 1560a of formula I, wherein $X^1$, $X^2$ and $R^1$ are defined as in line P-52 of table P and the meaning of $R^2$ for each individual compound corresponds in each case to one line of table A1.
Table 201: Compounds 1561a to 1590a of formula I, wherein $X^1$, $X^2$ and $R^1$ are defined as in line P-53 of table P and the meaning of $R^2$ for each individual compound corresponds in each case to one line of table A1.
Table 202: Compounds 1591a to 1620a of formula I, wherein $X^1$, $X^2$ and $R^1$ are defined as in line P-54 of table P and the meaning of $R^2$ for each individual compound corresponds in each case to one line of table A1.
Table 203: Compounds 1621a to 1650a of formula I, wherein $X^1$, $X^2$ and $R^1$ are defined as in line P-55 of table P and the meaning of $R^2$ for each individual compound corresponds in each case to one line of table A1.
Table 204: Compounds 1651a to 1680a of formula I, wherein $X^1$, $X^2$ and $R^1$ are defined as in line P-56 of table P and the meaning of $R^2$ for each individual compound corresponds in each case to one line of table A1.
Table 205: Compounds 1681a to 1710a of formula I, wherein $X^1$, $X^2$ and $R^1$ are defined as in line P-57 of table P and the meaning of $R^2$ for each individual compound corresponds in each case to one line of table A1.
Table 206: Compounds 1711a to 1740a of formula I, wherein $X^1$, $X^2$ and $R^1$ are defined as in line P-58 of table P and the meaning of $R^2$ for each individual compound corresponds in each case to one line of table A1.
Table 207: Compounds 1741a to 1770a of formula I, wherein $X^1$, $X^2$ and $R^1$ are defined as in line P-59 of table P and the meaning of $R^2$ for each individual compound corresponds in each case to one line of table A1.
Table 208: Compounds 1771a to 1800a of formula I, wherein $X^1$, $X^2$ and $R^1$ are defined as in line P-60 of table P and the meaning of $R^2$ for each individual compound corresponds in each case to one line of table A1.
Table 209: Compounds 1801a to 1830a of formula I, wherein $X^1$, $X^2$ and $R^1$ are defined as in line P-61 of table P and the meaning of $R^2$ for each individual compound corresponds in each case to one line of table A1.
Table 210: Compounds 1831a to 1860a of formula I, wherein $X^1$, $X^2$ and $R^1$ are defined as in line P-62 of table P and the meaning of $R^2$ for each individual compound corresponds in each case to one line of table A1.
Table 211: Compounds 1861a to 1890a of formula I, wherein $X^1$, $X^2$ and $R^1$ are defined as in line P-63 of table P and the meaning of $R^2$ for each individual compound corresponds in each case to one line of table A1.
Table 212: Compounds 1891a to 1920a of formula I, wherein $X^1$, $X^2$ and $R^1$ are defined as in line P-64 of table P and the meaning of $R^2$ for each individual compound corresponds in each case to one line of table A1.
Table 213: Compounds 1921a to 1950a of formula I, wherein $X^1$, $X^2$ and $R^1$ are defined as in line P-65 of table P and the meaning of $R^2$ for each individual compound corresponds in each case to one line of table A1.
Table 214: Compounds 1951a to 1980a of formula I, wherein $X^1$, $X^2$ and $R^1$ are defined as in line P-66 of table P and the meaning of $R^2$ for each individual compound corresponds in each case to one line of table A1.
Table 215: Compounds 1981a to 2010a of formula I, wherein $X^1$, $X^2$ and $R^1$ are defined as in line P-67 of table P and the meaning of $R^2$ for each individual compound corresponds in each case to one line of table A1.
Table 216: Compounds 2011a to 2040a of formula I, wherein $X^1$, $X^2$ and $R^1$ are defined as in line P-68 of table P and the meaning of $R^2$ for each individual compound corresponds in each case to one line of table A1.
Table 217: Compounds 2041a to 2070a of formula I, wherein $X^1$, $X^2$ and $R^1$ are defined as in line P-69 of table P and the meaning of $R^2$ for each individual compound corresponds in each case to one line of table A1.
Table 218: Compounds 2071a to 2100a of formula I, wherein $X^1$, $X^2$ and $R^1$ are defined as in line P-70 of table P and the meaning of $R^2$ for each individual compound corresponds in each case to one line of table A1.
Table 219: Compounds 2101a to 2130a of formula I, wherein $X^1$, $X^2$ and $R^1$ are defined as in line P-71 of table P and the meaning of $R^2$ for each individual compound corresponds in each case to one line of table A1.
Table 220: Compounds 2131a to 2160a of formula I, wherein $X^1$, $X^2$ and $R^1$ are defined as in line P-72 of table P and the meaning of $R^2$ for each individual compound corresponds in each case to one line of table A1.
Table 221: Compounds 2161a to 2190a of formula I, wherein $X^1$, $X^2$ and $R^1$ are defined as in line P-73 of table P and the meaning of $R^2$ for each individual compound corresponds in each case to one line of table A1.
Table 222: Compounds 2191a to 2220a of formula I, wherein $X^1$, $X^2$ and $R^1$ are defined as in line P-74 of table P and the meaning of $R^2$ for each individual compound corresponds in each case to one line of table A1.
Table 223: Compounds 2221a to 2250a of formula I, wherein $X^1$, $X^2$ and $R^1$ are defined as in line P-75 of table P and the meaning of $R^2$ for each individual compound corresponds in each case to one line of table A1.
Table 224: Compounds 2251a to 2280a of formula I, wherein $X^1$, $X^2$ and $R^1$ are defined as in line P-76 of table P and the meaning of $R^2$ for each individual compound corresponds in each case to one line of table A1.
Table 225: Compounds 2281a to 2310a of formula I, wherein $X^1$, $X^2$ and $R^1$ are defined as in line P-77 of table P and the meaning of $R^2$ for each individual compound corresponds in each case to one line of table A1.
Table 226: Compounds 2311a to 2340a of formula I, wherein $X^1$, $X^2$ and $R^1$ are defined as in line P-78 of table P and the meaning of $R^2$ for each individual compound corresponds in each case to one line of table A1.
Table 227: Compounds 2341a to 2370a of formula I, wherein $X^1$, $X^2$ and $R^1$ are defined as in line P-79 of table P and the meaning of $R^2$ for each individual compound corresponds in each case to one line of table A1.
Table 228: Compounds 2371a to 2400a of formula I, wherein $X^1$, $X^2$ and $R^1$ are defined as in line P-80 of table P and the meaning of $R^2$ for each individual compound corresponds in each case to one line of table A1.
Table 229: Compounds 2401a to 2430a of formula I, wherein $X^1$, $X^2$ and $R^1$ are defined as in line P-81 of table P and the meaning of $R^2$ for each individual compound corresponds in each case to one line of table A1.
Table 230: Compounds 2431a to 2460a of formula I, wherein $X^1$, $X^2$ and $R^1$ are defined as in line P-82 of table P and the meaning of $R^2$ for each individual compound corresponds in each case to one line of table A1.
Table 231: Compounds 2461a to 2490a of formula I, wherein $X^1$, $X^2$ and $R^1$ are defined as in line P-83 of table P and the meaning of $R^2$ for each individual compound corresponds in each case to one line of table A1.
Table 232: Compounds 2491a to 2520a of formula I, wherein $X^1$, $X^2$ and $R^1$ are defined as in line P-84 of table P and the meaning of $R^2$ for each individual compound corresponds in each case to one line of table A1.
Table 233: Compounds 2521a to 2550a of formula I, wherein $X^1$, $X^2$ and $R^1$ are defined as in line P-85 of table P and the meaning of $R^2$ for each individual compound corresponds in each case to one line of table A1.
Table 234: Compounds 2551a to 2580a of formula I, wherein $X^1$, $X^2$ and $R^1$ are defined as in line P-86 of table P and the meaning of $R^2$ for each individual compound corresponds in each case to one line of table A1.
Table 235: Compounds 2581a to 2610a of formula I, wherein $X^1$, $X^2$ and $R^1$ are defined as in line P-87 of table P and the meaning of $R^2$ for each individual compound corresponds in each case to one line of table A1.
Table 236: Compounds 2611a to 2640a of formula I, wherein $X^1$, $X^2$ and $R^1$ are defined as in line P-88 of table P and the meaning of $R^2$ for each individual compound corresponds in each case to one line of table A1.
Table 237: Compounds 2641a to 2670a of formula I, wherein $X^1$, $X^2$ and $R^1$ are defined as in line P-89 of table P and the meaning of $R^2$ for each individual compound corresponds in each case to one line of table A1.
Table 238: Compounds 2671a to 2700a of formula I, wherein $X^1$, $X^2$ and $R^1$ are defined as in line P-90 of table P and the meaning of $R^2$ for each individual compound corresponds in each case to one line of table A1.
Table 239: Compounds 2701a to 2730a of formula I, wherein $X^1$, $X^2$ and $R^1$ are defined as in line P-91 of table P and the meaning of $R^2$ for each individual compound corresponds in each case to one line of table A1.
Table 240: Compounds 2731a to 2760a of formula I, wherein $X^1$, $X^2$ and $R^1$ are defined as in line P-92 of table P and the meaning of $R^2$ for each individual compound corresponds in each case to one line of table A1.
Table 241: Compounds 2761a to 2790a of formula I, wherein $X^1$, $X^2$ and $R^1$ are defined as in line P-93 of table P and the meaning of $R^2$ for each individual compound corresponds in each case to one line of table A1.
Table 242: Compounds 2791a to 2820a of formula I, wherein $X^1$, $X^2$ and $R^1$ are defined as in line P-94 of table P and the meaning of $R^2$ for each individual compound corresponds in each case to one line of table A1.
Table 243: Compounds 2821a to 2850a of formula I, wherein $X^1$, $X^2$ and $R^1$ are defined as in line P-95 of table P and the meaning of $R^2$ for each individual compound corresponds in each case to one line of table A1.
Table 244: Compounds 2851a to 2880a of formula I, wherein $X^1$, $X^2$ and $R^1$ are defined as in line P-96 of table P and the meaning of $R^2$ for each individual compound corresponds in each case to one line of table A1.
Table 245: Compounds 2881a to 2910a of formula I, wherein $X^1$, $X^2$ and $R^1$ are defined as in line P-97 of table P and the meaning of $R^2$ for each individual compound corresponds in each case to one line of table A1.
Table 246: Compounds 2911a to 2940a of formula I, wherein $X^1$, $X^2$ and $R^1$ are defined as in line P-98 of table P and the meaning of $R^2$ for each individual compound corresponds in each case to one line of table A1.
Table 247: Compounds 2941a to 2970a of formula I, wherein $X^1$, $X^2$ and $R^1$ are defined as in line P-99 of table P and the meaning of $R^2$ for each individual compound corresponds in each case to one line of table A1.
Table 248: Compounds 2971a to 3000a of formula I, wherein $X^1$, $X^2$ and $R^1$ are defined as in line P-100 of table P and the meaning of $R^2$ for each individual compound corresponds in each case to one line of table A1.
Table 249: Compounds 3001a to 3030a of formula I, wherein $X^1$, $X^2$ and $R^1$ are defined as in line P-101 of table P and the meaning of $R^2$ for each individual compound corresponds in each case to one line of table A1.
Table 250: Compounds 3031a to 3060a of formula I, wherein $X^1$, $X^2$ and $R^1$ are defined as in line P-102 of table P and the meaning of $R^2$ for each individual compound corresponds in each case to one line of table A1.
Table 251: Compounds 3061a to 3090a of formula I, wherein $X^1$, $X^2$ and $R^1$ are defined as in line P-103 of table P and the meaning of $R^2$ for each individual compound corresponds in each case to one line of table A1.
Table 252: Compounds 3091a to 3120a of formula I, wherein $X^1$, $X^2$ and $R^1$ are defined as in line P-104 of table P and the meaning of $R^2$ for each individual compound corresponds in each case to one line of table A1.
Table 253: Compounds 3121a to 3150a of formula I, wherein $X^1$, $X^2$ and $R^1$ are defined as in line P-105 of table P and the meaning of $R^2$ for each individual compound corresponds in each case to one line of table A1.
Table 254: Compounds 3151a to 3180a of formula I, wherein $X^1$, $X^2$ and $R^1$ are defined as in line P-106 of table P and the meaning of $R^2$ for each individual compound corresponds in each case to one line of table A1.
Table 255: Compounds 3181a to 3210a of formula I, wherein $X^1$, $X^2$ and $R^1$ are defined as in line P-107 of table P and the meaning of $R^2$ for each individual compound corresponds in each case to one line of table A1.
Table 256: Compounds 3211a to 3240a of formula I, wherein $X^1$, $X^2$ and $R^1$ are defined as in line P-108 of table P and the meaning of $R^2$ for each individual compound corresponds in each case to one line of table A1.
Table 257: Compounds 3241a to 3270a of formula I, wherein $X^1$, $X^2$ and $R^1$ are defined as in line P-109 of table P and the meaning of $R^2$ for each individual compound corresponds in each case to one line of table A1.

Table 258: Compounds 3271a to 3300a of formula I, wherein $X^1$, $X^2$ and $R^1$ are defined as in line P-110 of table P and the meaning of $R^2$ for each individual compound corresponds in each case to one line of table A1.

Table 259: Compounds 3301a to 3330a of formula I, wherein $X^1$, $X^2$ and $R^1$ are defined as in line P-111 of table P and the meaning of $R^2$ for each individual compound corresponds in each case to one line of table A1.

Table 260: Compounds 3331a to 3360a of formula I, wherein $X^1$, $X^2$ and $R^1$ are defined as in line P-112 of table P and the meaning of $R^2$ for each individual compound corresponds in each case to one line of table A1.

Table 261: Compounds 3361a to 3390a of formula I, wherein $X^1$, $X^2$ and $R^1$ are defined as in line P-113 of table P and the meaning of $R^2$ for each individual compound corresponds in each case to one line of table A1.

Table 262: Compounds 3391a to 3420a of formula I, wherein $X^1$, $X^2$ and $R^1$ are defined as in line P-114 of table P and the meaning of $R^2$ for each individual compound corresponds in each case to one line of table A1.

Table 263: Compounds 3421a to 3450a of formula I, wherein $X^1$, $X^2$ and $R^1$ are defined as in line P-115 of table P and the meaning of $R^2$ for each individual compound corresponds in each case to one line of table A1.

Table 264: Compounds 3451a to 3480a of formula I, wherein $X^1$, $X^2$ and $R^1$ are defined as in line P-116 of table P and the meaning of $R^2$ for each individual compound corresponds in each case to one line of table A1.

Table 265: Compounds 3481a to 3510a of formula I, wherein $X^1$, $X^2$ and $R^1$ are defined as in line P-117 of table P and the meaning of $R^2$ for each individual compound corresponds in each case to one line of table A1.

Table 266: Compounds 3510a to 3540a of formula I, wherein $X^1$, $X^2$ and $R^1$ are defined as in line P-118 of table P and the meaning of $R^2$ for each individual compound corresponds in each case to one line of table A1.

Table 267: Compounds 3541a to 3570a of formula I, wherein $X^1$, $X^2$ and $R^1$ are defined as in line P-119 of table P and the meaning of $R^2$ for each individual compound corresponds in each case to one line of table A1.

Table 268: Compounds 3571a to 3600a of formula I, wherein $X^1$, $X^2$ and $R^1$ are defined as in line P-120 of table P and the meaning of $R^2$ for each individual compound corresponds in each case to one line of table A1.

Table 269: Compounds 3601a to 3630a of formula I, wherein $X^1$, $X^2$ and $R^1$ are defined as in line P-121 of table P and the meaning of $R^2$ for each individual compound corresponds in each case to one line of table A1.

Table 270: Compounds 3631a to 3660a of formula I, wherein $X^1$, $X^2$ and $R^1$ are defined as in line P-122 of table P and the meaning of $R^2$ for each individual compound corresponds in each case to one line of table A1.

Table 271: Compounds 3661a to 3690a of formula I, wherein $X^1$, $X^2$ and $R^1$ are defined as in line P-123 of table P and the meaning of $R^2$ for each individual compound corresponds in each case to one line of table A1.

Table 272: Compounds 3691a to 3720a of formula I, wherein $X^1$, $X^2$ and $R^1$ are defined as in line P-124 of table P and the meaning of $R^2$ for each individual compound corresponds in each case to one line of table A1.

Table 273: Compounds 3721a to 3750a of formula I, wherein $X^1$, $X^2$ and $R^1$ are defined as in line P-125 of table P and the meaning of $R^2$ for each individual compound corresponds in each case to one line of table A1.

Table 274: Compounds 3751a to 3780a of formula I, wherein $X^1$, $X^2$ and $R^1$ are defined as in line P-126 of table P and the meaning of $R^2$ for each individual compound corresponds in each case to one line of table A1.

Table 275: Compounds 3781a to 3810a of formula I, wherein $X^1$, $X^2$ and $R^1$ are defined as in line P-127 of table P and the meaning of $R^2$ for each individual compound corresponds in each case to one line of table A1.

Table 276: Compounds 3810a to 3840a of formula I, wherein $X^1$, $X^2$ and $R^1$ are defined as in line P-128 of table P and the meaning of $R^2$ for each individual compound corresponds in each case to one line of table A1.

Table 277: Compounds 3841a to 3870a of formula I, wherein $X^1$, $X^2$ and $R^1$ are defined as in line P-129 of table P and the meaning of $R^2$ for each individual compound corresponds in each case to one line of table A1.

Table 278: Compounds 3871a to 3900a of formula I, wherein $X^1$, $X^2$ and $R^1$ are defined as in line P-130 of table P and the meaning of $R^2$ for each individual compound corresponds in each case to one line of table A1.

Table 279: Compounds 3901a to 3930a of formula I, wherein $X^1$, $X^2$ and $R^1$ are defined as in line P-131 of table P and the meaning of $R^2$ for each individual compound corresponds in each case to one line of table A1.

Table 280: Compounds 3931a to 3960a of formula I, wherein $X^1$, $X^2$ and $R^1$ are defined as in line P-132 of table P and the meaning of $R^2$ for each individual compound corresponds in each case to one line of table A1.

Table 281: Compounds 3961a to 3990a of formula I, wherein $X^1$, $X^2$ and $R^1$ are defined as in line P-133 of table P and the meaning of $R^2$ for each individual compound corresponds in each case to one line of table A1.

Table 282: Compounds 3991a to 4020a of formula I, wherein $X^1$, $X^2$ and $R^1$ are defined as in line P-134 of table P and the meaning of $R^2$ for each individual compound corresponds in each case to one line of table A1.

Table 283: Compounds 4021a to 4050a of formula I, wherein $X^1$, $X^2$ and $R^1$ are defined as in line P-135 of table P and the meaning of $R^2$ for each individual compound corresponds in each case to one line of table A1.

Table 284: Compounds 4051a to 4080a of formula I, wherein $X^1$, $X^2$ and $R^1$ are defined as in line P-136 of table P and the meaning of $R^2$ for each individual compound corresponds in each case to one line of table A1.

Table 285: Compounds 4081a to 4110a of formula I, wherein $X^1$, $X^2$ and $R^1$ are defined as in line P-137 of table P and the meaning of $R^2$ for each individual compound corresponds in each case to one line of table A1.

Table 286: Compounds 4111a to 4140a of formula I, wherein $X^1$, $X^2$ and $R^1$ are defined as in line P-138 of table P and the meaning of $R^2$ for each individual compound corresponds in each case to one line of table A1.

Table 287: Compounds 4141a to 4170a of formula I, wherein $X^1$, $X^2$ and $R^1$ are defined as in line P-139 of table P and the meaning of $R^2$ for each individual compound corresponds in each case to one line of table A1.

Table 288: Compounds 4171a to 4200a of formula I, wherein $X^1$, $X^2$ and $R^1$ are defined as in line P-140 of table P and the meaning of $R^2$ for each individual compound corresponds in each case to one line of table A1.

Table 289: Compounds 4201a to 4230a of formula I, wherein $X^1$, $X^2$ and $R^1$ are defined as in line P-141 of table P and the meaning of $R^2$ for each individual compound corresponds in each case to one line of table A1.

Table 290: Compounds 4231a to 4260a of formula I, wherein $X^1$, $X^2$ and $R^1$ are defined as in line P-142 of table P and the meaning of $R^2$ for each individual compound corresponds in each case to one line of table A1.

Table 291: Compounds 4261a to 4290a of formula I, wherein $X^1$, $X^2$ and $R^1$ are defined as in line P-143 of table P and the meaning of $R^2$ for each individual compound corresponds in each case to one line of table A1.

Table 292: Compounds 4291a to 4320a of formula I, wherein $X^1$, $X^2$ and $R^1$ are defined as in line P-144 of table P and the meaning of $R^2$ for each individual compound corresponds in each case to one line of table A1.

Table 293: Compounds 4321a to 4350a of formula I, wherein $X^1$, $X^2$ and $R^1$ are defined as in line P-145 of table P and the meaning of $R^2$ for each individual compound corresponds in each case to one line of table A1.

Table 294: Compounds 4351a to 4380a of formula I, wherein $X^1$, $X^2$ and $R^1$ are defined as in line P-146 of table P and the meaning of $R^2$ for each individual compound corresponds in each case to one line of table A1.

Table 295: Compounds 4381a to 4410a of formula I, wherein $X^1$, $X^2$ and $R^1$ are defined as in line P-147 of table P and the meaning of $R^2$ for each individual compound corresponds in each case to one line of table A1.

Table 296: Compounds 4411a to 4440a of formula I, wherein $X^1$, $X^2$ and $R^1$ are defined as in line P-148 of table P and the meaning of $R^2$ for each individual compound corresponds in each case to one line of table A1.

Table 296a: Compounds 4441a to 4470a of formula I, wherein $X^1$, $X^2$ and $R^1$ are defined as in line P-149 of table P and the meaning of $R^2$ for each individual compound corresponds in each case to one line of table A1.

Table 296b: Compounds 4471a to 4500a of formula I, wherein $X^1$, $X^2$ and $R^1$ are defined as in line P-150 of table P and the meaning of $R^2$ for each individual compound corresponds in each case to one line of table A1.

Table 296c: Compounds 4501a to 4530a of formula I, wherein $X^1$, $X^2$ and $R^1$ are defined as in line P-151 of table P and the meaning of $R^2$ for each individual compound corresponds in each case to one line of table A1.

Table 296d: Compounds 4531a to 4560a of formula I, wherein $X^1$, $X^2$ and $R^1$ are defined as in line P-152 of table P and the meaning of $R^2$ for each individual compound corresponds in each case to one line of table A1.

Table 296e: Compounds 4561a to 4590a of formula I, wherein $X^1$, $X^2$ and $R^1$ are defined as in line P-153 of table P and the meaning of $R^2$ for each individual compound corresponds in each case to one line of table A1.

Table 296f: Compounds 4591a to 4620a of formula I, wherein $X^1$, $X^2$ and $R^1$ are defined as in line P-154 of table P and the meaning of $R^2$ for each individual compound corresponds in each case to one line of table A1.

Table 296g: Compounds 4621a to 4650a of formula I, wherein $X^1$, $X^2$ and $R^1$ are defined as in line P-155 of table P and the meaning of $R^2$ for each individual compound corresponds in each case to one line of table A1.

Table 296h: Compounds 4651a to 4680a of formula I, wherein $X^1$, $X^2$ and $R^1$ are defined as in line P-156 of table P and the meaning of $R^2$ for each individual compound corresponds in each case to one line of table A1.

Table 296i: Compounds 4681a to 4710a of formula I, wherein $X^1$, $X^2$ and $R^1$ are defined as in line P-157 of table P and the meaning of $R^2$ for each individual compound corresponds in each case to one line of table A1.

Table 296j: Compounds 4711a to 4740a of formula I, wherein $X^1$, $X^2$ and $R^1$ are defined as in line P-158 of table P and the meaning of $R^2$ for each individual compound corresponds in each case to one line of table A1.

Table 296k: Compounds 4741a to 4770a of formula I, wherein $X^1$, $X^2$ and $R^1$ are defined as in line P-159 of table P and the meaning of $R^2$ for each individual compound corresponds in each case to one line of table A1.

Table 296l: Compounds 4771a to 4800a of formula I, wherein $X^1$, $X^2$ and $R^1$ are defined as in line P-160 of table P and the meaning of $R^2$ for each individual compound corresponds in each case to one line of table A1.

Table 296m: Compounds 4801a to 4830a of formula I, wherein $X^1$, $X^2$ and $R^1$ are defined as in line P-161 of table P and the meaning of $R^2$ for each individual compound corresponds in each case to one line of table A1.

Table 296n: Compounds 4831a to 4860a of formula I, wherein $X^1$, $X^2$ and $R^1$ are defined as in line P-162 of table P and the meaning of $R^2$ for each individual compound corresponds in each case to one line of table A1.

Table 296o: Compounds 4861a to 4890a of formula I, wherein $X^1$, $X^2$ and $R^1$ are defined as in line P-163 of table P and the meaning of $R^2$ for each individual compound corresponds in each case to one line of table A1.

Table 296p: Compounds 4891a to 4920a of formula I, wherein $X^1$, $X^2$ and $R^1$ are defined as in line P-164 of table P and the meaning of $R^2$ for each individual compound corresponds in each case to one line of table A1.

Table 296q: Compounds 4921a to 4950a of formula I, wherein $X^1$, $X^2$ and $R^1$ are defined as in line P-165 of table P and the meaning of $R^2$ for each individual compound corresponds in each case to one line of table A1.

Table 296r: Compounds 4951a to 4980a of formula I, wherein $X^1$, $X^2$ and $R^1$ are defined as in line P-166 of table P and the meaning of $R^2$ for each individual compound corresponds in each case to one line of table A1.

Table 296s: Compounds 4981a to 5010a of formula I, wherein $X^1$, $X^2$ and $R^1$ are defined as in line P-167 of table P and the meaning of $R^2$ for each individual compound corresponds in each case to one line of table A1.

Table 296t: Compounds 5011a to 5040a of formula I, wherein $X^1$, $X^2$ and $R^1$ are defined as in line P-168 of table P and the meaning of $R^2$ for each individual compound corresponds in each case to one line of table A1.

Table 296u: Compounds 5041a to 5070a of formula I, wherein $X^1$, $X^2$ and $R^1$ are defined as in line P-169 of table P and the meaning of $R^2$ for each individual compound corresponds in each case to one line of table A1.

Table 296v: Compounds 5071a to 5100a of formula I, wherein $X^1$, $X^2$ and $R^1$ are defined as in line P-170 of table P and the meaning of $R^2$ for each individual compound corresponds in each case to one line of table A1.

Table 296w: Compounds 5101a to 5130a of formula I, wherein $X^1$, $X^2$ and $R^1$ are defined as in line P-171 of table P and the meaning of $R^2$ for each individual compound corresponds in each case to one line of table A1.

Table 296x: Compounds 5131a to 5160a of formula I, wherein $X^1$, $X^2$ and $R^1$ are defined as in line P-172 of table P and the meaning of $R^2$ for each individual compound corresponds in each case to one line of table A1.

Table 296y: Compounds 5161a to 5190a of formula I, wherein $X^1$, $X^2$ and $R^1$ are defined as in line P-173 of table P and the meaning of $R^2$ for each individual compound corresponds in each case to one line of table A1.

Table 296z: Compounds 5191a to 5220a of formula I, wherein $X^1$, $X^2$ and $R^1$ are defined as in line P-174 of table P and the meaning of $R^2$ for each individual compound corresponds in each case to one line of table A1.

Table 296aa: Compounds 5221a to 5250a of formula I, wherein $X^1$, $X^2$ and $R^1$ are defined as in line P-175 of table P and the meaning of $R^2$ for each individual compound corresponds in each case to one line of table A1.
Table 296bb: Compounds 5251a to 5280a of formula I, wherein $X^1$, $X^2$ and $R^1$ are defined as in line P-176 of table P and the meaning of $R^2$ for each individual compound corresponds in each case to one line of table A1.
Table 296cc: Compounds 5281a to 5310a of formula I, wherein $X^1$, $X^2$ and $R^1$ are defined as in line P-177 of table P and the meaning of $R^2$ for each individual compound corresponds in each case to one line of table A1.
Table 296dd: Compounds 5311a to 5340a of formula I, wherein $X^1$, $X^2$ and $R^1$ are defined as in line P-178 of table P and the meaning of $R^2$ for each individual compound corresponds in each case to one line of table A1.
Table 296ee: Compounds 5441a to 5370a of formula I, wherein $X^1$, $X^2$ and $R^1$ are defined as in line P-179 of table P and the meaning of $R^2$ for each individual compound corresponds in each case to one line of table A1.
Table 296ff: Compounds 5371a to 5400a of formula I, wherein $X^1$, $X^2$ and $R^1$ are defined as in line P-180 of table P and the meaning of $R^2$ for each individual compound corresponds in each case to one line of table A1.
Table 296gg: Compounds 5401a to 5430a of formula I, wherein $X^1$, $X^2$ and $R^1$ are defined as in line P-181 of table P and the meaning of $R^2$ for each individual compound corresponds in each case to one line of table A1.
Table 296hh: Compounds 5431a to 5460a of formula I, wherein $X^1$, $X^2$ and $R^1$ are defined as in line P-182 of table P and the meaning of $R^2$ for each individual compound corresponds in each case to one line of table A1.
Table 296ii: Compounds 5461a to 5490a of formula I, wherein $X^1$, $X^2$ and $R^1$ are defined as in line P-183 of table P and the meaning of $R^2$ for each individual compound corresponds in each case to one line of table A1.
Table 296jj: Compounds 5491a to 5520a of formula I, wherein $X^1$, $X^2$ and $R^1$ are defined as in line P-184 of table P and the meaning of $R^2$ for each individual compound corresponds in each case to one line of table A1.

TABLE A

| line | $R^2$ |
|---|---|
| A-1 | $CH_3$ |
| A-2 | $CH_2CH_3$ |
| A-3 | $CH_2CH_2CH_3$ |
| A-4 | $CH(CH_3)_2$ |
| A-5 | $C(CH_3)_3$ |
| A-6 | $CH_2CH_2CH_2CH_3$ |
| A-7 | $C_3H_5$ |
| A-8 | $C_5H_9$ |
| A-9 | $C_6H_{11}$ |
| A-10 | $C_6H_5$ |
| A-11 | $CH_2-C_6H_5$ |
| A-12 | $CH_2-C_3H_5$ |
| A-13 | $CF_3$ |
| A-14 | $CHF_2$ |
| A-15 | $CH_2-CN$ |
| A-16 | $CH_2CH_2-CN$ |
| A-17 | $C\equiv CH$ |
| A-18 | $C\equiv CCH_3$ |
| A-19 | $CH_2C\equiv CH$ |
| A-20 | $4\text{-F}-C_6H_4$ |
| A-21 | $4\text{-Cl}-C_6H_4$ |
| A-22 | $2,4\text{-Cl}_2-C_6H_3$ |
| A-23 | $2,4,6\text{-Cl}_3-C_6H_2$ |
| A-24 | $2,4,6\text{-F}_3-C_6H_2$ |
| A-25 | $CH_2-C_6H_5$ |
| A-26 | $CH_2\text{-}(4\text{-F}-C_6H_4)$ |
| A-27 | $CH_2\text{-}(4\text{-Cl}-C_6H_4)$ |
| A-28 | $CH=CH-C_6H_5$ |
| A-29 | $CH=CH\text{-}(4\text{-F}-C_6H_4)$ |
| A-30 | $CH=CH\text{-}(4\text{-Cl}-C_6H_4)$ |

TABLE A1

| line | $R^2$ |
|---|---|
| A1-1 | $CH_2CH=CH_2$ |
| A1-2 | $CH_2C\equiv CCH_3$ |
| A1-3 | $CH_2OCH_3$ |
| A1-4 | $CH_2OC_2H_5$ |
| A1-5 | $CH_2CH_2OCH_3$ |
| A1-6 | $CH_2C(CH_3)=CH_2$ |
| A1-7 | $CH_2\text{-}(4\text{-OCH}_3-C_6H_4)$ |
| A1-8 | $CH_2\text{-}(4\text{-CH}_3-C_6H_4)$ |
| A1-9 | $CH_2Cl$ |
| A1-10 | $CH_2CH_2Cl$ |
| A1-11 | $CH_2C\equiv CCH_2CH_3$ |
| A1-12 | $CH_2C\equiv CCH(CH_3)_2$ |
| A1-13 | $CH_2C\equiv CC(CH_3)_3$ |
| A1-14 | $CH_2CH_2CH_2Cl$ |
| A1-15 | $CH_2C\equiv CCl$ |
| A1-16 | $CH_2CH=CHCH_3$ |
| A1-17 | $CH_2CH=CHCH_2CH_3$ |
| A1-18 | $CH_2C\equiv CC(CH_3)_3$ |
| A1-19 | $C(CH_3)=CH_2$ |
| A1-20 | $CH_2CH_2CF_3$ |
| A1-21 | $CH(CH_3)CH_2CH_3$ |
| A1-22 | $CH_2CH(CH_3)_2$ |
| A1-23 | $CH_2CH(CH_3)CH_2CH_3$ |
| A1-24 | $CH_2CH_2CH(CH_3)_2$ |
| A1-25 | $CH_2CH(OCH_3)CH_3$ |
| A1-26 | $CH_2CH_2CH_2CH_2CH_3$ |
| A1-27 | $CH_2(2,4\text{-Cl}_2-C_6H_3)$ |
| A1-28 | $CH_2C(Cl)=CH_2$ |
| A1-29 | $CH_2CH=CHCl$ |
| A1-30 | $CH_2C\equiv C-CH_2OCH_3$ |

The compounds I and VIII, respectively, and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compounds I and VIII, respectively, and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e. g. conifers; and on the plant propagation material, such as seeds, and the crop material of these plants.

Preferably, compounds I and VIII, respectively, and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with compounds I and VIII, respectively, and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp).
Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as 5-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany). The compounds I and VIII, respectively, and compositions thereof, respectively, are particularly suitable for controlling the following plant diseases: *Albugo* spp. (white rust) on ornamentals, vegetables (e. g. *A. candida*) and sunflowers (e. g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (*B. sorokiniana*) on cereals and e.g. *B. oryzae* on rice and turfs; *Blumeria* (formerly *Erysiphe*) *graminis* (powdery mildew) on cereals (e. g. on wheat or barley); *Botrytis cinerea* (teleomorph: *Botryotinia fuckliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e.g. Gray leaf spot: *C. zeae-maydis*), rice, sugar beets (e. g. *C. beticola*), sugar cane, vegetables, coffee, soybeans (e. g. *C. solina* or *C. kikuchli*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. *C. coccodes*: black dot), beans (e. g. *C. lindemuthianum*) and soybeans (e. g. *C. truncatum* or *C. gloeosporiodes*); *Corticium* spp., e. g. *C. sasakii* blight) on rice; *Corynespora cassiicoia* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectna* spp.) on fruit trees, vines (e. g. *C. liriodendri*, teleomorph: *Neonectria liriodendri*: Black Foot Disease) and ornamentals; *Dematophora* (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici-repentis*: tan spot), rice and turf; Esca (dieback, apoplexy) on vines, caused by *Formitiporia* (syn. *Phellinus*) *punctata*, *F. mediterranea*, *Phaeomonielia chlamydospora* (earlier *Phaeoacremonlum chlamydosporum*), *Phaeoacremonlum aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e. g. *E. pisi*), such as cucurbits (e. g. *E. cichoracearum*), cabbages, rape (e.g. *E. cruciferarum*); *Eutypa lata* (*Eutypa* canker or dieback, anamorph: *Cytosporina lata*, syn. *Libertelia blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* on soybeans and *F. verticilliodes* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella angulata* on vines, pome fruits and other plants and *G. gossypii* on cotton; Grain-staining complex on rice; *Guignardia bewellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix*(coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa, M. fructicoia* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici, Septoria* blotch) on wheat or *M. fijiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e.g. *P. tracheiphda* and *P.*

*tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; *Pseudopezicula tracheiphda* (red fire disease or 'rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnli* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e. g. *P. oryzae* (teleomorph: *Magnaporthe grisea*, rice blast) on rice and *P. gnisea* on turf and cereals; *Pythium* spp. (damping-off) on turf, rice, corn, wheat, cotton, rape, sunflowers, soybeans, sugar beets, vegetables and various other plants (e. g. *P. ultirnum* or *P. aphanidermatum*); *Ramulana* spp., e. g. *R. collocygni* (Ramularia leaf spots, Physiological leaf spots) on barley and *R. beticola* on sugar beets; *Rhizoctoma* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticafe; *Sarocladium oryzae* and *S. attenuatum* (sheath rot) on rice; *Sclerotima* spp. (stem rot or white mold) on vegetables and field crops, such as rape, sunflowers (e. g. *S. sclerotiorum*) and soybeans (e. g. *S. rolfsll* or *S. sclerotiorum*); *Septona* spp. on various plants, e. g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oldium tuckeri*) on vines; *Setospaena* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: Leptosphaena [syn. *Phaeosphaena] nodorum*) on wheat; *Synchytrium endobioticum* on potatoes (potato wart disease); *Taphnna* spp., e. g. T. deformans (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. T caries, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Ventuna* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds I and VIII, respectively, and compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasldlum pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Pona* spp., *Serpula* spp. and *Tyromyces* spp., Deuteromycetes such as *Aspergillus* spp., *Cladosporium* spp., *Penicillium* spp., *Trichorma* spp., *Alternana* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The compounds I and VIII, respectively, and compositions thereof, resepectively, may be used for improving the health of a plant. The invention also relates to a method for improving plant health by treating a plant, its propagation material and/or the locus where the plant is growing or is to grow with an effective amount of compounds I and VIII, respectively, and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compounds of formula I and VIII, respectively, can be present in different crystal modifications whose biological activity may differ. They are likewise subject matter of the present invention.

The compounds I and VIII, respectively, are employed as such or in form of compositions by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compounds I and VIII, respectively, as such or a composition comprising at least one compound I and VIII, respectively, prophylactically either at or before planting or transplanting.

The invention also relates to agrochemical compositions comprising an auxiliary and at least one compound I or VIII, respectively, according to the invention.

An agrochemical composition comprises a fungicidally effective amount of a compound I or VIII, respectively. The term "effective amount" denotes an amount of the composition or of the compounds I or VIII, respectively, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I or VIII, respectively, used.

The compounds I and VIII, respectively, their N-oxides and salts can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I or VIII, respectively, and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a compound I or VIII, respectively, and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a compound I or VIII, respectively, and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a compound I or VIII, respectively, and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound I or VIII, respectively, are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I or VIII, respectively, are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I or VIII, respectively, are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I or VIII, respectively, are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I or VIII, respectively, are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I or VIII, respectively, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly (meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a compound I or VIII, respectively, are ground finely and mixed intimately with solid carrier (e.g. finely divided kaolin) ad 100 wt %.

x) Granules (GR, FG)

0.5-30 wt % of a compound I or VIII, respectively, is ground finely and associated with solid carrier (e.g. silicate) ad 100 wt %. Granulation is achieved by extrusion, spray-drying or fluidized bed.

xi) Ultra-Low Volume Liquids (UL)

1-50 wt % of a compound I or VIII, respectively, are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I or VIII, respectively, and compositions thereof, respectively, on to plant propagation material, especially seeds include dressing, coating, pelleting, dusting, soaking and in-furrow application methods of the propagation material. Preferably, compound I or VIII, respectively, or the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

Mixing the compounds I or VIII, respectively, or the compositions comprising them in the use form as fungicides with other fungicides results in many cases in an expansion of the fungicidal spectrum of activity being obtained or in a prevention of fungicide resistance development. Furthermore, in many cases, synergistic effects are obtained.

The following list of active substances, in conjunction with which the compounds I or VIII, respectively, can be used, is intended to illustrate the possible combinations but does not limit them:

A) Respiration Inhibitors
  Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl) phenyl)-2-methoxyimino-N-methyl-acetamide, pyribencarb, triclopyricarb/chlorodincarb, famoxadone, fenamidone;
  inhibitors of complex III at $Q_o$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)$_4$-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl] amino]-6-methyl-4,9-dioxo-8-(phenylmethyl)-1,5-dioxonan-7-yl 2-methylpropanoate;
  inhibitors of complex II (e.g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-tri-methyl-N-(1,1,3-trimethylindan-4-yl)pyrazole-4-carboxamide;
  other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)
  C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizol; pyrimidines, pyridines and piperazines: fenarimol, nuarimol, pyrifenox, triforine;
  Delta14-reductase inhibitors: aldimorph, dodemorph, dodemorph-acetate, fenpropimorph, tridemorph, fenpropidin, piperalin, spiroxamine;
  Inhibitors of 3-keto reductase: fenhexamid;

C) Nucleic Acid Synthesis Inhibitors
  phenylamides or acyl amino acid fungicides: benalaxyl, benalaxyl-M, kiralaxyl, metalaxyl, metalaxyl-M (mefenoxam), ofurace, oxadixyl;
  others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy) pyrimidin-4-amine;

D) Inhibitors of Cell Division and Cytoskeleton
  tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of Amino Acid and Protein Synthesis
methionine synthesis inhibitors (anilino-pyrimidines): cyprodinil, mepanipyrim, pyrimethanil;
protein synthesis inhibitors: blasticidin-S, kasugamycin, kasugamycin hydrochloridehydrate, mildiomycin, streptomycin, oxytetracyclin, polyoxine, validamycin A;

F) Signal Transduction Inhibitors
MAP/histidine kinase inhibitors: fluoroimid, iprodione, procymidone, vinclozolin, fenpiclonil, fludioxonil;
G protein inhibitors: quinoxyfen;

G) Lipid and Membrane Synthesis Inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;
compounds affecting cell membrane permeability and fatty acides: propamocarb, propamocarb-hydrochlorid
fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;

H) Inhibitors with Multi Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatineacetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)tetraone;

I) Cell Wall Synthesis Inhibitors
inhibitors of glucan synthesis: validamycin, polyoxin B;
melanin synthesis inhibitors: pyroquilon, tricyclazole, carpropamid, dicyclomet, fenoxanil;

J) Plant Defence Inducers
acibenzolar-S-methyl, probenazole, isotianil, tiadinil, prohexadione-calcium; phosphonates: fosetyl, fosetyl-aluminum, phosphorous acid and its salts;

K) Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropyl-methoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxyacetamide;

L) Antifungal biocontrol agents, plant bioactivators: *Ampelomyces quisqualie* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilise* var. *amyloliquefaciens* FZB24 (e.g. TAEGRO® from Novozyme Biologicals, Inc., USA), *Candida oleophila* 1-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Clyphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutna sachlinensie* (e.g. REGALIA® from Marrone BioInnovations, USA), *Talaromyces flavus* V117b (e.g. PROTUS® from Prophyta, Germany), *Trichoderma asperellum* SKT-1 (e.g. ECOHOPE® from Kumiai Chemical Industry Co., Ltd., Japan), *T. atroviride* LC52 (e.g. SENTINEL® from Agrimm Technologies Ltd, NZ), *T. harzianum*T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB BioInnovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), T vindeTV1 (e.g. *T. viride* TV1 from Agribiotec srl, Italy), *Ulocladium oudemansii* HRU3 (e.g. BOTRY-ZEN® from Botry-Zen Ltd, NZ);

M) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Herbicides acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate;

pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b] pyridazin-3-yOsulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

The present invention furthermore relates to agrochemical compositions comprising a mixture of at least one compound I or VIII, respectively, (component 1) and at least one further active substance useful for plant protection, e. g. selected from the groups A) to O) (component 2), in particular one further fungicide, e. g. one or more fungicide from the groups A) to L), as described above, and if desired one suitable solvent or solid carrier. Those mixtures are of particular interest, since many of them at the same application rate show higher efficiencies against harmful fungi. Furthermore, combating harmful fungi with a mixture of compounds I or VIII, respectively, and at least one fungicide from groups A) to L), as described above, is more efficient than combating those fungi with individual compounds I or VIII, respectively, or individual fungicides from groups A) to L). By applying compounds I or VIII, respectively, together with at least one active substance from groups A) to O) a synergistic effect can be obtained, i.e. more then simple addition of the individual effects is obtained (synergistic mixtures).

This can be obtained by applying the compounds I or VIII, respectively, and at least one further active substance simultaneously, either jointly (e. g. as tank-mix) or seperately, or in succession, wherein the time interval between the individual applications is selected to ensure that the active substance applied first still occurs at the site of action in a sufficient amount at the time of application of the further active substance(s). The order of application is not essential for working of the present invention.

In binary mixtures, i.e. compositions according to the invention comprising one compound I or VIII, respectively, (component 1) and one further active substance (component 2), e. g. one active substance from groups A) to O), the weight ratio of component 1 and component 2 generally depends from the properties of the active substances used, usually it is in the range of from 1:100 to 100:1, regularly in the range of from 1:50 to 50:1, preferably in the range of from 1:20 to 20:1, more preferably in the range of from 1:10 to 10:1 and in particular in the range of from 1:3 to 3:1.

In ternary mixtures, i.e. compositions according to the invention comprising one compound I or VIII, respectively, (component 1) and a first further active substance (component 2) and a second further active substance (component 3), e. g. two active substances from groups A) to O), the weight ratio of component 1 and component 2 depends from the properties of the active substances used, preferably it is in the range of from 1:50 to 50:1 and particularly in the range of from 1:10 to 10:1, and the weight ratio of component 1 and component 3 preferably is in the range of from 1:50 to 50:1 and particularly in the range of from 1:10 to 10:1.

Preference is also given to mixtures comprising a compound I or VIII, respectively, (component 1) and at least one active substance selected from group A) (component 2) and particularly selected from azoxystrobin, dimoxystrobin, fluoxastrobin, kresoxim-methyl, orysastrobin, picoxystrobin, pyraclostrobin, trifloxystrobin; famoxadone, fenamidone; bixafen, boscalid, fluopyram, fluxapyroxad, isopyrazam, penflufen, penthiopyrad, sedaxane; ametoctradin, cyazofamid, fluazinam, fentin salts, such as fentin acetate.

Preference is given to mixtures comprising a compound of formula I or VIII, respectively, (component 1) and at least one active substance selected from group B) (component 2) and particularly selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol, triforine; dodemorph, fenpropimorph, tridemorph, fenpropidin, spiroxamine; fenhexamid.

Preference is given to mixtures comprising a compound of formula I or VIII, respectively, (component 1) and at least one active substance selected from group C) (component 2) and particularly selected from metalaxyl, (metalaxyl-M) mefenoxam, ofurace.

Preference is given to mixtures comprising a compound of formula I or VIII, respectively, (component 1) and at least one active substance selected from group D) (component 2) and particularly selected from benomyl, carbendazim, thiophanate-methyl, ethaboxam, fluopicolide, zoxamide, metrafenone, pyriofenone.

Preference is also given to mixtures comprising a compound I or VIII, respectively, (component 1) and at least one active substance selected from group E) (component 2) and particularly selected from cyprodinil, mepanipyrim, pyrimethanil.

Preference is also given to mixtures comprising a compound I or VIII, respectively, (component 1) and at least one active substance selected from group F) (component 2) and particularly selected from iprodione, fludioxonil, vinclozolin, quinoxyfen.

Preference is also given to mixtures comprising a compound I or VIII, respectively, (component 1) and at least one active substance selected from group G) (component 2) and particularly selected from dimethomorph, flumorph, iprovalicarb, benthiavalicarb, mandipropamid, propamocarb.

Preference is also given to mixtures comprising a compound I or VIII, respectively, (component 1) and at least one active substance selected from group H) (component 2) and particularly selected from copper acetate, copper hydroxide, copper oxychloride, copper sulfate, sulfur, mancozeb, metiram, propineb, thiram, captafol, folpet, chlorothalonil, dichlofluanid, dithianon.

Preference is also given to mixtures comprising a compound I or VIII, respectively, (component 1) and at least one active substance selected from group I) (component 2) and particularly selected from carpropamid and fenoxanil.

Preference is also given to mixtures comprising a compound I or VIII, respectively, (component 1) and at least one active substance selected from group J) (component 2) and particularly selected from acibenzolar-S-methyl, probenazole, tiadinil, fosetyl, fosetyl-aluminium, H$_3$P0$_3$ and salts thereof.

Preference is also given to mixtures comprising a compound I or VIII, respectively, (component 1) and at least one active substance selected from group K) (component 2) and particularly selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydro-naphthalen-1-yl]-4-thiazolecarboxamide.

Preference is also given to mixtures comprising a compound I or VIII, respectively, (component 1) and at least one active substance selected from group L) (component 2) and particularly selected from *Bacillus subtilis* strain NRRL No. B-21661, *Bacillus pumllus* strain NRRL No. B-30087 and *Ulocladium oudemansii*.

Accordingly, the present invention furthermore relates to compositions comprising one compound I or VIII, respectively, (component 1) and one further active substance (component 2), which further active substance is selected from the column "Component 2" of the lines B-1 to B-372 of Table B.

A further embodiment relates to the compositions B-1 to B-372 listed in Table B, where a row of Table B corresponds in each case to a fungicidal composition comprising one of the in the present specification individualized compounds of formula I (component 1) and the respective further active substance from groups A) to O) (component 2) stated in the row in question. Preferably, the compositions described comprise the active substances in synergistically effective amounts.

TABLE B

Composition comprising one indiviualized compound I and one further active substance from groups A) to O)

| Mixture | Component 1 | Component 2 |
| --- | --- | --- |
| B-1 | one individualized compound I | Azoxystrobin |
| B-2 | one individualized compound I | Coumethoxystrobin |
| B-3 | one individualized compound I | Coumoxystrobin |
| B-4 | one individualized compound I | Dimoxystrobin |
| B-5 | one individualized compound I | Enestroburin |
| B-6 | one individualized compound I | Fenaminstrobin |
| B-7 | one individualized compound I | Fenoxystrobin/Flufenoxystrobin |
| B-8 | one individualized compound I | Fluoxastrobin |
| B-9 | one individualized compound I | Kresoxim-methyl |
| B-10 | one individualized compound I | Metominostrobin |
| B-11 | one individualized compound I | Orysastrobin |
| B-12 | one individualized compound I | Picoxystrobin |
| B-13 | one individualized compound I | Pyraclostrobin |
| B-14 | one individualized compound I | Pyrametostrobin |
| B-15 | one individualized compound I | Pyraoxystrobin |
| B-16 | one individualized compound I | Pyribencarb |
| B-17 | one individualized compound I | Trifloxystrobin |
| B-18 | one individualized compound I | Triclopyricarb/Chlorodincarb |
| B-19 | one individualized compound I | 2-[2-(2,5-dimethyl-phenoxymethyl)-phenyl]-3-methoxy-acrylic acid methyl ester |
| B-20 | one individualized compound I | 2-(2-(3-(2,6-dichlorophenyl)-1-methyl-allylideneaminooxymethyl)-phenyl)-2-methoxyimino-N-methyl-acetamide |
| B-21 | one individualized compound I | Benalaxyl |
| B-22 | one individualized compound I | Benalaxyl-M |
| B-23 | one individualized compound I | Benodanil |
| B-24 | one individualized compound I | Bixafen |
| B-25 | one individualized compound I | Boscalid |
| B-26 | one individualized compound I | Carboxin |
| B-27 | one individualized compound I | Fenfuram |
| B-28 | one individualized compound I | Fenhexamid |
| B-29 | one individualized compound I | Flutolanil |
| B-30 | one individualized compound I | Fluxapyroxad |
| B-31 | one individualized compound I | Furametpyr |
| B-32 | one individualized compound I | Isopyrazam |
| B-33 | one individualized compound I | Isotianil |
| B-34 | one individualized compound I | Kiralaxyl |
| B-35 | one individualized compound I | Mepronil |
| B-36 | one individualized compound I | Metalaxyl |
| B-37 | one individualized compound I | Metalaxyl-M |
| B-38 | one individualized compound I | Ofurace |
| B-39 | one individualized compound I | Oxadixyl |
| B-40 | one individualized compound I | Oxycarboxin |
| B-41 | one individualized compound I | Penflufen |
| B-42 | one individualized compound I | Penthiopyrad |
| B-43 | one individualized compound I | Sedaxane |
| B-44 | one individualized compound I | Tecloftalam |
| B-45 | one individualized compound I | Thifluzamide |

TABLE B-continued

Composition comprising one indiviualized compound I and one further active substance from groups A) to O)

| Mixture | Component 1 | Component 2 |
|---|---|---|
| B-46 | one individualized compound I | Tiadinil |
| B-47 | one individualized compound I | 2-Amino-4-methyl-thiazole-5-carboxylic acid anilide |
| B-48 | one individualized compound I | N-(4'-trifluoromethylthiobiphenyl-2-yl)-3-difluoromethyl-1-methyl-1H-pyrazole-4-carboxamide |
| B-49 | one individualized compound I | N-(2-(1,3,3-trimethyl-butyl)-phenyl)-1,3-dimethyl-5-fluoro-1H-pyrazole-4-carboxamide |
| B-50 | one individualized compound I | N-[9-(dichloromethylene)-1,2,3,4-tetrahydro-1,4-methanonaphthalen-5-yl]-3-(difluoromethyl)-1-methyl-1H-pyrazole-4-carboxamide |
| B-51 | one individualized compound I | Dimethomorph |
| B-52 | one individualized compound I | Flumorph |
| B-53 | one individualized compound I | Pyrimorph |
| B-54 | one individualized compound I | Flumetover |
| B-55 | one individualized compound I | Fluopicolide |
| B-56 | one individualized compound I | Fluopyram |
| B-57 | one individualized compound I | Zoxamide |
| B-58 | one individualized compound I | Carpropamid |
| B-59 | one individualized compound I | Diclocymet |
| B-60 | one individualized compound I | Mandipropamid |
| B-61 | one individualized compound I | Oxytetracyclin |
| B-62 | one individualized compound I | Silthiofam |
| B-63 | one individualized compound I | N-(6-methoxy-pyridin-3-yl) cyclopropanecarboxylic acid amide |
| B-64 | one individualized compound I | Azaconazole |
| B-65 | one individualized compound I | Bitertanol |
| B-66 | one individualized compound I | Bromuconazole |
| B-67 | one individualized compound I | Cyproconazole |
| B-68 | one individualized compound I | Difenoconazole |
| B-69 | one individualized compound I | Diniconazole |
| B-70 | one individualized compound I | Diniconazole-M |
| B-71 | one individualized compound I | Epoxiconazole |
| B-72 | one individualized compound I | Fenbuconazole |
| B-73 | one individualized compound I | Fluquinconazole |
| B-74 | one individualized compound I | Flusilazole |
| B-75 | one individualized compound I | Flutriafol |
| B-76 | one individualized compound I | Hexaconazol |
| B-77 | one individualized compound I | Imibenconazole |
| B-78 | one individualized compound I | Ipconazole |
| B-79 | one individualized compound I | Metconazole |
| B-80 | one individualized compound I | Myclobutanil |
| B-81 | one individualized compound I | Oxpoconazol |
| B-82 | one individualized compound I | Paclobutrazol |
| B-83 | one individualized compound I | Penconazole |
| B-84 | one individualized compound I | Propiconazole |
| B-85 | one individualized compound I | Prothioconazole |
| B-86 | one individualized compound I | Simeconazole |
| B-87 | one individualized compound I | Tebuconazole |
| B-88 | one individualized compound I | Tetraconazole |
| B-89 | one individualized compound I | Triadimefon |
| B-90 | one individualized compound I | Triadimenol |
| B-91 | one individualized compound I | Triticonazole |
| B-92 | one individualized compound I | Uniconazole |
| B-93 | one individualized compound I | Cyazofamid |
| B-94 | one individualized compound I | Imazalil |
| B-95 | one individualized compound I | Imazalil-sulfate |
| B-96 | one individualized compound I | Pefurazoate |
| B-97 | one individualized compound I | Prochloraz |
| B-98 | one individualized compound I | Triflumizole |
| B-99 | one individualized compound I | Benomyl |
| B-100 | one individualized compound I | Carbendazim |
| B-101 | one individualized compound I | Fuberidazole |
| B-102 | one individualized compound I | Thiabendazole |
| B-103 | one individualized compound I | Ethaboxam |
| B-104 | one individualized compound I | Etridiazole |
| B-105 | one individualized compound I | Hymexazole |
| B-106 | one individualized compound I | 2-(4-Chloro-phenyl)-N-[4-(3,4-dimethoxy-phenyl)-isoxazol-5-yl]-2-prop-2-ynyloxy-acetamide |

TABLE B-continued

Composition comprising one indiviualized compound I and one further active substance from groups A) to O)

| Mixture | Component 1 | Component 2 |
|---|---|---|
| B-107 | one individualized compound I | Fluazinam |
| B-108 | one individualized compound I | Pyrifenox |
| B-109 | one individualized compound I | 3-[5-(4-Chloro-phenyl)-2,3-dimethyl-isoxazolidin-3-yl]-pyridine (Pyrisoxazole) |
| B-110 | one individualized compound I | 3-[5-(4-Methyl-phenyl)-2,3-dimethyl-isoxazolidin-3-yl]-pyridine |
| B-111 | one individualized compound I | Bupirimate |
| B-112 | one individualized compound I | Cyprodinil |
| B-113 | one individualized compound I | 5-Fluorocytosine |
| B-114 | one individualized compound I | 5-Fluoro-2-(p-tolylmethoxy)pyrimidin-4-amine |
| B-115 | one individualized compound I | 5-Fluoro-2-(4-fluorophenylmethoxy)-pyrimidin-4-amine |
| B-116 | one individualized compound I | Diflumetorim |
| B-117 | one individualized compound I | (5,8-Difluoroquinazolin-4-yl)-{2-[2-fluoro-4-(4-trifluoromethylpyridin-2-yloxy)-phenyl]-ethyl}-amine |
| B-118 | one individualized compound I | Fenarimol |
| B-119 | one individualized compound I | Ferimzone |
| B-120 | one individualized compound I | Mepanipyrim |
| B-121 | one individualized compound I | Nitrapyrin |
| B-122 | one individualized compound I | Nuarimol |
| B-123 | one individualized compound I | Pyrimethanil |
| B-124 | one individualized compound I | Triforine |
| B-125 | one individualized compound I | Fenpiclonil |
| B-126 | one individualized compound I | Fludioxonil |
| B-127 | one individualized compound I | Aldimorph |
| B-128 | one individualized compound I | Dodemorph |
| B-129 | one individualized compound I | Dodemorph-acetate |
| B-130 | one individualized compound I | Fenpropimorph |
| B-131 | one individualized compound I | Tridemorph |
| B-132 | one individualized compound I | Fenpropidin |
| B-133 | one individualized compound I | Fluoroimid |
| B-134 | one individualized compound I | Iprodione |
| B-135 | one individualized compound I | Procymidone |
| B-136 | one individualized compound I | Vinclozolin |
| B-137 | one individualized compound I | Famoxadone |
| B-138 | one individualized compound I | Fenamidone |
| B-139 | one individualized compound I | Flutianil |
| B-140 | one individualized compound I | Octhilinone |
| B-141 | one individualized compound I | Probenazole |
| B-142 | one individualized compound I | Fenpyrazamine |
| B-143 | one individualized compound I | Acibenzolar-S-methyl |
| B-144 | one individualized compound I | Ametoctradin |
| B-145 | one individualized compound I | Amisulbrom |
| B-146 | one individualized compound I | [(3S,6S,7R,8R)-8-benzyl-3-[(3-isobutyryloxymethoxy-4-methoxypyridine-2-carbonyl)amino]-6-methyl-4,9-dioxo-[1,5]dioxonan-7-yl] 2-methylpropanoate |
| B-147 | one individualized compound I | [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate |
| B-148 | one individualized compound I | [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate |
| B-149 | one individualized compound I | [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate |
| B-150 | one individualized compound I | [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methyl-propanoate |
| B-151 | one individualized compound I | Anilazin |
| B-152 | one individualized compound I | Blasticidin-S |
| B-153 | one individualized compound I | Captafol |
| B-154 | one individualized compound I | Captan |
| B-155 | one individualized compound I | Chinomethionat |
| B-156 | one individualized compound I | Dazomet |
| B-157 | one individualized compound I | Debacarb |
| B-158 | one individualized compound I | Diclomezine |
| B-159 | one individualized compound I | Difenzoquat, |

TABLE B-continued

Composition comprising one indiviualized compound I and one further active substance from groups A) to O)

| Mixture | Component 1 | Component 2 |
|---|---|---|
| B-160 | one individualized compound I | Difenzoquat-methylsulfate |
| B-161 | one individualized compound I | Fenoxanil |
| B-162 | one individualized compound I | Folpet |
| B-163 | one individualized compound I | Oxolinsaure |
| B-164 | one individualized compound I | Piperalin |
| B-165 | one individualized compound I | Proquinazid |
| B-166 | one individualized compound I | Pyroquilon |
| B-167 | one individualized compound I | Quinoxyfen |
| B-168 | one individualized compound I | Triazoxid |
| B-169 | one individualized compound I | Tricyclazole |
| B-170 | one individualized compound I | 2-Butoxy-6-iodo-3-propyl-chromen-4-one |
| B-171 | one individualized compound I | 5-Chloro-1-(4,6-dimethoxy-pyrimidin-2-yl)-2-methyl-1H-benzoimidazole |
| B-172 | one individualized compound I | 5-Chloro-7-(4-methyl-piperidin-1-yl)-6-(2,4,6-trifluoro-phenyl)-[1,2,4]triazolo[1,5-a]pyrimidine |
| B-173 | one individualized compound I | Ferbam |
| B-174 | one individualized compound I | Mancozeb |
| B-175 | one individualized compound I | Maneb |
| B-176 | one individualized compound I | Metam |
| B-177 | one individualized compound I | Methasulphocarb |
| B-178 | one individualized compound I | Metiram |
| B-179 | one individualized compound I | Propineb |
| B-180 | one individualized compound I | Thiram |
| B-181 | one individualized compound I | Zineb |
| B-182 | one individualized compound I | Ziram |
| B-183 | one individualized compound I | Diethofencarb |
| B-184 | one individualized compound I | Benthiavalicarb |
| B-185 | one individualized compound I | Iprovalicarb |
| B-186 | one individualized compound I | Propamocarb |
| B-187 | one individualized compound I | Propamocarb hydrochlorid |
| B-188 | one individualized compound I | Valifenalate |
| B-189 | one individualized compound I | N-(1-(1-(4-cyanophenyl)ethanesulfonyl)-but-2-yl) carbamic acid-(4-fluoro-phenyl) ester |
| B-190 | one individualized compound I | Dodine |
| B-191 | one individualized compound I | Dodine free base |
| B-192 | one individualized compound I | Guazatine |
| B-193 | one individualized compound I | Guazatine-acetate |
| B-194 | one individualized compound I | Iminoctadine |
| B-195 | one individualized compound I | Iminoctadine-triacetate |
| B-196 | one individualized compound I | Iminoctadine-tris(albesilate) |
| B-197 | one individualized compound I | Kasugamycin |
| B-198 | one individualized compound I | Kasugamycin-hydrochloride-hydrate |
| B-199 | one individualized compound I | Polyoxine |
| B-200 | one individualized compound I | Streptomycin |
| B-201 | one individualized compound I | Validamycin A |
| B-202 | one individualized compound I | Binapacryl |
| B-203 | one individualized compound I | Dicloran |
| B-204 | one individualized compound I | Dinobuton |
| B-205 | one individualized compound I | Dinocap |
| B-206 | one individualized compound I | Nitrothal-isopropyl |
| B-207 | one individualized compound I | Tecnazen |
| B-208 | one individualized compound I | Fentin salts |
| B-209 | one individualized compound I | Dithianon |
| B-210 | one individualized compound I | Isoprothiolane |
| B-211 | one individualized compound I | Edifenphos |
| B-212 | one individualized compound I | Fosetyl, Fosetyl-aluminium |
| B-213 | one individualized compound I | Iprobenfos |
| B-214 | one individualized compound I | Phosphorous acid ($H_3PO_3$) and derivatives |
| B-215 | one individualized compound I | Pyrazophos |
| B-216 | one individualized compound I | Tolclofos-methyl |
| B-217 | one individualized compound I | Chlorothalonil |
| B-218 | one individualized compound I | Dichlofluanid |
| B-219 | one individualized compound I | Dichlorophen |
| B-220 | one individualized compound I | Flusulfamide |
| B-221 | one individualized compound I | Hexachlorbenzene |
| B-222 | one individualized compound I | Pencycuron |
| B-223 | one individualized compound I | Pentachlorophenol and salts |
| B-224 | one individualized compound I | Phthalide |
| B-225 | one individualized compound I | Quintozene |
| B-226 | one individualized compound I | Thiophanate Methyl |
| B-227 | one individualized compound I | Tolylfluanid |
| B-228 | one individualized compound I | N-(4-chloro-2-nitro-phenyl)-N-ethyl- |

TABLE B-continued

Composition comprising one indiviualized compound I and one further active substance from groups A) to O)

| Mixture | Component 1 | Component 2 |
|---|---|---|
| | | 4-methyl-benzenesulfonamide |
| B-229 | one individualized compound I | Bordeaux mixture |
| B-230 | one individualized compound I | Copper acetate |
| B-231 | one individualized compound I | Copper hydroxide |
| B-232 | one individualized compound I | Copper oxychloride |
| B-233 | one individualized compound I | basic Copper sulfate |
| B-234 | one individualized compound I | Sulfur |
| B-235 | one individualized compound I | Biphenyl |
| B-236 | one individualized compound I | Bronopol |
| B-237 | one individualized compound I | Cyflufenamid |
| B-238 | one individualized compound I | Cymoxanil |
| B-239 | one individualized compound I | Diphenylamin |
| B-240 | one individualized compound I | Metrafenone |
| B-241 | one individualized compound I | Pyriofenone |
| B-242 | one individualized compound I | Mildiomycin |
| B-243 | one individualized compound I | Oxin-copper |
| B-244 | one individualized compound I | Prohexadione calcium |
| B-245 | one individualized compound I | Spiroxamine |
| B-246 | one individualized compound I | Tebufloquin |
| B-247 | one individualized compound I | Tolylfluanid |
| B-248 | one individualized compound I | N-(Cyclopropylmethoxyimino-(6-difluoromethoxy-2,3-difluoro-phenyl)-methyl)-2-phenyl acetamide |
| B-249 | one individualized compound I | N'-(4-(4-chloro-3-trifluoromethyl-phenoxy)-2,5-dimethyl-phenyl)-N-ethyl-N-methyl formamidine |
| B-250 | one individualized compound I | N'-(4-(4-fluoro-3-trifluoromethyl-phenoxy)-2,5-dimethyl-phenyl)-N-ethyl-N-methyl formamidine |
| B-251 | one individualized compound I | N'-(2-methyl-5-trifluoromethyl-4-(3-tri-methylsilanyl-propoxy)-phenyl)-N-ethyl-N-methyl formamidine |
| B-252 | one individualized compound I | N'-(5-difluoromethyl-2-methyl-4-(3-tri-methylsilanyl-propoxy)-phenyl)-N-ethyl-N-methyl formamidine |
| B-253 | one individualized compound I | 2-{1-[2-(5-Methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide |
| B-254 | one individualized compound I | 2-{1-[2-(5-Methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide |
| B-255 | one individualized compound I | 1-[4-[4-[5-(2,6-difluorophenyl)-4,5-di-hydro-3-isoxazolyl]-2-thiazolyl]-1-piperidinyl]-2-[5-methyl-3-(trifluoro-methyl)-1H-pyrazol-1-yl]ethanone |
| B-256 | one individualized compound I | Methoxy-acetic acid 6-tert-butyl-8-fluoro-2,3-dimethyl-quinolin-4-yl ester |
| B-257 | one individualized compound I | N-Methyl-2-{1-[(5-methyl-3-trifluoro-methyl-1H-pyrazol-1-yl)-acetyl]-piperidin-4-yl}-N-[(1R)-1,2,3,4-tetrahydro-naphthalen-1-yl]-4-thiazolecarboxamide |
| B-258 | one individualized compound I | Bacillus subtilis NRRL No. B-21661 |
| B-259 | one individualized compound I | Bacillus pumilus NRRL No. B-30087 |
| B-260 | one individualized compound I | Ulocladium oudemansii |
| B-261 | one individualized compound I | Carbaryl |
| B-262 | one individualized compound I | Carbofuran |
| B-263 | one individualized compound I | Carbosulfan |
| B-264 | one individualized compound I | Methomylthiodicarb |
| B-265 | one individualized compound I | Bifenthrin |
| B-266 | one individualized compound I | Cyfluthrin |
| B-267 | one individualized compound I | Cypermethrin |
| B-268 | one individualized compound I | alpha-Cypermethrin |
| B-269 | one individualized compound I | zeta-Cypermethrin |
| B-270 | one individualized compound I | Deltamethrin |
| B-271 | one individualized compound I | Esfenvalerate |
| B-272 | one individualized compound I | Lambda-cyhalothrin |
| B-273 | one individualized compound I | Permethrin |
| B-274 | one individualized compound I | Tefluthrin |
| B-275 | one individualized compound I | Diflubenzuron |
| B-276 | one individualized compound I | Flufenoxuron |
| B-277 | one individualized compound I | Lufenuron |

TABLE B-continued

Composition comprising one indiviualized compound I and one further active substance from groups A) to O)

| Mixture | Component 1 | Component 2 |
|---|---|---|
| B-278 | one individualized compound I | Teflubenzuron |
| B-279 | one individualized compound I | Spirotetramate |
| B-280 | one individualized compound I | Clothianidin |
| B-281 | one individualized compound I | Dinotefuran |
| B-282 | one individualized compound I | Imidacloprid |
| B-283 | one individualized compound I | Thiamethoxam |
| B-284 | one individualized compound I | Flupyradifurone |
| B-285 | one individualized compound I | Acetamiprid |
| B-286 | one individualized compound I | Thiacloprid |
| B-287 | one individualized compound I | Endosulfan |
| B-288 | one individualized compound I | Fipronil |
| B-289 | one individualized compound I | Abamectin |
| B-290 | one individualized compound I | Emamectin |
| B-291 | one individualized compound I | Spinosad |
| B-292 | one individualized compound I | Spinetoram |
| B-293 | one individualized compound I | Hydramethylnon |
| B-294 | one individualized compound I | Chlorfenapyr |
| B-295 | one individualized compound I | Fenbutatin oxide |
| B-296 | one individualized compound I | Indoxacarb |
| B-297 | one individualized compound I | Metaflumizone |
| B-298 | one individualized compound I | Flonicamid |
| B-299 | one individualized compound I | Lubendiamide |
| B-300 | one individualized compound I | Chlorantraniliprole |
| B-301 | one individualized compound I | Cyazypyr (HGW86) |
| B-302 | one individualized compound I | Cyflumetofen |
| B-303 | one individualized compound I | Acetochlor |
| B-304 | one individualized compound I | Dimethenamid |
| B-305 | one individualized compound I | metolachlor |
| B-306 | one individualized compound I | Metazachlor |
| B-307 | one individualized compound I | Glyphosate |
| B-308 | one individualized compound I | Glufosinate |
| B-309 | one individualized compound I | Sulfosate |
| B-310 | one individualized compound I | Clodinafop |
| B-311 | one individualized compound I | Fenoxaprop |
| B-312 | one individualized compound I | Fluazifop |
| B-313 | one individualized compound I | Haloxyfop |
| B-314 | one individualized compound I | Paraquat |
| B-315 | one individualized compound I | Phenmedipham |
| B-316 | one individualized compound I | Clethodim |
| B-317 | one individualized compound I | Cycloxydim |
| B-318 | one individualized compound I | Profoxydim |
| B-319 | one individualized compound I | Sethoxydim |
| B-320 | one individualized compound I | Tepraloxydim |
| B-321 | one individualized compound I | Pendimethalin |
| B-322 | one individualized compound I | Prodiamine |
| B-323 | one individualized compound I | Trifluralin |
| B-324 | one individualized compound I | Acifluorfen |
| B-325 | one individualized compound I | Bromoxynil |
| B-326 | one individualized compound I | Imazamethabenz |
| B-327 | one individualized compound I | Imazamox |
| B-328 | one individualized compound I | Imazapic |
| B-329 | one individualized compound I | Imazapyr |
| B-330 | one individualized compound I | Imazaquin |
| B-331 | one individualized compound I | Imazethapyr |
| B-332 | one individualized compound I | 2,4-Dichlorophenoxyacetic acid (2,4-D) |
| B-333 | one individualized compound I | Chloridazon |
| B-334 | one individualized compound I | Clopyralid |
| B-335 | one individualized compound I | Fluroxypyr |
| B-336 | one individualized compound I | Picloram |
| B-337 | one individualized compound I | Picolinafen |
| B-338 | one individualized compound I | Bensulfuron |
| B-339 | one individualized compound I | Chlorimuron-ethyl |
| B-340 | one individualized compound I | Cyclosulfamuron |
| B-341 | one individualized compound I | Iodosulfuron |
| B-342 | one individualized compound I | Mesosulfuron |
| B-343 | one individualized compound I | Metsulfuron-methyl |
| B-344 | one individualized compound I | Nicosulfuron |
| B-345 | one individualized compound I | Rimsulfuron |
| B-346 | one individualized compound I | Triflusulfuron |
| B-347 | one individualized compound I | Atrazine |
| B-348 | one individualized compound I | Hexazinone |
| B-349 | one individualized compound I | Diuron |
| B-350 | one individualized compound I | Florasulam |
| B-351 | one individualized compound I | Pyroxasulfone |
| B-352 | one individualized compound I | Bentazone |

TABLE B-continued

Composition comprising one indiviualized compound I and one further active substance from groups A) to O)

| Mixture | Component 1 | Component 2 |
|---|---|---|
| B-353 | one individualized compound I | Cinidon-ethyl |
| B-354 | one individualized compound I | Cinmethylin |
| B-355 | one individualized compound I | Dicamba |
| B-356 | one individualized compound I | Diflufenzopyr |
| B-357 | one individualized compound I | Quinclorac |
| B-358 | one individualized compound I | Quinmerac |
| B-359 | one individualized compound I | Mesotrione |
| B-360 | one individualized compound I | Saflufenacil |
| B-361 | one individualized compound I | Topramezone |
| B-362 | one individualized compound I | (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate |
| B-363 | one individualized compound I | [rel-(2S;3R)-3-(2-chlorophenyl)-2-(2,4-difluorophenyl)-oxiranylmethyl]-5-thiocyanato-1H-[1,2,4]triazole, |
| B-364 | one individualized compound I | 2-[rel-(2S;3R)-3-(2-chlorophenyl)-2-(2,4-difluorophenyl)-oxiranylmethyl]-2H-[1,2,4]triazole-3-thiol |
| B-365 | one individualized compound I | 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone |
| B-366 | one individualized compound I | 2,6-dimethyl-1H,5H-[1,4]dithiino[2,3-c:5,6-c']dipyrrole-1,3,5,7(2H,6H)-tetraone |
| B-367 | one individualized compound I | 3-(difluoromethyl)-1-methyl-N-(1,1,3-trimethylindan-4-yl)pyrazole-4-carboxamide |
| B-368 | one individualized compound I | 3-(trifluoromethyl)-1-methyl-N-(1,1,3-trimethylindan-4-yl)pyrazole-4-carboxamide |
| B-369 | one individualized compound I | 1,3-dimethyl-N-(1,1,3-trimethylindan-4-yl)pyrazole-4-carboxamide |
| B-370 | one individualized compound I | 3-(trifluorometh-yl)-1,5-dimethyl-N-(1,1,3-trimethylindan-4-yl)pyrazole-4-carboxamide |
| B-371 | one individualized compound I | 3-(difluoro-methyl)-1,5-dimethyl-N-(1,1,3-trimethylindan-4-yl)pyrazole-4-carboxamide |
| B-372 | one individualized compound I | 1,3,5-tri-methyl-N-(1,1,3-trimethylindan-4-yl)pyrazole-4-carboxamide |

A further embodiment relates to the compositions B2-1 to B2-372 listed in Table B2, where a row of Table B2 corresponds in each case to a fungicidal composition comprising one of the in the present specification individualized compounds of formula VIII (component 1) and the respective further active substance from groups A) to O) (component 2) stated in the row in question. Preferably, the compositions described comprise the active substances in synergistically effective amounts.

Table B2:

Composition comprising one individualized compound VIII and one further active substance from groups A) to O). This table corresponds to table B, wherein in the first column the number/name of the individualized mixture is named "B2-..." instead of "B-..." and in the second column, it says in each line "one individualized compound VIII" instead of "one individualized compound I".

The active substances referred to as component 2, their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

The mixtures of active substances can be prepared as compositions comprising besides the active ingridients at least one inert ingredient by usual means, e. g. by the means given for the compositions of compounds I.

Concerning usual ingredients of such compositions reference is made to the explanations given for the compositions containing compounds I.

The mixtures of active substances according to the present invention are suitable as fungicides, as are the compounds of formula I. They are distinguished by an outstanding effectiveness against a broad spectrum of phytopathogenic fungi, especially from the classes of the Ascomycetes, Basidiomycetes, Deuteromycetes and Peronosporomycetes (syn.

Oomycetes). In addition, it is refered to the explanations regarding the fungicidal activity of the compounds and the compositions containing compounds I, respectively.

I. Synthesis Examples

With due modification of the starting compounds, the procedures shown in the synthesis examples below were used to obtain further compounds I. The resulting compounds, together with physical data, are listed in Table I below.

The compounds I listed in Table I have been prepared in an analogous manner.

TABLE I

| ex.-no. | $X^1$ | $X^2$ | $R^1$ | $R^2$ | HPLC* $R_t$ (min) |
|---|---|---|---|---|---|
| I-1 | Cl | Cl | C≡CH | $CH_3$ | 1.24 |
| I-2 | Cl | Cl | C≡CH | $C_2H_5$ | 1.30 |
| I-3 | Cl | Cl | C≡CH | $CH_2C$≡$CH$ | 1.24 |
| I-4 | Cl | Cl | C≡CH | $CH_2C_6H_5$ | 1.38 |
| I-5 | Cl | Cl | C≡CH | $CH_2CH_2CH_3$ | 1.35 |
| I-6 | Cl | Cl | (E)CH=CHC$_6$H$_5$ | $CH_2C$≡$CH$ | 1.39 |
| I-7 | Cl | Cl | CH=CH$_2$ | $CH_3$ | 1.27 |
| I-8 | Cl | Cl | CH=CH$_2$ | $CH_2CH$=$CH_2$ | 1.35 |
| I-9 | Cl | Cl | CH=CH$_2$ | $CH_2C$≡$CH$ | 1.28 |
| I-10 | Cl | Cl | C≡CCH$_3$ | $CH_3$ | 1.28 |
| I-11 | Cl | Cl | C≡CCH$_3$ | $C_2H_5$ | 1.35 |
| I-12 | Cl | Cl | C≡CCH$_3$ | $CH_2CH$=$CH_2$ | 1.36 |
| I-13 | Cl | Cl | C≡CCH$_3$ | $CH_2C$≡$CH$ | 1.29 |
| I-14 | Cl | Cl | CH$_2$C(Cl)=CHCl | $CH_3$ | 1.09 |
| I-15 | Cl | Cl | CH$_2$C≡CH | $CH_2C$≡$CH$ | 1.24 |
| I-16 | Cl | Cl | C≡CCH$_3$ | $CH_2C(Cl)$=$CHCl$ | 1.42 |

*HPLC methode Data: Mobile Phase: A: Water + 0.1% TFA, B: acetonitrile; Gradient: 5% B to 100% B in 1.5 min; Temperature: 60° C.; MS method: ESI positive; mass area (m/z); 10-700; Flow: 0.8 ml/min to 1.0 ml/min in 1.5 min; Column: Kinetex XB C18 1.7 µ 50 × 2.1 mm; Aparatus: Shimadzu Nexera LC-30 LCMS-2020

EXAMPLE 1

Synthesis of 1-[2-[2-chloro-4-(4-chlorophenoxy) phenyl]-2-methoxy-but-3-enyl]-1,2,4-triazole (compound 1-7)

Step 1: 2-bromo-1-[2-chloro-4-(4-chlorophenoxy) phenyl]ethanone

1-[2-chloro-4-(4-chlorophenoxy)phenyl]ethanone (1000 g) was dissolved in MTBE (5000 mL) and a solution of bromine (563 g) in glacial acetic acid (400 mL) was added dropwise at room temperature. After completion of the addition the mixture was stirred for 1 h at room temperature and the pH was adjusted to 7-8 by addition of 10% NaOH solution. The organic layer was separated, extracted twice with MTBE and the combined organic phases were washed with sat. NaHCO3 solution (1×) and brine (2×). The solvent was evaporated and the crude product was used directly in the next step.

Step 2: 1-[2-chloro-4-(4-chlorophenoxy)phenyl]-2-(1,2,4-triazol-1-yl)ethanone 1,2,4-Triazole (249 g) was added carefully (small portions) to a mixture of sodium hydride (85 g) in THF (6000 mL). After 30 minutes a solution of 2-bromo-1-[2-chloro-4-(4-chlorophenoxy)phenyl]ethanone (1322 g) in THF (500 mL) was slowly added and the mixture was stirred for 150 min. The pH was adjusted to 7 with dil. hydrochloric acid whereupon water was added (3000 mL). The precipitate was filtered off and washed with MTBE. The organic phase was then concentrated and the resulting solid was filtered off to yield the desired material (1008 g).

Step 3.2-[2-chloro-4-(4-chlorophenoxy)phenyl]-1-(1,2,4-triazol-1-yl)but-3-en-2-ol A solution of 1-[2-chloro-4-(4-chlorophenoxy)phenyl]-2-(1,2,4-triazol-1-yl)ethanone (8 g) in dichloromethane (250 mL) was added slowly to a suspension of magnesiumbromide etherate (14 g) in dichloromethane (130 mL). The resulting mixture was stirred at room temperature for 1 h whereupon a solution of vinyl magnesium chloride in diethyl ether (1 M, 46 mL) was added dropwise at −15° C. The mixture was stirred for 2 h and allowed to thaw. 15% NH4Cl solution (200 mL) was added carefully under cooling. The phases were separated and the organic layer was subsequently washed with water and brine and dried. The solvent was evaporated under reduced pressure. The crude product was crystallized from MTBE to obtain 1.4 g of the desired compound.

Step 4: 1-[2-[2-chloro-4-(4-chlorophenoxy)phenyl]-2-methoxy-but-3-enyl]-1,2,4-triazole 2-[2-chloro-4-(4-chlorophenoxy)phenyl]-1-(1,2,4-triazol-1-yl)but-3-en-2-ol (0.4 g) was dissolved in THF (10 mL) and sodium hydride (0.03 g) was added. The mixture was stirred for 30 min at room temperature and methyl iodide (0.08 mL) was added. The mixture was then heated for 10 h to reflux. Brine and dichloro methane were added, the organic phase was dried and evaporated to obtain the crude product. This was purified by column chromatography to obtain 0.04 g of the desired compound.

II. Biology

1) Green House

The spray solutions were prepared in several steps:
The stock solution were prepared: a mixture of acetone and/or dimethylsulfoxide and the wetting agent/emulsifier Wettol, which is based on ethoxylated alkylphenoles, in a relation (volume) solvent-emulsifier of 99 to 1 was added to 25 mg of the compound to give a total of 5 ml. Water was then added to total volume of 100 ml.

This stock solution was diluted with the described solvent-emulsifier-water mixture to the given concentration.

G1. Preventative Control of Leaf Blotch on Wheat Caused by *Septoria tritici* (Septtr P1)

Leaves of pot-grown wheat seedling were sprayed to run-off with an aqueous suspension of the active compound or their mixture, prepared as described. The plants were allowed to air-dry. The next day the plants were inoculated with an aqueous spore suspension of *Septoria tritici*. Then the trial plants were immediately transferred to a humid chamber at 18-22° C. and a relative humidity close to 100%. After 4 days the plants were transferred to a chamber with 18-22° C. and a relative humidity close to 70%. After 4 weeks the extent of fungal attack on the leaves was visually assessed as % diseased leaf area. In this test, the plants which had been treated with 300 ppm of the active substance from examples I-1, I-7, I-8, I-11, I-12, I-13 and 1-15, respectively, showed an infection of equal to or less 1% whereas the untreated plants were 90% infected.

G2. Preventative Fungicidal Control of Early Blight on Tomatoes (*Alternaria solani*) (Alteso P1)

Young seedlings of tomato plants were grown in pots. These plants were sprayed to run-off with an aqueous suspension, containing the concentration of active ingredient or mixture mentioned in the table below. The next day, the treated plants were inoculated with an aqueous suspension of *Alternaria solani* Then the trial plants were immediately transferred to a humid chamber. After 5 days at 18 to 20° C. and a relative humidity close to 100%, the extent of fungal attack on the leaves was visually assessed as % diseased leaf area. In this test, the plants which had been treated with 300 ppm of the active substance from examples I-1, I-2, I-3, I-5, I-7, I-8, I-9, I-10, I-11, I-12, I-13 and 1-15, respectively, showed an infection of equal to or less than 7% whereas the untreated plants were 90% infected.

G3. Preventative Control of Brown Rust on Wheat Caused by *Puccinia recondite* (Puccrt P1)

The first two developed leaves of pot-grown wheat seedling were sprayed to run-off with an aqueous suspension, containing the concentration of active ingredient or their mixture as described below. The next day the plants were inoculated with spores of *Puccinia recondite*. To ensure the success the artificial inoculation, the plants were transferred to a humid chamber without light and a relative humidity of 95 to 99% and 20 to 24° C. for 24 h. Then the trial plants were cultivated for 6 days in a greenhouse chamber at 20-24° C. and a relative humidity between 65 and 70%. The extent of fungal attack on the leaves was visually assessed as % diseased leaf area. In this test, the plants which had been treated with 300 ppm of the active substance from examples I-1, I-2, I-3, I-4, I-5, I-7, I-8, I-9, I-10, I-11, I-12, I-13 and 1-15, respectively, showed an infection of equal to or less than 10% whereas the untreated plants were 70% infected.

G4. Preventative fungicidal control of *Botritis cinerea* on leaves of green pepper (Botrci P1)

Young seedlings of green pepper were grown in pots to the 4 to 5 leaf stage. These plants were sprayed to run-off with an aqueous suspension, containing the concentration of active ingredient or their mixture mentioned in the table below. The next day the plants were inoculated with a aqueous biomalt solution containing the spore suspension of *Botritis cinerea*. Then the plants were immediately transferred to a humid chamber. After 5 days at 22 to 24° C. and a relative humidity close to 100% the extent of fungal attack on the leaves was visually assessed as % diseased leaf area.

Microtest

The active compounds were formulated separately as a stock solution having a concentration of 10000 ppm in dimethyl sulfoxide.

M1. Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds

COMPARISON

| Structure | Disease (%) at 300 pm Septtr P1 | Disease (%) at 300 pm Botrci P1 | Growth (%) at 0.002 ppm Septtr |
|---|---|---|---|
| DE 3801233 table 1, compound 5 | 30 | 30 | |
| inventive compound I-8, table I | 0 | | |
| inventive compound I-12, table 1 | 0 | 0 | |
| DE 3801233 table 1, compound 2 | 40 | | 72 |
| inventive compound I-7, table I | 0 | | |
| inventive compound I-1, table I | | | 14 |
| unreated control | 90 | 90 | — |

The invention claimed is:

1. A compound of formula I

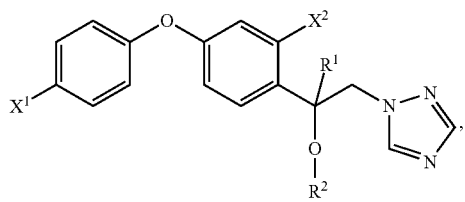

wherein:

$X^1$, $X^2$ independently of each other are selected from halogen;

$R^1$ is $C_2$-$C_6$-alkenyl or $C_2$-$C_6$-alkynyl; wherein the aliphatic moieties of $R^1$ may carry 1, 2 or 3 $R^a$, independently selected from CN, $C_1$-$C_2$-alkoxy and $C_1$-$C_2$-halogenalkoxy;

$R^2$ is $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, phenyl, phenyl-$C_1$-$C_4$-alkyl, phenyl-$C_2$-$C_4$-alkenyl or phenyl-$C_2$-$C_4$-alkynyl;

wherein the aliphatic moieties of $R^2$ may carry 1, 2, 3 or up to the maximum possible number of identical or different groups $R^a$ which independently of one another are selected from the group consisting of halogen, CN, nitro, phenyl, $C_1$-$C_4$-alkoxy and $C_1$-$C_4$-halogenalkoxy, wherein the phenyl may be be substituted by 1, 2, 3, 4 or 5 substituents selected from halogen, CN, nitro, $C_1$-$C_4$-alkyl, $C_1$-$C_4$-alkoxy, $C_1$-$C_4$-halogenalkyl and $C_1$-$C_4$-halogenalkoxy;

wherein the cycloalkyl and/or phenyl moieties of $R^2$ may carry 1, 2, 3, 4, 5 or up to the maximum number of identical or different groups $R^b$ which independently of one another are selected from the group consisting of halogen, CN, nitro, $C_1$-$C_4$-alkyl, $C_1$-$C_4$-alkoxy, $C_1$-$C_4$-halogenalkyl and $C_1$-$C_4$-halogenalkoxy;

or an N-oxide or an agriculturally acceptable salt thereof.

2. The compound of claim 1, wherein $X^1$ is Cl.

3. The compound of claim 1, wherein $X^2$ is Cl.

4. The compound of claim 1, wherein $R^1$ is $C_2$-$C_4$-alkenyl.

5. The compound of claim 1, wherein $R^1$ is $C_2$-$C_6$-alkynyl.

6. The compound of claim 1, wherein $R^1$ is unsubstituted.

7. The compound of claim 1, wherein $R^2$ is $C_1$-$C_4$-alkyl.

8. The compound of claim 1, wherein $X^1$ and $X^2$ are Cl, $R^1$ is C≡CH and $R^2$ is $CH_3$, $C_2H_5$, $CH_2C$≡CH, $CH_2C_6H_5$, or $CH_2CH_2CH_3$; and compounds wherein $X^1$ and $X^2$ are Cl, $R^1$ is CH═$CH_2$ and $R^2$ is $CH_3$, $CH_2CH$═$CH_2$, or $CH_2C$≡CH; and compounds wherein $X^1$ and $X^2$ are Cl, $R^1$ is C≡$CCH_3$ and $R^2$ is $CH_3$, $C_2H_5$, $CH_2CH$═$CH_2$, $CH_2C$≡CH or $CH_2C$(Cl)═CHCl; and compounds wherein $X^1$ and $X^2$ are Cl, $R^1$ is $CH_2C$≡CH and $R^2$ is $CH_2C$≡CH.

9. A process for preparing compounds of formula I as defined in claim 1, which comprises reacting a compound of formula IIIA

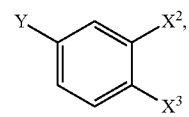

wherein Y is F or Cl and $X^3$ is I or Br, with a halo-phenole of formula II

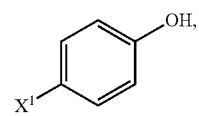

under basic conditions; reacting the resulting compound of formula IVa

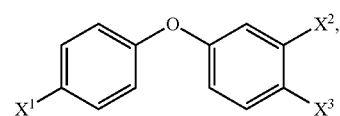

with isopropylmagnesium bromide followed by a reaction with acetyl chloride;

halogenating the resulting compound of formula V

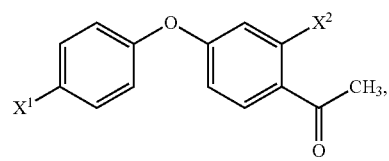

reacting the resulting compound of formula VI

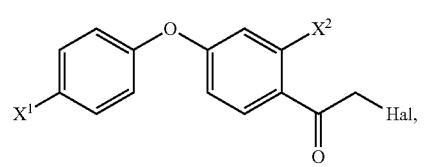

wherein Hal stands for halogen, under basic conditions with 1H-1,2,4-triazole;

reacting the resulting compound of formula VII

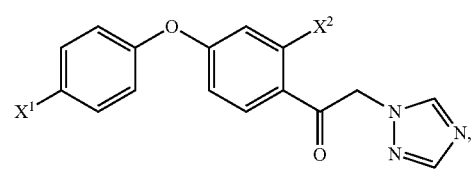

with $R^1$-M, wherein M is MgBr, MgCl, Li or Na; and reacting the resulting compound of VIII

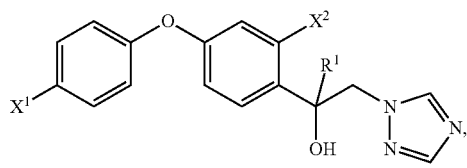
VIII under basic conditions with $R^2$-LG, wherein LG is a nucleophilically replaceable leaving group, to obtain compounds of formula I.

10. A process for preparing compounds of formula I as defined in claim 1, which comprises reacting a compound of formula IIIa

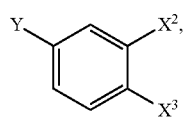

wherein Y is F or Cl and $X^3$ is I or Br; with isopropylmagnesium halide followed by a reaction with a compound of formula IX $R^1$—COCl;
converting the resulting compound of formula X

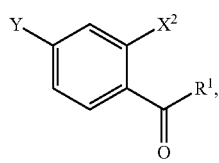
X wherein Y is F or Cl; under basic conditions with a halophenole of formula II

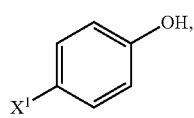
II reacting the resulting compound of formula Va

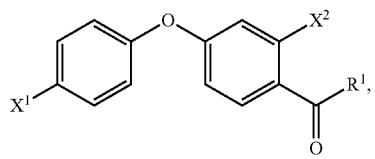
Va with trimethylsulf(ox)onium halide; reacting the resulting compound of formula XI

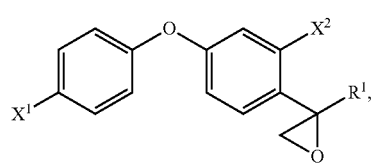
XI under basic conditions with 1H-1,2,4-triazole; and reacting the resulting compound of formula VIII

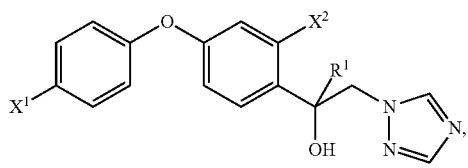
VIII under basic conditions with $R^2$-LG, wherein LG is a nucleophilically replaceable leaving group, to obtain compounds of formula I.

11. A process for preparing compounds of formula I as defined in claim 1, which comprises reacting a compound of formula XI

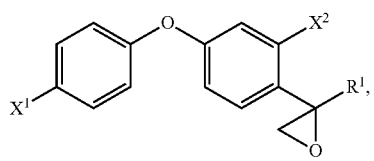
XI under acidic conditions with $R^2$—OH; reacting the resulting compound of formula XII

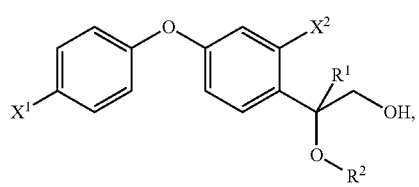
XII with a halogenating agent or sulfonating agent; reacting the resulting compound of formula XIII

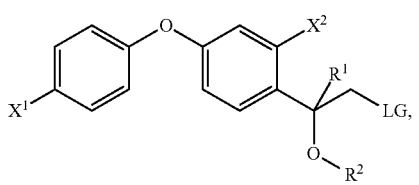
XIII wherein LG is a nucleophilically replaceable leaving group with 1H-1,2,4-triazole, to obtain compounds I.

12. An agrochemical composition comprising an auxiliary and at least one compound of claim 1, an N-oxide or an agriculturally acceptable salt thereof.

13. Seed coated with at least one compound of claim 1, in an amount of from 0.1 g to 10 kg per 100 kg of seed.

14. A method for controlling phytopathogenic harmful fungi, which comprises treating the fungi, their habitat or the plants to be protected against fungal attack, the soil or seeds with a compound of claim 1.

15. The method of claim 14, wherein $X^1$ is Cl.
16. The method of claim 14, wherein $X^2$ is Cl.
17. The method of claim 14, wherein $R^1$ is $C_2$-$C_4$-alkenyl.
18. The method of claim 14, wherein $R^1$ is $C_2$-$C_6$-alkynyl.

* * * * *